(12) United States Patent
Tang et al.

(10) Patent No.: US 10,793,884 B2
(45) Date of Patent: *Oct. 6, 2020

(54) METHODS AND MATERIALS FOR MAKING SIMVASTATIN AND RELATED COMPOUNDS

(71) Applicant: The Regents of the University of California, Oakland, CA (US)

(72) Inventors: Yi Tang, San Gabriel, CA (US); Xinkai Xie, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 25 days.

This patent is subject to a terminal disclaimer.

(21) Appl. No.: 15/971,738

(22) Filed: May 4, 2018

(65) Prior Publication Data

US 2018/0355391 A1    Dec. 13, 2018

Related U.S. Application Data

(60) Division of application No. 14/599,100, filed on Jan. 16, 2015, now Pat. No. 9,970,037, which is a division of application No. 13/540,188, filed on Jul. 2, 2012, now Pat. No. 8,951,754, which is a continuation of application No. 12/227,671, filed as application No. PCT/US2007/012362 on May 24, 2007, now Pat. No. 8,211,664.

(60) Provisional application No. 60/808,088, filed on May 24, 2006.

(51) Int. Cl.
| | | |
|---|---|---|
| *C12P 17/06* | (2006.01) | |
| *C12N 9/10* | (2006.01) | |
| *C12P 7/42* | (2006.01) | |
| *C12P 7/62* | (2006.01) | |

(52) U.S. Cl.
CPC ............ *C12P 17/06* (2013.01); *C12N 9/1025* (2013.01); *C12N 9/1029* (2013.01); *C12P 7/42* (2013.01); *C12P 7/62* (2013.01)

(58) Field of Classification Search
None
See application file for complete search history.

(56) References Cited

U.S. PATENT DOCUMENTS

| | | | |
|---|---|---|---|
| 6,391,583 B1 | 5/2002 | Hutchinson et al. | |
| 8,951,754 B2 * | 2/2015 | Tang | C12N 9/1029 435/41 |
| 2004/0033570 A1 | 2/2004 | Hutchinson et al. | |
| 2009/0191602 A1 | 7/2009 | Tang et al. | |

FOREIGN PATENT DOCUMENTS

| | | |
|---|---|---|
| WO | 0037629 | 6/2000 |
| WO | 03010324 | 2/2003 |
| WO | 2007147801 | 12/2007 |
| WO | 2009077523 | 6/2009 |
| WO | 2011041231 | 4/2011 |

OTHER PUBLICATIONS

Auclair et al. Conversion of cyclic nonaketides to lovastatin and compactin by a love deficient mutant of Aspergillus terreus. Bioorganic & Medicinal Chemistry Letters (2001 ), vol. 11, Issue 12, pp. 1527-1531.
Sorensen et al. Advanced genetic strategies for recombinant protein expression in *Escherichia coli.*, Journal of Biotechnology (Jan. 26, 2005), vol. 115, Issue 2, pp. 113-128.
Xie et al., "Biosynthesis of Lovastatin Analogs with a Broadly Specific Acyltransferase Chemistry & Biology 13", pp. 1161-1169, Nov. 2006.
Kennedy, J., el al., "Modulation of Polyketide Synthase Activity by Accessory Proteins During Lovastatin Biosynthesis", Science, American Association for the Advancement of Science, Washington, D.C; US, vol. 284, No. 5418, Jan. 1, 1999, pp. 1368-1372, XP000914559 ISSN: 0036-8075 DOI:10.1126/SCIENCE.284.5418.1368.
European Search Report dated Nov. 17, 2010, Application No. 07777257.2.
CN Office Action dated May 25, 2011 {CN application No. 200780027455.0) with translation.
GenBank: Q8FCT4 dated Sep. 13, 2005.
Sorensen, J. L., et al., "Transformations of cyclic nonaketides by Aspergillus terreus mutants blocked for lovastatin biosynthesis at the lovA and love genes", Org Biomol Chem, 1 (1 ):50-59, Nov. 21, 2002.
Guo et al., Protein tolerance to random amino acid change, 2004, Proc. Natl. Acad. Sci. USA 101: 9205-9210.
Lazar et al., Transforming Growth Factor a: Mutation of Aspartic Acid 47 and Leucine 48 Results in Different Biological Activity, 1988, Mol. Cell. Biol. 8:1247-1252.
Hill et al., Functional Analysis of conserved Histidines in ADP-Glucose Pyrophosphorylase from *Escherichia coli*, 1998, Biochem. Biophys. Res. Comm. 244:573-577.
Wacey et al., Disentangling the perturbational effects of amino acid substitutions in the DNA-binding domain of p53., Hum Genet, 1999, vol. 104, pp. 15-22.
European Search Report dated Feb. 26, 2013 for European Patent Application No. 10822785.1.

(Continued)

*Primary Examiner* — Anand U Desai

(74) *Attorney, Agent, or Firm* — Gates & Cooper LLP

(57) ABSTRACT

The invention disclosed herein relates to methods and materials for producing simvastatin and related compounds such as huvastatin.

20 Claims, 24 Drawing Sheets

Specification includes a Sequence Listing.

(56) References Cited

OTHER PUBLICATIONS

Abe, Y., et al., "Molecular cloning and characterization of an ML-236B (compactin) biosynthetic gene cluster in Penicillium citrinum", Molecular Genetics and Genomics (2002) 267, pp. 636-646, XP-002472854.

Abe, Y., et al., "Effect of increased dosage of the ML-236B (compactin) biosynthetic gene cluster on ML-236B production in Penicillium citrinum", Molecular Genetics and Genomics (2002) 268, pp. 130-137, XP-002400771.

Abe, Y., et al., "Subname: Full=Transesterase", Mar. 1, 2003, XP-002691905, retrieved from EBI accession No. UNIPROT:Q8J0G0.

Gao, Xue, et al., "Supplemental Data—Directed Evolution and Structural Characterization of a Simvastatin Synthase", Chemistry & Biology 16, Oct. 30, 2009, nine (9) pages, XP55052867.

Gao, Xue, et al., "Directed Evolution and Structural Characterization of a Simvastatin Synthase", Chemistry & Biology 16, Oct. 30, 2009, pp. 1064-1074, XP008154986.

Klaassen, P., et al, "Monascus pilosus esterase sequence, SEQ 51", Jul. 23, 2009, XP002691903, retrieved from EBI accession No. GSP: AXB24807.

Klaassen, P., et al, "Penicillium citrinum esterase sequence, SEQ 49", Jul. 23, 2009, XP002691904, retrieved from EBI accession No. GSP: AXB24805.

Xie, X., et al., "Efficient Synthesis of Simvastatin by Use of Whole-Cell Biocatalysis," Applied and Environmental Microbiology, Apr. 2007, pp. 2054-2060, vol. 73, No. 7, XP00247852.

Xie, X., et al., "Rational Improvement of Simvastatin Synthase Solubility in *Escherichia coli* Leads to Higher Whole-Cell Biocatalytic Activity," Biotechnology and Bioengineering, Jan. 2009, pp. 20-28, vol. 102, No. 1, XP008154985.

Chinese Office Action (with English translation) dated Aug. 5, 2013 for Chinese Patent Application No. 201080055195.X.

European Office Action dated Oct. 15, 2013 for European Patent Application No. 10822785.1.

Database UniProt [Online] Oct. 17, 2006 (Oct. 17, 2006), "Sub-Name: Full=Putative uncharacterized protein;" retrieved from EBI accession No. Uniprot:Q0C8M0 Database accession No. Q0C8M0.

Database Genesq [Online] May 26, 2011 (May 26, 2011), "Aspergillus terreus mutant LovD acyltransferase sequence, SEQ ID 60.", retrieved from EBI accession No. GSP:AZH26666 Database accession No. AZH26666.

Branden and Tooze, Intorduction to Protein Structure (1999), 2nd edition, Garland Science Publisher, pp. 3-12.

Unger et al., The Genetic Algorithm approach to Protein Structure Prediction, Structure and Bonding (2004), vo. 110, pp. 153-175.

Bhanothu et al., Review on characteristic developments of computational protein engineering, Journal of Pharmaceutical Research and Opinion (2012), vol. 2:8, pp. 70-93.

Grunberg et al., Strategies for protein synthetic biology, Nucleic Acids Research (2010), vol. 38(8), pp. 2663-2675.

Li et al.—B (Current Approaches for Engineering Proteins with Diverse Biological Properties, Adv Exp Med Biol. (2007-B) vol. 620, pp. 18-33.

Someya et al. Proceeding GECCO '09 Proceedings of the 11th Annual conference on Genetic and evolutionary computation, pp. 233-240 ACM New York, NY, USA © 2009.

Goomber et al., Enhancing thermostability of the biocatalysts beyond their natural function via protein engineering, International Journal for Biotechnology and Molecular Biology Research, (2012), vol. 3(3), pp. 24-29.

Buske et al., In silico characterization of protein chimeras: Relating sequence and function within the same fold, Proteins (2009), vol. 77, Issue 1, pp. 111-120.

\* cited by examiner

LovD Catalyzes
the acyltransfer to yield lovastatin.
The acyl donor is attached to LDKS.

Acyl-SNAC.
The shaded circle denotes any functional group.

SEQUENCE LISTING

<160> NUMBER OF SEQ ID NOS: 9

<210> SEQ ID NO 1
<211> LENGTH: 413
<212> TYPE: PRT
<213> ORGANISM: Aspergillus terreus

<400> SEQUENCE: 1

Met Gly Ser Ile Ile Asp Ala Ala Ala Ala Asp Pro Val Val Leu
1               5                   10                  15

Met Glu Thr Ala Phe Arg Lys Ala Val Lys Ser Arg Gln Ile Pro Gly
            20                  25                  30

Ala Val Ile Met Ala Arg Asp Cys Ser Gly Asn Leu Asn Tyr Thr Arg
        35                  40                  45

Cys Phe Gly Ala Arg Thr Val Arg Arg Asp Glu Cys Asn Gln Leu Pro
    50                  55                  60

Pro Leu Gln Val Asp Thr Pro Cys Arg Leu Ala Ser Ala Thr Lys Leu
65                  70                  75                  80

Leu Thr Thr Ile Met Ala Leu Gln Cys Met Glu Arg Gly Leu Val Asp
                85                  90                  95

Leu Asp Glu Thr Val Asp Arg Leu Leu Pro Asp Leu Ser Ala Met Pro
            100                 105                 110

Val Leu Glu Gly Phe Asp Asp Ala Gly Asn Ala Arg Leu Arg Glu Arg
        115                 120                 125

Arg Gly Lys Ile Thr Leu Arg His Leu Leu Thr His Thr Ser Gly Leu
    130                 135                 140

Ser Tyr Val Phe Leu His Pro Leu Leu Arg Glu Tyr Met Ala Gln Gly
145                 150                 155                 160

His Leu Gln Ser Ala Glu Lys Phe Gly Ile Gln Ser Arg Leu Ala Pro
                165                 170                 175

Pro Ala Val Asn Asp Pro Gly Ala Glu Trp Ile Tyr Gly Ala Asn Leu
            180                 185                 190

Asp Trp Ala Gly Lys Leu Val Glu Arg Ala Thr Gly Leu Asp Leu Glu
        195                 200                 205

Gln Tyr Leu Gln Glu Asn Ile Cys Ala Pro Leu Gly Ile Thr Asp Met
    210                 215                 220

Thr Phe Lys Leu Gln Gln Arg Pro Asp Met Leu Ala Arg Arg Ala Asp
225                 230                 235                 240

Gln Thr His Arg Asn Ser Ala Asp Gly Arg Leu Arg Tyr Asp Asp Ser
                245                 250                 255

Val Tyr Phe Arg Ala Asp Gly Glu Glu Cys Phe Gly Gly Gln Gly Val
            260                 265                 270

Phe Ser Gly Pro Gly Ser Tyr Met Lys Val Leu His Ser Leu Leu Lys
        275                 280                 285

Arg Asp Gly Leu Leu Leu Gln Pro Gln Thr Val Asp Leu Met Phe Gln
    290                 295                 300

Pro Ala Leu Glu Pro Arg Leu Glu Glu Gln Met Asn Gln His Met Asp
305                 310                 315                 320

Ala Ser Pro His Ile Asn Tyr Gly Gly Pro Met Pro Met Val Leu Arg
                325                 330                 335

Arg Ser Phe Gly Leu Gly Gly Ile Ile Ala Leu Glu Asp Leu Asp Gly
            340                 345                 350

Glu Asn Trp Arg Arg Lys Gly Ser Leu Thr Phe Gly Gly Gly Pro Asn
        355                 360                 365

```
Ile Val Trp Gln Ile Asp Pro Lys Ala Gly Leu Cys Thr Leu Ala Phe
370                 375                 380

Phe Gln Leu Glu Pro Trp Asn Asp Pro Val Cys Arg Asp Leu Thr Arg
385                 390                 395                 400

Thr Phe Glu His Ala Ile Tyr Ala Gln Tyr Gln Gln Gly
                405                 410

<210> SEQ ID NO 2
<211> LENGTH: 418
<212> TYPE: PRT
<213> ORGANISM: Penicillium citrinum

<400> SEQUENCE: 2

Met Ala Pro Ser Ile Asp Val Ile Pro Thr Ala Ala Ser Thr Ala Ala
1               5                   10                  15

Gly Met Ile Ser Asp Met Glu Ala Ala Phe Lys Ser Ala Val Lys Leu
                20                  25                  30

Lys Gln Ile Pro Gly Ala Val Val Met Ala Arg Ser Met Asn Gly Asp
            35                  40                  45

Ile Asp Tyr Thr Arg Cys Phe Gly Ala Arg Thr Val Glu Arg Asp Glu
        50                  55                  60

Cys Gln Arg Leu Pro Pro Met Glu Ile Asp Thr Pro Leu Arg Leu Ala
65                  70                  75                  80

Ser Ala Thr Lys Leu Leu Thr Thr Ile Met Ala Leu Gln Cys Met Glu
                85                  90                  95

Gln Gly Leu Val Asp Leu Asp Glu Asn Val Asn Arg Leu Leu Pro Asp
                100                 105                 110

Leu Ser Asp Met Gln Val Leu Thr Gly Phe Asp Ala Ala Gly Asn Ala
            115                 120                 125

Ile Met Arg Asp Arg Glu Gly Ile Ile Lys Leu Arg His Leu Leu Thr
        130                 135                 140

His Thr Ser Gly Leu Ser Tyr Ala Phe Leu His Pro Leu Leu Gln Glu
145                 150                 155                 160

Tyr Met Ala Lys Gly Tyr Leu Lys Thr Ala Glu Lys Phe Gly Ile Gln
                165                 170                 175

Ser Arg Leu Ala Pro Pro Ala Ile Asn Asp Pro Gly Val Glu Trp Ile
            180                 185                 190

Tyr Gly Ala Asn Leu Asp Trp Ala Gly Lys Leu Ile Glu Arg Ala Thr
        195                 200                 205

Gly Val Asp Leu Glu Glu Phe Met Gln Lys Asn Ile Cys Glu Pro Leu
210                 215                 220

Gly Ile Thr Asp Met Thr Phe Lys Leu Gln Gln Arg Pro Asp Met Leu
225                 230                 235                 240

Ala Arg Arg Ser Asp Gln Thr Arg Arg Asn Glu Asn Gly Ser Leu Arg
                245                 250                 255

Tyr Asp Asp Ser Val Tyr Phe Arg His Asp Gly Glu Glu Cys Phe Gly
            260                 265                 270

Gly Gln Gly Val Phe Cys Gly Pro Glu Ser Tyr Met Lys Val Leu Asn
        275                 280                 285

Ser Leu Met Lys His Asp Gly Leu Leu Leu Lys Asp Thr Ile Glu
290                 295                 300

Leu Met Phe Gln Pro Ala Leu Asp Ala Glu Leu Glu Lys Lys Met Asn
305                 310                 315                 320

Asp His Met Asp Thr Thr Pro His Ile Asn Tyr Gly Ala Ala Leu Pro
                325                 330                 335
```

-continued

Pro Val Met Arg Arg Asn Phe Gly Leu Gly Ile Ile Ala Met Gly
            340                 345                 350

Asp Leu Asp Gly His Asn Trp Arg Arg Glu Gly Ser Leu Thr Phe Gly
            355                 360                 365

Gly Gly Pro Asn Ile Val Trp Gln Ile Asp Pro Thr Val Gly Leu Cys
370                 375                 380

Thr Leu Val Val Phe Gln Leu Glu Pro Trp Asn Asp Pro Ile Cys Lys
385                 390                 395                 400

Asp Leu Thr Arg Lys Phe Glu Lys Ala Met Tyr Ser Gln Val Lys Cys
            405                 410                 415

Arg Asn

<210> SEQ ID NO 3
<211> LENGTH: 2532
<212> TYPE: PRT
<213> ORGANISM: Aspergillus terreus

<400> SEQUENCE: 3

Met Thr Pro Leu Asp Ala Pro Gly Ala Pro Ala Pro Ile Ala Met Val
1               5                   10                  15

Gly Met Gly Cys Arg Phe Gly Gly Gly Ala Thr Asp Pro Gln Lys Leu
            20                  25                  30

Trp Lys Leu Leu Glu Glu Gly Gly Ser Ala Trp Ser Lys Ile Pro Pro
        35                  40                  45

Ser Arg Phe Asn Val Gly Gly Val Tyr His Pro Asn Gly Gln Arg Val
    50                  55                  60

Gly Ser Met His Val Arg Gly Gly His Phe Leu Asp Glu Asp Pro Ala
65                  70                  75                  80

Leu Phe Asp Ala Ser Phe Phe Asn Met Ser Thr Glu Val Ala Ser Cys
                85                  90                  95

Met Asp Pro Gln Tyr Arg Leu Ile Leu Glu Val Val Tyr Glu Ala Leu
            100                 105                 110

Glu Ala Ala Gly Ile Pro Leu Glu Gln Val Ser Gly Ser Lys Thr Gly
        115                 120                 125

Val Phe Ala Gly Thr Met Tyr His Asp Tyr Gln Gly Ser Phe Gln Arg
    130                 135                 140

Gln Pro Glu Ala Leu Pro Arg Tyr Phe Ile Thr Gly Asn Ala Gly Thr
145                 150                 155                 160

Met Leu Ala Asn Arg Val Ser His Phe Tyr Asp Leu Arg Gly Pro Ser
                165                 170                 175

Val Ser Ile Asp Thr Ala Cys Ser Thr Thr Leu Thr Ala Leu His Leu
            180                 185                 190

Ala Ile Gln Ser Leu Arg Ala Gly Glu Ser Asp Met Ala Ile Val Ala
        195                 200                 205

Gly Ala Asn Leu Leu Leu Asn Pro Asp Val Phe Thr Thr Met Ser Asn
    210                 215                 220

Leu Gly Phe Leu Ser Ser Asp Gly Ile Ser Tyr Ser Phe Asp Ser Arg
225                 230                 235                 240

Ala Asp Gly Tyr Gly Arg Gly Glu Gly Val Ala Ala Ile Val Leu Lys
                245                 250                 255

Thr Leu Pro Asp Ala Val Arg Asp Gly Asp Pro Ile Arg Leu Ile Val
            260                 265                 270

Arg Glu Thr Ala Ile Asn Gln Asp Gly Arg Thr Pro Ala Ile Ser Thr
        275                 280                 285

```
Pro Ser Gly Glu Ala Gln Glu Cys Leu Ile Gln Asp Cys Tyr Gln Lys
    290                 295                 300

Ala Gln Leu Asp Pro Lys Gln Thr Ser Tyr Val Glu Ala His Gly Thr
305                 310                 315                 320

Gly Thr Arg Ala Gly Asp Pro Leu Glu Leu Ala Val Ile Ser Ala Ala
                325                 330                 335

Phe Pro Gly Gln Gln Ile Gln Val Gly Ser Val Lys Ala Asn Ile Gly
                340                 345                 350

His Thr Glu Ala Val Ser Gly Leu Ala Ser Leu Ile Lys Val Ala Leu
            355                 360                 365

Ala Val Glu Lys Gly Val Ile Pro Pro Asn Ala Arg Phe Leu Gln Pro
    370                 375                 380

Ser Lys Lys Leu Leu Lys Asp Thr His Ile Gln Ile Pro Leu Cys Ser
385                 390                 395                 400

Gln Ser Trp Ile Pro Thr Asp Gly Val Arg Arg Ala Ser Ile Asn Asn
                405                 410                 415

Phe Gly Phe Gly Gly Ala Asn Ala His Ala Ile Val Glu Gln Tyr Gly
                420                 425                 430

Pro Phe Ala Glu Thr Ser Ile Cys Pro Pro Asn Gly Tyr Ser Gly Asn
            435                 440                 445

Tyr Asp Gly Asn Leu Gly Thr Asp Gln Ala His Ile Tyr Val Leu Ser
    450                 455                 460

Ala Lys Asp Glu Asn Ser Cys Met Arg Met Val Ser Arg Leu Cys Asp
465                 470                 475                 480

Tyr Ala Thr His Ala Arg Pro Ala Asp Asp Leu Gln Leu Leu Ala Asn
                485                 490                 495

Ile Ala Tyr Thr Leu Gly Ser Arg Arg Ser Asn Phe Arg Trp Lys Ala
                500                 505                 510

Val Cys Thr Ala His Ser Leu Thr Gly Leu Ala Gln Asn Leu Ala Gly
            515                 520                 525

Glu Gly Met Arg Pro Ser Lys Ser Ala Asp Gln Val Arg Leu Gly Trp
    530                 535                 540

Val Phe Thr Gly Gln Gly Ala Gln Trp Phe Ala Met Gly Arg Glu Leu
545                 550                 555                 560

Ile Glu Met Tyr Pro Val Phe Lys Glu Ala Leu Leu Glu Cys Asp Gly
                565                 570                 575

Tyr Ile Lys Glu Met Gly Ser Thr Trp Ser Ile Ile Glu Glu Leu Ser
                580                 585                 590

Arg Pro Glu Thr Glu Ser Arg Val Asp Gln Ala Glu Phe Ser Leu Pro
            595                 600                 605

Leu Ser Thr Ala Leu Gln Ile Ala Leu Val Arg Leu Leu Trp Ser Trp
    610                 615                 620

Asn Ile Gln Pro Val Ala Val Thr Ser His Ser Ser Gly Glu Ala Ala
625                 630                 635                 640

Ala Ala Tyr Ala Ile Gly Ala Leu Thr Ala Arg Ser Ala Ile Gly Ile
                645                 650                 655

Ser Tyr Ile Arg Gly Ala Leu Thr Ala Arg Asp Arg Leu Ala Ser Val
                660                 665                 670

His Lys Gly Gly Met Leu Ala Val Gly Leu Ser Arg Ser Glu Val Gly
            675                 680                 685

Ile Tyr Ile Arg Gln Val Pro Leu Gln Ser Glu Glu Cys Leu Val Val
    690                 695                 700
```

-continued

```
Gly Cys Val Asn Ser Pro Ser Ser Val Thr Val Ser Gly Asp Leu Ser
705                 710                 715                 720

Ala Ile Ala Lys Leu Glu Glu Leu Leu His Ala Asp Arg Ile Phe Ala
            725                 730                 735

Arg Arg Leu Lys Val Thr Gln Ala Phe His Ser Ser His Met Asn Ser
                740                 745                 750

Met Thr Asp Ala Phe Arg Ala Gly Leu Thr Glu Leu Phe Gly Ala Asp
            755                 760                 765

Pro Ser Asp Ala Ala Asn Ala Ser Lys Asp Val Ile Tyr Ala Ser Pro
        770                 775                 780

Arg Thr Gly Ala Arg Leu His Asp Met Asn Arg Leu Arg Asp Pro Ile
785                 790                 795                 800

His Trp Val Glu Cys Met Leu His Pro Val Glu Phe Glu Ser Ala Phe
                805                 810                 815

Arg Arg Met Cys Leu Asp Glu Asn Asp His Met Pro Lys Val Asp Arg
                820                 825                 830

Val Ile Glu Ile Gly Pro His Gly Ala Leu Gly Gly Pro Ile Lys Gln
            835                 840                 845

Ile Met Gln Leu Pro Glu Leu Ala Thr Cys Asp Ile Pro Tyr Leu Ser
850                 855                 860

Cys Leu Ser Arg Gly Lys Ser Ser Leu Ser Thr Leu Arg Leu Leu Ala
865                 870                 875                 880

Ser Glu Leu Ile Arg Ala Gly Phe Pro Val Asp Leu Asn Ala Ile Asn
                885                 890                 895

Phe Pro Arg Gly Cys Glu Ala Ala Arg Val Gln Val Leu Ser Asp Leu
            900                 905                 910

Pro Pro Tyr Pro Trp Asn His Glu Thr Arg Tyr Trp Lys Glu Pro Arg
        915                 920                 925

Ile Ser Gln Ser Ala Arg Gln Arg Lys Gly Pro Val His Asp Leu Ile
    930                 935                 940

Gly Leu Gln Glu Pro Leu Asn Leu Pro Leu Ala Arg Ser Trp His Asn
945                 950                 955                 960

Val Leu Arg Val Ser Asp Leu Pro Trp Leu Arg Asp His Val Val Gly
                965                 970                 975

Ser His Ile Val Phe Pro Gly Ala Gly Phe Val Cys Met Ala Val Met
                980                 985                 990

Gly Ile Ser Thr Leu Cys Ser Ser Asp His Glu Ser Asp Asp Ile Ser
            995                 1000                1005

Tyr Ile Leu Arg Asp Val Asn Phe Ala Gln Ala Leu Ile Leu Pro Ala
    1010                1015                1020

Asp Gly Glu Glu Gly Ile Asp Leu Arg Leu Thr Ile Cys Ala Pro Asp
1025                1030                1035                1040

Gln Ser Leu Gly Ser Gln Asp Trp Gln Arg Phe Leu Val His Ser Ile
                1045                1050                1055

Thr Ala Asp Lys Asn Asp Trp Thr Glu His Cys Thr Gly Leu Val Arg
            1060                1065                1070

Ala Glu Met Asp Gln Pro Ser Ser Leu Ser Asn Gln Gln Arg Ile
        1075                1080                1085

Asp Pro Arg Pro Trp Ser Arg Lys Thr Ala Pro Gln Glu Leu Trp Asp
    1090                1095                1100

Ser Leu His Arg Val Gly Ile Arg His Gly Pro Phe Phe Arg Asn Ile
1105                1110                1115                1120

Thr Cys Ile Glu Ser Asp Gly Arg Gly Ser Trp Cys Thr Phe Ala Ile
```

-continued

```
                1125                1130                1135
Ala Asp Thr Ala Ser Ala Met Pro His Ala Tyr Glu Ser Gln His Ile
                1140                1145                1150

Val His Pro Thr Thr Leu Asp Ser Ala Val Gln Ala Ala Tyr Thr Thr
                1155                1160                1165

Leu Pro Phe Ala Gly Ser Arg Ile Lys Ser Ala Met Val Pro Ala Arg
        1170                1175                1180

Val Gly Cys Met Lys Ile Ser Ser Arg Leu Ala Asp Leu Glu Ala Arg
1185                1190                1195                1200

Asp Met Leu Arg Ala Gln Ala Lys Met His Ser Gln Ser Pro Ser Ala
                1205                1210                1215

Leu Val Thr Asp Val Ala Val Phe Asp Glu Ala Asp Pro Val Gly Gly
                1220                1225                1230

Pro Val Met Glu Leu Glu Gly Leu Val Phe Gln Ser Leu Gly Ala Ser
                1235                1240                1245

Leu Gly Thr Ser Asp Arg Asp Ser Thr Asp Pro Gly Asn Thr Cys Ser
            1250                1255                1260

Ser Trp His Trp Ala Pro Asp Ile Ser Leu Val Asn Pro Gly Trp Leu
1265                1270                1275                1280

Glu Lys Thr Leu Gly Thr Gly Ile Gln Glu His Glu Ile Ser Leu Ile
                1285                1290                1295

Leu Glu Leu Arg Arg Cys Ser Val His Phe Ile Gln Glu Ala Met Glu
                1300                1305                1310

Ser Leu Ser Val Gly Asp Val Glu Arg Leu Ser Gly His Leu Ala Lys
            1315                1320                1325

Phe Tyr Ala Trp Met Gln Lys Gln Leu Ala Cys Ala Gln Asn Gly Glu
            1330                1335                1340

Leu Gly Pro Glu Ser Ser Ser Trp Thr Arg Asp Ser Glu Gln Ala Arg
1345                1350                1355                1360

Cys Ser Leu Arg Ser Arg Val Val Ala Gly Ser Thr Asn Gly Glu Met
                1365                1370                1375

Ile Cys Arg Leu Gly Ser Val Leu Pro Ala Ile Leu Arg Arg Glu Val
            1380                1385                1390

Asp Pro Leu Glu Val Met Met Asp Gly His Leu Leu Ser Arg Tyr Tyr
            1395                1400                1405

Val Asp Ala Leu Lys Trp Ser Arg Ser Asn Ala Gln Ala Ser Glu Leu
        1410                1415                1420

Val Arg Leu Cys Cys His Lys Asn Pro Arg Ala Arg Ile Leu Glu Ile
1425                1430                1435                1440

Gly Gly Gly Thr Gly Gly Cys Thr Gln Leu Val Val Asp Ser Leu Gly
                1445                1450                1455

Pro Asn Pro Pro Val Gly Arg Tyr Asp Phe Thr Asp Val Ser Ala Gly
            1460                1465                1470

Phe Phe Glu Ala Ala Arg Lys Arg Phe Ala Gly Trp Gln Asn Val Met
            1475                1480                1485

Asp Phe Arg Lys Leu Asp Ile Glu Asp Asp Pro Glu Ala Gln Gly Phe
        1490                1495                1500

Val Cys Gly Ser Tyr Asp Val Val Leu Ala Cys Gln Val Leu His Ala
1505                1510                1515                1520

Thr Ser Asn Met Gln Arg Thr Leu Thr Asn Val Arg Lys Leu Leu Lys
                1525                1530                1535

Pro Gly Gly Lys Leu Ile Leu Val Glu Thr Thr Arg Asp Glu Leu Asp
                1540                1545                1550
```

```
Leu Phe Phe Thr Phe Gly Leu Leu Pro Gly Trp Trp Leu Ser Glu Glu
            1555                1560                1565

Pro Glu Arg Gln Ser Thr Pro Ser Leu Ser Pro Thr Met Trp Arg Ser
        1570                1575                1580

Met Leu His Thr Thr Gly Phe Asn Gly Val Glu Val Glu Ala Arg Asp
1585                1590                1595                1600

Cys Asp Ser His Glu Phe Tyr Met Ile Ser Thr Met Met Ser Thr Ala
                1605                1610                1615

Val Gln Ala Thr Pro Met Ser Cys Ser Val Lys Leu Pro Glu Val Leu
            1620                1625                1630

Leu Val Tyr Val Asp Ser Ser Thr Pro Met Ser Trp Ile Ser Asp Leu
        1635                1640                1645

Gln Gly Glu Ile Arg Gly Arg Asn Cys Ser Val Thr Ser Leu Gln Ala
            1650                1655                1660

Leu Arg Gln Val Pro Pro Thr Glu Gly Gln Ile Cys Val Phe Leu Gly
1665                1670                1675                1680

Glu Val Glu His Ser Met Leu Gly Ser Val Thr Asn Asp Asp Phe Thr
                1685                1690                1695

Leu Leu Thr Ser Met Leu Gln Leu Ala Gly Gly Thr Leu Trp Val Thr
            1700                1705                1710

Gln Gly Ala Thr Met Lys Ser Asp Asp Pro Leu Lys Ala Leu His Leu
        1715                1720                1725

Gly Leu Leu Arg Thr Met Arg Asn Glu Ser His Gly Lys Arg Phe Val
            1730                1735                1740

Ser Leu Asp Leu Asp Pro Ser Arg Asn Pro Trp Thr Gly Asp Ser Arg
1745                1750                1755                1760

Asp Ala Ile Val Ser Val Leu Asp Leu Ile Ser Met Ser Asp Glu Lys
                1765                1770                1775

Glu Phe Asp Tyr Ala Glu Arg Asp Gly Val Ile His Val Pro Arg Ala
            1780                1785                1790

Phe Ser Asp Ser Ile Asn Gly Gly Glu Glu Asp Gly Tyr Ala Leu Glu
        1795                1800                1805

Pro Phe Gln Asp Ser Gln His Leu Leu Arg Leu Asp Ile Gln Thr Pro
            1810                1815                1820

Gly Leu Leu Asp Ser Leu His Phe Thr Lys Arg Asn Val Asp Thr Tyr
1825                1830                1835                1840

Glu Pro Asp Lys Leu Pro Asp Asp Trp Val Glu Ile Glu Pro Arg Ala
                1845                1850                1855

Phe Gly Leu Asn Phe Arg Asp Ile Met Val Ala Met Gly Gln Leu Glu
            1860                1865                1870

Ser Asn Val Met Gly Phe Glu Cys Ala Gly Val Val Thr Ser Leu Ser
        1875                1880                1885

Glu Thr Ala Arg Thr Ile Ala Pro Gly Leu Ala Val Gly Asp Arg Val
        1890                1895                1900

Cys Ala Leu Met Asn Gly His Trp Ala Ser Arg Val Thr Thr Ser Arg
1905                1910                1915                1920

Thr Asn Val Val Arg Ile Pro Glu Thr Leu Ser Phe Pro His Ala Ala
                1925                1930                1935

Ser Ile Pro Leu Ala Phe Thr Thr Ala Tyr Ile Ser Leu Tyr Thr Val
            1940                1945                1950

Ala Arg Ile Leu Pro Gly Glu Thr Val Leu Ile His Ala Gly Ala Gly
        1955                1960                1965
```

```
Gly Val Gly Gln Ala Ala Ile Ile Leu Ala Gln Leu Thr Gly Ala Glu
    1970                1975                1980

Val Phe Thr Thr Ala Gly Ser Glu Thr Lys Arg Asn Leu Leu Ile Asp
1985                1990                1995                2000

Lys Phe His Leu Asp Pro Asp His Val Phe Ser Ser Arg Asp Ser Ser
                2005                2010                2015

Phe Val Asp Gly Ile Lys Thr Arg Thr Arg Gly Lys Gly Val Asp Val
            2020                2025                2030

Val Leu Asn Ser Leu Ala Gly Pro Leu Leu Gln Lys Ser Phe Asp Cys
        2035                2040                2045

Leu Ala Arg Phe Gly Arg Phe Val Glu Ile Gly Lys Lys Asp Leu Glu
    2050                2055                2060

Gln Asn Ser Arg Leu Asp Met Ser Thr Phe Val Arg Asn Val Ser Phe
2065                2070                2075                2080

Ser Ser Val Asp Ile Leu Tyr Trp Gln Gln Ala Lys Pro Ala Glu Ile
                2085                2090                2095

Phe Gln Ala Met Ser Glu Val Ile Leu Leu Trp Glu Arg Thr Ala Ile
            2100                2105                2110

Gly Leu Ile His Pro Ile Ser Glu Tyr Pro Met Ser Ala Leu Glu Lys
        2115                2120                2125

Ala Phe Arg Thr Met Gln Ser Gly Gln His Val Gly Lys Ile Val Val
    2130                2135                2140

Thr Val Ala Pro Asp Asp Ala Val Leu Val Arg Gln Glu Arg Met Pro
2145                2150                2155                2160

Leu Phe Leu Lys Pro Asn Val Ser Tyr Leu Val Ala Gly Gly Leu Gly
                2165                2170                2175

Gly Ile Gly Arg Arg Ile Cys Glu Trp Leu Val Asp Arg Gly Ala Arg
            2180                2185                2190

Tyr Leu Ile Ile Leu Ser Arg Thr Ala Arg Val Asp Pro Val Val Thr
        2195                2200                2205

Ser Leu Gln Glu Arg Gly Cys Thr Val Ser Val Gln Ala Cys Asp Val
    2210                2215                2220

Ala Asp Glu Ser Gln Leu Glu Ala Ala Leu Gln Gln Cys Arg Ala Glu
2225                2230                2235                2240

Glu Met Pro Pro Ile Arg Gly Val Ile Gln Gly Ala Met Val Leu Lys
                2245                2250                2255

Asp Ala Leu Val Ser Gln Met Thr Ala Asp Gly Phe His Ala Ala Leu
            2260                2265                2270

Arg Pro Lys Val Gln Gly Ser Trp Asn Leu His Arg Ile Ala Ser Asp
        2275                2280                2285

Val Asp Phe Phe Val Met Leu Ser Ser Leu Val Gly Val Met Gly Gly
    2290                2295                2300

Ala Gly Gln Ala Asn Tyr Ala Ala Ala Gly Ala Phe Gln Asp Ala Leu
2305                2310                2315                2320

Ala Glu His Arg Met Ala His Asn Gln Pro Ala Val Thr Ile Asp Leu
                2325                2330                2335

Gly Met Val Gln Ser Ile Gly Tyr Val Ala Glu Thr Asp Ser Ala Val
            2340                2345                2350

Ala Glu Arg Leu Gln Arg Ile Gly Tyr Gln Pro Leu His Glu Glu Glu
        2355                2360                2365

Val Leu Asp Val Leu Glu Gln Ala Ile Ser Pro Val Cys Ser Pro Ala
    2370                2375                2380

Ala Pro Thr Arg Pro Ala Val Ile Val Thr Gly Ile Asn Thr Arg Pro
```

```
                    2385                2390                2395                2400
Gly Pro His Trp Ala His Ala Asp Trp Met Gln Glu Ala Arg Phe Ala
                2405                2410                2415

Gly Ile Lys Tyr Arg Asp Pro Leu Arg Asp Asn His Gly Ala Leu Ser
                2420                2425                2430

Leu Thr Pro Ala Glu Asp Asp Asn Leu His Ala Arg Leu Asn Arg Ala
                2435                2440                2445

Ile Ser Gln Gln Glu Ser Ile Ala Val Ile Met Glu Ala Met Ser Cys
                2450                2455                2460

Lys Leu Ile Ser Met Phe Gly Leu Thr Asp Ser Glu Met Ser Ala Thr
2465                2470                2475                2480

Gln Thr Leu Ala Gly Ile Gly Val Asp Ser Leu Val Ala Ile Glu Leu
                2485                2490                2495

Arg Asn Trp Ile Thr Ala Lys Phe Asn Val Asp Ile Ser Val Phe Glu
                2500                2505                2510

Leu Met Glu Gly Arg Thr Ile Ala Lys Val Ala Glu Val Val Leu Gln
                2515                2520                2525

Arg Tyr Lys Ala
        2530

<210> SEQ ID NO 4
<211> LENGTH: 256
<212> TYPE: PRT
<213> ORGANISM: Escherichia coli

<400> SEQUENCE: 4

Met Asn Asn Ile Trp Trp Gln Thr Lys Gly Gln Gly Asn Val His Leu
1               5                   10                  15

Val Leu Leu His Gly Trp Gly Leu Asn Ala Glu Val Trp Arg Cys Ile
            20                  25                  30

Asp Glu Glu Leu Ser Ser His Phe Thr Leu His Leu Val Asp Leu Pro
        35                  40                  45

Gly Phe Gly Arg Ser Arg Gly Phe Gly Ala Leu Ser Leu Ala Asp Met
    50                  55                  60

Ala Glu Ala Val Leu Gln Gln Ala Pro Asp Lys Ala Ile Trp Leu Gly
65                  70                  75                  80

Trp Ser Leu Gly Gly Leu Val Ala Ser Gln Ile Ala Leu Thr His Pro
                85                  90                  95

Glu Arg Val Gln Ala Leu Val Thr Val Ala Ser Ser Pro Cys Phe Ser
            100                 105                 110

Ala Arg Asp Glu Trp Pro Gly Ile Lys Pro Asp Val Leu Ala Gly Phe
        115                 120                 125

Gln Gln Gln Leu Ser Asp Asp Phe Gln Arg Thr Val Glu Arg Phe Leu
    130                 135                 140

Ala Leu Gln Thr Met Gly Thr Glu Thr Ala Arg Gln Asp Ala Arg Ala
145                 150                 155                 160

Leu Lys Lys Thr Val Leu Ala Leu Pro Met Pro Glu Val Asp Val Leu
                165                 170                 175

Asn Gly Gly Leu Glu Ile Leu Lys Thr Val Asp Leu Arg Gln Pro Leu
            180                 185                 190

Gln Asn Val Ser Met Pro Phe Leu Arg Leu Tyr Gly Tyr Leu Asp Gly
        195                 200                 205

Leu Val Pro Arg Lys Val Val Pro Met Leu Asp Lys Leu Trp Pro His
    210                 215                 220
```

```
Ser Glu Ser Tyr Ile Phe Ala Lys Ala Ala His Ala Pro Phe Ile Ser
225                 230                 235                 240

His Pro Ala Glu Phe Cys His Leu Leu Val Ala Leu Lys Gln Arg Val
                245                 250                 255

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
aacatatgaa taacatctgg tggca                                         25

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
aagaattcta caccctctgc ttcaacg                                       27

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
tgacggcttc gctatcccat                                               20

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
tacaccctct gcttcaacg                                                19

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gctggattgt ttcgccgatc                                               20
```

US 10,793,884 B2

METHODS AND MATERIALS FOR MAKING SIMVASTATIN AND RELATED COMPOUNDS

CROSS REFERENCE TO RELATED APPLICATIONS

This application is a divisional application that claims the benefit under 35 U.S.C. § 121 of U.S. patent application Ser. No. 14/599,100, filed Jan. 16, 2015, which is a divisional application that claims the benefit under 35 U.S.C. § 121 of U.S. patent application Ser. No. 13/540,188, filed Jul. 2, 2012, now U.S. Pat. No. 8,951,754, which is a continuation of U.S. patent application Ser. No. 12/227,671, filed Nov. 24, 2008, now U.S. Pat. No. 8,211,664, which is the National Stage of International Application No. PCT/US2007/012362 (International Publication No. WO2007/139871), filed May 24, 2007, which claims priority under Section 119(e) from U.S. provisional patent application No. 60/808,088, filed May 24, 2006, the entire contents of which are incorporated herein by reference.

FIELD OF THE INVENTION

The invention relates to methods and materials for biosynthesizing compounds such as simvastatin including procedures using microbial hosts.

BACKGROUND OF THE INVENTION

Simvastatin is a semisynthetic derivative of the natural product lovastatin, which can be isolated from the fermentation broth of *Aspergillus terreus*. Both lovastatin and simvastatin are cholesterol lowering drugs that substantially lower the risk of heart disease among adults. Lovastatin and simvastatin are marketed by Merck Co. as Mevacor and Zocor, respectively. Simvastatin is a more potent derivative of lovastatin and is the second best selling drug in the United States in 2005, with an expect sales of $4.5 billion in the US alone.

The gene cluster for lovastatin biosynthesis in *A. terreus* (see, e.g., J. Kennedy, K. et. al., *Science*, 1999, 284, 1368-1372; and C. R. Hutchinson, J. et. al., *Antonie Van Leeuwenhoek* 2000, 78, 287-295) has been described previously (see, e.g., U.S. Pat. No. 6,391,583, the contents of which are herein incorporated by reference). Encoded in the gene cluster is a 46 kD protein LovD, that was initially identified as an esterase homolog. Monacolin J, the immediate biosynthetic precursor of lovastatin, is assembled by the upstream megasynthase LovB (see, e.g., L. Hendrickson, C. R. et. al., *Chem. Biol.* 1999, 6, 429-439), (also known as lovastatin nonaketide synthase, LNKS), enoylreductase LovC and CYP450 oxygenases. The five carbon unit side chain is synthesized by LovF (lovastatin diketide synthase, LDKS) through condensation between an acetyl-CoA and a malonyl-CoA. The condensed diketide undergoes methylation and reductive tailoring by the individual LovF domains to yield an α-S-methylbutyryl thioester covalently attached to the phosphopantetheine arm on the acyl carrier protein (ACP) domain of LovF (see, e.g., J. Kennedy, K. et. al., *Science*, 1999, 284, 1368-1372 and C. R. Hutchinson, J. et. al., *Antonie Van Leeuwenhoek* 2000, 78, 287-295), and Lovastatin is subsequently produced from monacolin J. Inactivation of either LovD or LovF in *A. terreus* leads to accumulation of the precursor monacolin J (see, e.g., J. Kennedy, K. et. al., *Science*, 1999, 284, 1368-1372 and C. R. Hutchinson, J. et. al., *Antonie Van Leeuwenhoek* 2000, 78, 287-295).

Once lovastatin is produced via fermentation in an *A. terreus* host for example, simvastatin can be produced from lovastatin. Currently, simvastatin is a semisynthetic derivative of lovastatin. Lovastatin is obtained via fermentation of the *A. terreus* host. After purification of the compound, the semisynthesis can proceed as follows: 1) the 2-methylbutyrate side arm can be hydrolyzed in the presence of base to yield the intermediate monacolin J; 2) lactonize the free acid; 3) the alcohol functional group at C13 is protected with a protection group (such as tert-butyldimethylsilyl); 4) Esterification of the exposed C8 alcohol with an acyl substrate such as 2-dimethylbutyryl chloride to yield a C13 protected version of simvastatin, and 5) Deprotection of C13 OH to yield simvastatin (FIG. 3).

Various multistep synthesis of simvastatin have been described previously (see, e.g., PCT WO 2005/066150 and U.S. Application Nos. 20050080275 and 20040068123, the contents of which are herein incorporated by reference). For example, a widely used process starts with the hydrolysis of the C8 ester in lovastatin to yield the triol monacolin J, followed by selective silylation of the C13 alcohol, esterification of C8 alcohol with dimethylbutyryl chloride and deprotection of C13 alcohol to yield simvastatin (see, e.g., W. F. Hoffman, et. al., *J. Med. Chem.* 1986, 29, 849-852). Enzymatic transformations using lipases and esterases have been investigated as alternatives to chemical derivation (see, e.g., PCT WO 2005/040107, PCT WO 94/26920 and T. G. Schimmel, et. al., *Appl. Environ. Microbiol.* 1997, 63, 1307-1311, the contents of which are herein incorporated by reference). However, the requirement of regioselective esterification invariably involves protection of other alcohol groups and often leads to lowered overall yield. Therefore, a specific reagent that is able to selectively acylate C8 of monacolin J is important towards the efficient synthesis of simvastatin and additional statin analogs.

Variations of the above schemes are common, however, most procedures will invariably involve isolation of lovastatin first, hydrolysis of the methylbutyrate side chain, protection of the free alcohol, reaction with an acyl substrate, and deprotection. Although the chemical transformations involved are relatively simple, they are inefficient and involve multiple steps and therefore contribute to the current high cost of manufacturing simvastatin ($3 per pill).

SUMMARY OF THE INVENTION

The present invention provides methods and materials designed to take advantage of biological processes by which lovastatin is made in order to produce the lovastatin derivative, simvastatin. The present invention also provides methods and materials designed to take advantage of biological processes by which lovastatin is made in order to produce related compounds such as the pravastatin derivative, huvastatin. As noted above, biological processes for the production of lovastatin from the fermentation of *A. terreus* are well known in the art. In typical processes for producing lovastatin, the decalin core and the HMG-CoA moieties that mimic portions of the lovastatin compound are synthesized by the lovastatin nonaketide synthase (LNKS) and three accessory enzymes in vivo. The 2-methylbutyrate side chain is synthesized by lovastatin diketide synthase (LDKS) in vivo. The 2-methylbutyrate is covalently attached to the acyl carrier domain of LovF via a thioester linkage (FIG. 6). An acyltransferase, LovD, then is able to transfer the 2-methylbutyrate selectively to the C8 hydroxyl group from LDKS in one step to yield lovastatin. As disclosed in detail below, it is now possible to generate simvastatin and related compounds both in vitro or in vivo by manipulating these processes.

Embodiments of the invention include methods for generating simvastatin without the multiple chemical synthesis steps that are currently employed to generate this compound. Typical embodiments of the invention do not require the purification of lovastatin as a first step, followed by the further semisynthetic procedures and instead use a single fermentation step to produce simvastatin. The processes disclosed herein are designed so that fermentation facilities currently producing lovastatin can be converted to producing simvastatin and related compounds with minimal modifications. The materials used in the processes disclosed herein are relatively inexpensive and the purification steps are well known in the art and easily practiced.

Those of skill in the art will understand that the disclosure provided herein allows artisans to produce a wide variety of embodiments of the invention. A typical embodiment of the invention is a method of making simvastatin by combining together monacolin J; an acyl thioester that donates an acyl moiety to the C8 hydroxyl group of monacolin J in the presence of LovD acyltransferase; and LovD acyltransferase; and then allowing the LovD acyltransferase use an acyl group from the acyl thioester to regioselectively acylate the C8 hydroxyl group of monacolin J; so that simvastatin is made. In typical embodiments of the invention, the LovD acyltransferase has the amino acid sequence of SEQ ID NO: 1 or SEQ ID NO: 2. A related embodiment of the invention is a method of making simvastatin comprising the steps of combining together lovastatin; an acyl thioester that donates an acyl moiety to the C8 hydroxyl group of monacolin J in the presence of LovD acyltransferase; and LovD acyltransferase. In this embodiment of the method, the LovD acyltransferase is then allowed to hydrolyze lovastatin into monacolin J; and to then use an acyl group from the acyl thioester to regioselectively acylate the C8 hydroxyl group of monacolin J; so that simvastatin is made. In certain embodiments, the simvastatin is made in vitro in the absence of an isolated organism.

As is discussed in detail below, the methods and materials of the invention that are used to make simvastatin can be adapted to produce compounds that are structurally similar to simvastatin, for example huvastatin. In this context, one embodiment of the invention is a method of making huvastatin comprising the steps of combining together hydrolyzed pravastatin tetra-ol; an acyl thioester that donates an acyl moiety to the C8 hydroxyl group of hydrolyzed pravastatin tetra-ol in the presence of LovD acyltransferase; and LovD acyltransferase; and then allowing the LovD acyltransferase use an acyl group from the acyl thioester to regioselectively acylate the C8 hydroxyl group of hydrolyzed pravastatin tetra-ol, so that huvastatin is made. A related embodiment of the invention is a composition of matter comprising: hydrolyzed pravastatin tetra-ol; an acyl thioester that donates an acyl moiety to the C8 hydroxyl group of hydrolyzed pravastatin tetra-ol in the presence LovD acyltransferase; LovD acyltransferase; and huvastatin. Consequently, embodiments of the invention include processes for making simvastatin or huvastatin composition of matter substantially as herein disclosed and exemplified.

In some embodiments of the invention, the monacolin J; the acyl thioester and the LovD acyltransferase are combined in a fermentation media in the presence of an isolated organism that produces the LovD acyltransferase and further wherein the organism is *Escherichia Aspergillus terreus, Monascus ruber, Monascus purpureus, Monascus pilosus, Monascus vitreus, Monascus pubigerus, Candida cariosilognicola, Aspergillus ogea, Doratomyces stemonitis, Paecilomyces virioti, Penicillum citrinum, Penicillin chgsogenum, Scopulariopsis brevicaulis* or *Trichoderma viride.* Optionally, the isolated organism is *Aspergillus terreus* that expresses LovD polypeptide of SEQ ID NO: 1. In certain embodiments, the *Aspergillus terreus* does not express LovF polypeptide of SEQ ID NO: 3. Alternatively, the organism can be *Escherichia coli* that expresses LovD polypeptide of SEQ ID NO: 1 or SEQ ID NO: 2. In certain embodiments, the *Escherichia coli* does not express bioH polypeptide of SEQ ID NO: 4. As discussed in detail below, the isolated organism can be grown under one of a variety of fermentation conditions known in the art and the exact conditions can be selected for example based upon the fermentation requirements of specific organism used. In typical embodiments of the invention, the organism is grown at a temperature between 30-40° C., for a time period between at least 4 to at least 48 hours and at a pH between 6.5-8.5. In illustrative embodiments, the organism is grown in a fermentation media comprising LB, F1 or TB media.

Optionally, the monacolin J that is combined with the other constituents in the methods of the invention is produced by an isolated organism within the fermentation media, for example one of the organisms listed above that also produces the LovD acyltransferase. Alternatively, the monacolin J that is combined with the other constituents in the methods of the invention is produced by a different organism that produces this compound that is added to the fermentation media and grows along with the organism that produces the LovD acyltransferase. In this context a number of organisms known in the art to produce monacolin J can be adapted for use with these embodiments of the invention (see, e.g. Endo et al., J Antibiot (Tokyo). 1985 March; 38(3):420-2. And Kennedy et al., 1999 May 21; 284(5418): 1368-72). In another embodiment of the invention, monacolin J is derived from an alternative exogenous source (e.g. a chemical synthesis process) and added to the fermentation mixture.

In typical embodiments of the invention, acyl thioester that can donate an acyl moiety to the C8 hydroxyl group of monacolin J in the presence of LovD acyltransferase is derived from an exogenous source (e.g. a chemical synthesis process) and added to the fermentation mixture. A variety of such acyl thioesters are disclosed herein. Typically the acyl thioester is a butyrlyl-thioester, a N-acetylcysteamine thioester or a methyl-thioglycolate thioester. Optionally, the acyl thioester comprises medium chain length (C3-C6) acyl group moieties. In certain embodiments of the invention, the acyl thioester is able to cross the cellular membranes of *Escherichia coli* or *Aspergillus terreus* cells growing within a fermentation media. Typically, the acyl thioester is selected from the group consisting of α-dimethylbutyryl-S-methyl-mercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB). In an illustrative embodiment, the acyl thioester is α-dimethylbutyryl-S-methyl-mercaptopropionate that is combined in fermentation media in a concentration range of 1 mM-100 mM.

In certain embodiments of the invention, the method results in at least 95%, 96%, 97%, 98% or 99% of the monacolin J added to the combination being converted to simvastatin. Optionally, the method of the invention produces a composition of matter comprising 0%-1% of the monacolin J that was initially added to the combination.

Certain embodiments of the methods for making simvastatin and related compounds include further steps to purify these compounds. For example, embodiments of the invention can include at least one purification step comprising lysis of cells of an isolated organism present in the combination. Embodiments can also include at least one purification step comprising centrifugation of cells or cell lysates of an isolated organism present in the combination. Moreover, embodiments can include at least one purification step comprising precipitation of one or more compounds present in the combination. One embodiment of a precipitation step comprises the precipitation of a free acid form of simvastatin. Optionally in such embodiments, one can then convert this free acid form of simvastatin to a simvastatin salt. Embodiments of the invention can also include at least one purification step comprising filtration of one or more compounds present in the combination. In addition, embodiments can include at least one purification step comprising a high performance liquid chromatography (HPLC) analysis of one or more compounds present in the combination.

Embodiments of the invention include compositions of matter useful for making and/or made by the processes disclosed herein. For example, one embodiment of the invention is a composition of matter comprising: monacolin J; an acyl thioester that donates an acyl moiety to the C8 hydroxyl group of monacolin J in the presence LovD acyltransferase; LovD acyltransferase; and simvastatin. Optionally, the composition further comprises an isolated organism such as *Escherichia coli*, *Aspergillus terreus*, *Monascus ruber*, *Monascus purpureus*, *Monascus pilosus*, *Monascus vitreus*, *Monascus pubigerus*, *Candida cariosilognicola*, *Aspergillus ogea*, *Doratomyces stemonitis*, *Paecilomyces virion*, *Penicillum citrinum*, *Penicillin chysogenum*, *Scopulariopsis brevicaulis* or *Trichoderma virioti*. In typical embodiments, the organism in the composition is *Aspergillus terreus* or *Escherichia coli* that expresses LovD polypeptide of SEQ ID NO:1. In one embodiment of the invention, the organism is *Aspergillus terreus* that does not express LovF polypeptide of SEQ ID NO: 3. In another embodiment of the invention, the organism is *Escherichia coli* that does not express bioH polypeptide of SEQ ID NO: 4. In certain embodiments of the invention, isolated organism within the composition has been transduced with an expression vector encoding *Aspergillus terreus* LovD (SEQ ID NO: 1).

A variety of acyl thioesters that can be used in the compositions of the invention are disclosed herein. Typically the acyl thioester is a butyrlyl-thioester, a N-acetylcysteamine thioester or a methyl-thioglycolate thioester. Optionally, the acyl thioester comprises medium chain length (C3-C6) acyl group moieties. In certain embodiments of the invention, the acyl thioester is able to cross the cellular membranes of *Escherichia coli* or *Aspergillus terreus* cells growing within a fermentation media. Typically, the acyl thioester is selected from the group consisting of α-dimethylbutyryl-S-methyl-mercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB). In an illustrative embodiment, the acyl thioester is α-dimethylbutyryl-S-methyl-mercaptopropionate that is combined in fermentation media in a concentration range of 1 mM-100 mM. In some embodiments of the invention, the composition further comprises lovastatin and the amount of simvastatin in the composition is greater than the amount of lovastatin in the composition.

In certain embodiments of the invention, further components and/or methodological steps can be combined with one or more of the methods and materials discussed above. For example, the methods can further comprise using high cell-density fermentation to increase the effective concentration of LovD acyltransferase and optimise fermentation conditions or increasing LovD acyltransferase catalytic efficiencies towards the one or more thioesters protein engineering. Many other components or methods can be used to increase the production of simvastatin or of an intermediary or related compound that facilitates the production of simvastatin.

Embodiments of the invention also include articles of manufacture and/or kits designed to facilitate the methods of the invention. Typically such kits include instructions for using the elements therein according to the methods of the present invention. Such kits can comprise a carrier means being compartmentalized to receive in close confinement one or more container means such as vials, tubes, and the like, each of the container means comprising one of the separate elements to be used in the method. One of the containers can comprise a vial, for example, containing LovD acyltransferase and/or *A. terreus* and another vial containing an thioester compound or the like, both of which can be added to a fermentation mixture to produce simvastatin and/or huvastatin or the like.

Additional embodiments of the invention are discussed below.

BRIEF DESCRIPTION OF THE DRAWINGS

FIG. 11 encompasses embodiments of the invention including compositions of matter that produces huvastatin or simvastatin in the presence of LovD and an acyl donor. FIG. 11 also illustrates a method of producing simvastatin comprising hydrolyzing lovastatin in the presence of LovD to produce monacolin J. Monacolin J is thereby converted to simvastatin in the presence of an acyl donor. Likewise, FIG. 11 also illustrates a method of producing huvastatin comprising hydrolyzing pravastatin in the presence of LovD to produce hydrolyzed pravastatin. Hydrolyzed pravastatin is thereby converted to huvastatin in the presence of an acyl donor.

FIG. 12 provides illustrations of embodiments of the invention including the production of huvastatin in an organism expressing LovD.

(FIG. 19B) Michaelis-menten kinetics of LovD as a function of DMB-S-MMP concentration, at a fixed monacolin J concentration of 2 mM. Km (DMB-S-MMP)=0.67±0.04 mM. In both assays, the kcat is estimated to be 0.66±0.03 min-1.

(FIG. 20A) HPLC traces of the time course study. The labeled peaks are 1: monacolin J (lactonized form); 2: DMB-S-MPA as a result of DMB-S-MMP hydrolysis; 3: DMB-S-MMP; and 4: simvastatin (lactonized form). (FIG. 20B) Conversion of monacolin J to simvastatin as a function of time. Final conversion at 24 hours was 99%. The data points are averaged values of two runs.

(FIG. 21A) Fed-batch fermentation (500 mL) with F1 minimal medium. At OD600 (circles) of 5.93 (I), the temperature of the fermentation is decreased to and maintained at RT. IPTG is added to a final concentration of 200 μM and the feeding is initiated and maintained at 0.08 mL/min. The effective concentrations of LovD at different points of the fermentation are measured (squares). (FIG. 21B) The rate of conversion of monacolin J to simvastatin by cells at four different points during the fermentation (indicated by 1, 2, 3 and 4) in FIG. 21A. The cells are either made "resting" by shifting to 50 mM HEPES, pH 7.9, or "non-resting" without medium change.

DETAILED DESCRIPTION OF THE INVENTION

The techniques and procedures described or referenced herein are generally well understood and commonly employed using conventional methodology by those skilled in the art, such as, for example, the widely utilized molecular cloning methodologies described in Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted. Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

The definitions of certain terms are provided below.

"Lovastatin" (Mevacor) is a fungal polyketide produced by *Aspergillus terreus* (see, e.g., A. W. Alberts, J. et. al., *Proc. Natl. Acad. Sci. U.S.A*, 1980, 77, 3957-3961 and A. Endo, *J. Antibiot.* 1980, 33, 334-336; and J. K. Chan, et. al., *J. Am. Chem. Soc.* 1983, 105, 3334-3336; Y. Yoshizawa, et. al., *J. Am. Chem. Soc.* 1994, 116, 2693-2694). It is a pharmaceutically important compound because of its potent inhibitory activities towards hydroxymethylglutaryl coenzyme A reductase (HMGR), the rate-limiting step of cholesterol biosynthesis, and therefore it is widely used in the treatment of hyperlipidemia, hypercholesterolemia, and the like. Lovastatin is also referred to as Mevacor.

Figures 1A, 1B:
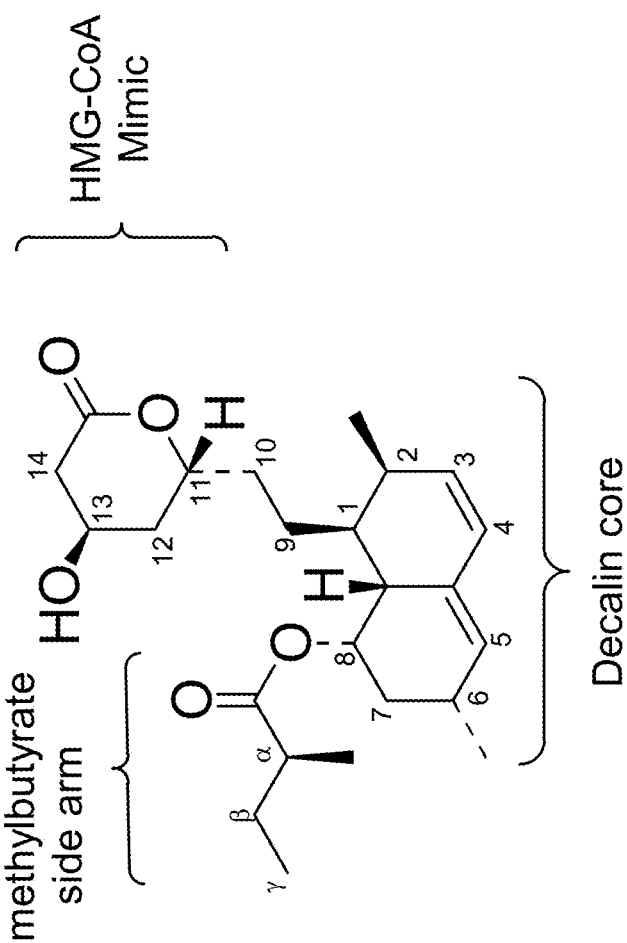
FIG. 1. A. Lovastatin. B. Simvastatin. The two compounds differ by one methyl substitution at the α position.
Figure 2:
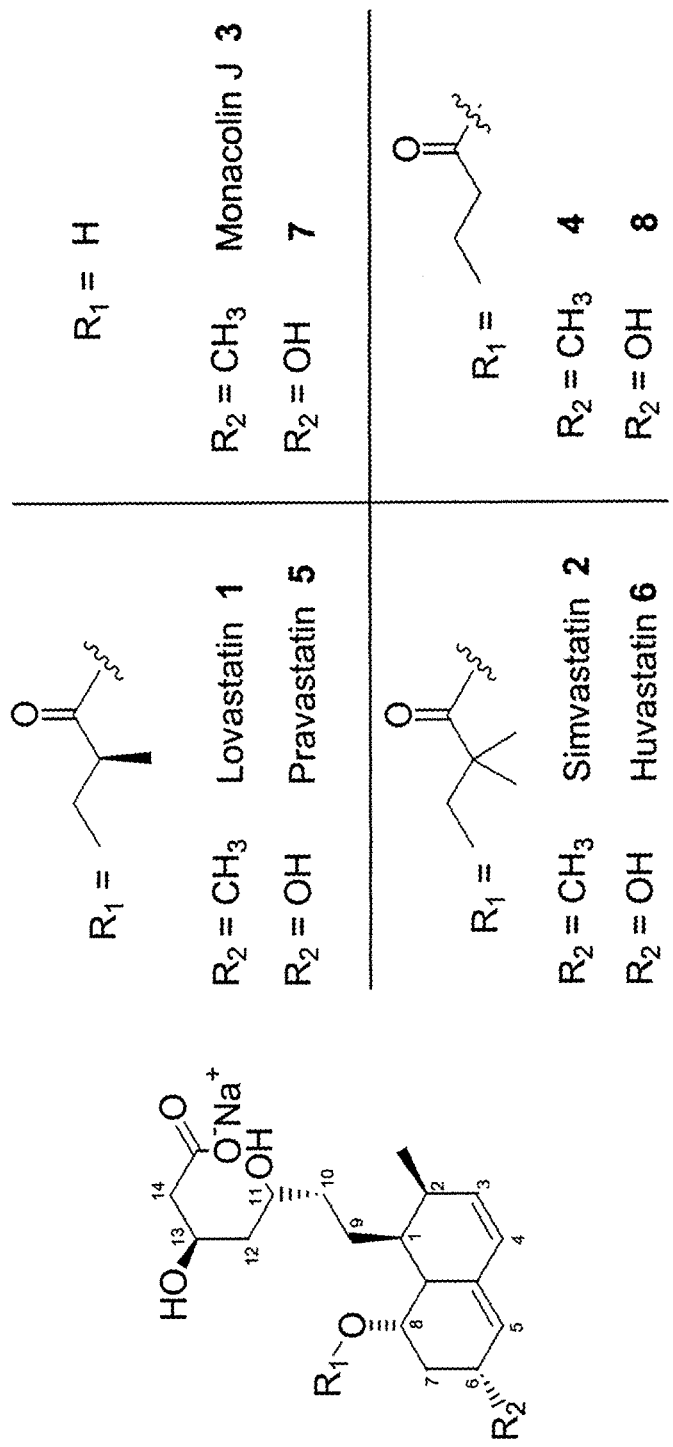
FIG. 2. Lovastatin (1), Simvastatin (2), Pravastatin (5), Huvastatin (6) and related compounds FIG. 3. Current method of manufacturing simvastatin.
Figure 3:
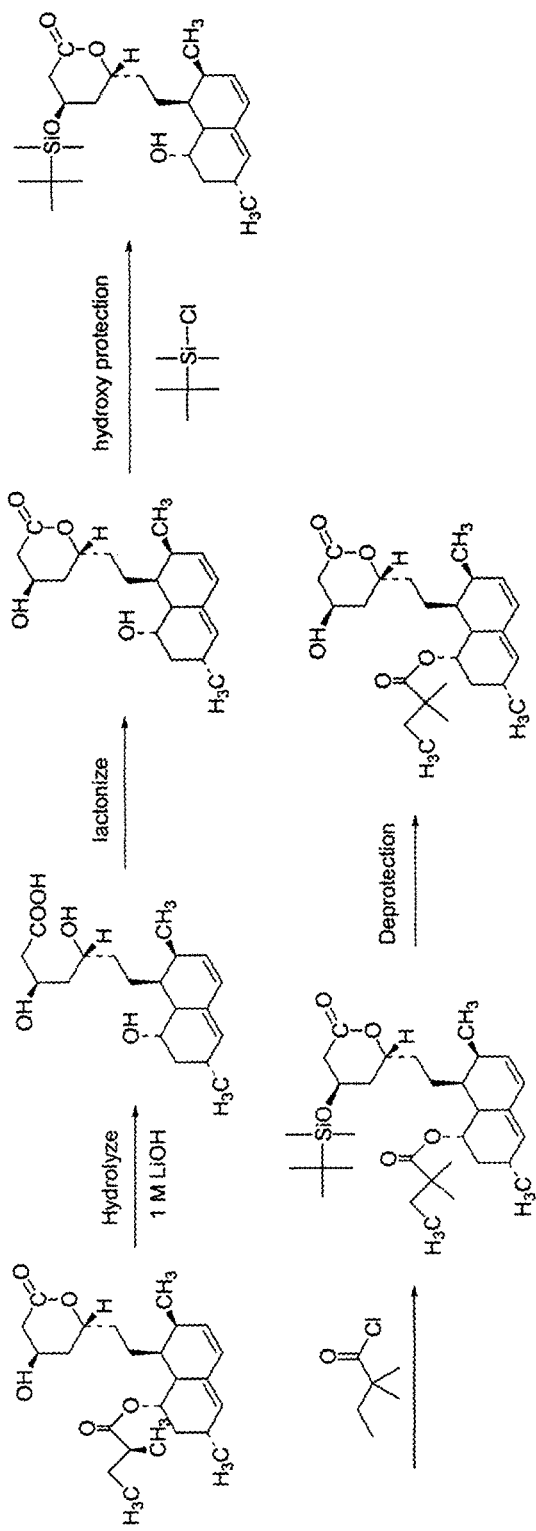

"Simvastatin" is an analog of lovastatin. It is favored over lovastatin because of the absence of adverse side effects and its high absorbability in the stomach. Also, it has been reported that simvastatin prevents and reduces the risk of Alzheimer's disease (AD) by retarding the production of Ab42, β-amyloid protein associated with AD. It is known in the art that simvastatin can be synthetically prepared by way of direct methylation of the 8'-methylbutyryloxy side chain of lovastatin of formula using a methyl halide in the presence of a metal amide base. The C-methylation step has to be carried out at extremely low temperatures (−75 to −30°) using a strong base under anhydrous condition which is difficult to handle in mass production (see, e.g., U.S. Pat. Nos. 5,393,893, 4,582,915, 5,763,646, 5,763,653, EP Patent No. 299,656 and International Patent Publication No. WO 99/45003, the contents of which are herein incorporated by reference). Other methods of synthetically producing simvastatin is also known in the art. For example, lovastatin can be hydrolyzed with an excessive amount of lithium hydroxide to remove the 2-methylbutyryl side chain and to simultaneously open its 6-membered lactone ring to produce a triol acid. The triol acid compound can then be heated to obtain a diol lactone. The hydroxy group on the lactone ring of the diol lactone can be protected to obtain a tert-butyldimethylsilyl ether and then the hydroxy group at C8 of the hexahydronaphthalene ring system can be acylated with 2,2-dimethylbutanoic acid in the presence of dicyclohexyl carbodiimide, or 2,2-dimethyl chloride to produce a compound. The t-butyldimethylsilyl protecting group of the compound can then be removed in the final step using tetrabutylammonium fluoride to produce simvastatin (see, e.g., U.S. Pat. No. 4,444,784, the contents of which are herein incorporated by reference). "Lovastatin derivatives" as used herein comprises lovastatin derivatives or precursors for example pravastatin, huvastatin, simvastatin, or hydrolyzed pravastatin tetra-ol. "Monacolin J variants" refers to monacolin J variants disclosed in the art, for example hydrolyzed pravastatin tetra-ol or 6-hydroxyl-6-desmethyl-monacolin J and the like. In certain embodiments of the invention, "Monacolin J variants" refers to Monacolin J compounds having substitutions at the C6 position in FIG. 2. In describing compounds such as simvastatin, pravastatin, monacolin J and variants etc., those of skill in the art understand that this language is intended to encompass these compounds as well as the salts of these compounds (e.g. pharmaceutically acceptable salts known in the art). For example, as is known in the art, simvastatin can occur both a free acid form as well as a simvastatin sodium, potassium or ammonium salts, and other salts derived from alkaline earth elements or other metallic salts.

"*Aspergillus terreus*" or "*A. terreus*" is a filamentous ascomycete commonly found in soil. A variety of *A. terreus* strains are know in the art, for example those deposited as, e.g., ATCC 20542 and ATCC 20541.

As is known in the art, genes related to biosynthesis of secondary metabolites of filamentous fungi can form a cluster on the fungal genome and are referred to as "gene clusters." For example, "Lovastatin-producing gene cluster" can refer to a set of genes that produce lovastatin, the set of genes comprising, LovA, a P450I; LovC, a dehydrogenase; LovD, an esterase and acyltransferase; and LovF, a ScPKS or LDKS. It has been determined previously that each of these four genes (LovA, LovC, LovD, and LovF) is required for lovastatin synthesis (see, e.g., U.S. Pat. No. 6,943,017, the contents of which are herein incorporated by reference). LovF (LDKS gene) is characterized as a polyketide synthase gene. LovD is a putative esterase/carboxypeptidase-like gene. Disruption of the LovF gene has been done previously (see, e.g., U.S. Pat. No. 6,943,017, the contents of which are herein incorporated by reference). LovD interacts with LovF to produce lovastatin; however, the LovD-LovF interaction is not required for the production of simvastatin. Moreover, another gene in the lovastatin-producing gene cluster is LovE, which is a Zn finger that can regulate the transcription of the other genes. The lovastatin-producing gene cluster also comprises LovB (NPKS gene).

"LDKS" or "LDKS gene" refers to the protein encoded by the LovF gene, a member of the lovastatin-producing gene cluster. LDKS stands for lovastatin diketide synthase. LovF is the gene that produces LDKS. LovF is also the gene that produces LovF protein. "LDKS gene" also refers to the gene that produces LDKS. In the synthesis of lovastatin, LDKS synthesizes the five carbon unit side chain of monacolin J through condensation between an acetyl-CoA and a malonyl-CoA. The condensed diketide undergoes methylation and reductive tailoring by the individual LovF domains to yield an α-S-methylbutyryl thioester covalently attached to the phosphopantetheine arm on the acyl carrier protein (ACP) domain of LovF.

"LovD acyltransferase" as used herein refers to those polypeptides such as the *A. terreus* LovD polypeptide (e.g. SEQ ID NO: 1) that can use a acyl thioester to regiospecifically acylate the C8 hydroxyl group of monacolin J so as to produce simvastatin. As also disclosed herein, this LovD enzyme can further utilize a acyl thioester to regiospecifically acylate the C8 hydroxyl group of hydrolyzed pravastatin tetra-ol so as to produce huvastatin.

LovD acyltransferases include homologous enzymes to *A. terreus* LovD polypeptide (e.g. SEQ ID NO: 1) that can be found in for example, but not limited to, fungal polyketide gene clusters. For example, the art provides evidence that Mlc in the compactin biosynthetic pathway catalyzes the identical transacylation reaction (see, e.g., Y. Abe, T. et. al., *Mol Genet Genomics.* 2002, 267, 636-646), whereas an acyltransferase in the squalestatin pathway can catalyze a similar reaction between an ACP-bound tetraketide thioester and an aglycon (see, e.g., R. J. Cox, F. et. al., *Chem Commun*

(*Camb*) 2004, 20, 2260-2261). The amino acid sequence of *A. terreus* LovD polypeptide (e.g. SEQ ID NO: 1) resembles type C β-lactamase enzymes, which catalyze the hydrolytic inactivation of the β-lactam class of antibiotics (see., e.g., E. Lobkovsky, E. M. et. al., *Biochemistry,* 1994, 33, 6762-6772 and A. Dubus, D. et. al., *Biochem. J.* 1993, 292, 537-543). Alignment of *A. terreus* LovD polypeptide (e.g. SEQ ID NO: 1) with the *Enterobacter cloacae* P99 lactamse (see, e.g., S. D. Goldberg, et. al., *Protein Sci.* 2003, 12, 1633-1645) shows moderate sequence homology, including potentially conserved active site residues, such as the catalytic Ser76, Lys79, Tyr188, and Lys315 (see. e.g. S. D. Goldberg, et. al., *Protein Sci.* 2003, 12, 1633-1645).

LovD acyltransferases can also refer to both genetically engineered and naturally occurring enzymes that are related to *A. terreus* LovD polypeptide (e.g. SEQ ID NO: 1) in sequence but containing slight amino acid differences (e.g. 1-10 amino acid substitution mutations). Simvastatin, for example, can be produced from naturally occurring enzymes that are similar to *A. terreus* LovD polypeptide (e.g. SEQ ID NO: 1) in sequence (e.g. the MlCH from the compactin cluster). "LovD acyltransferases" can also refer to mutants of *A. terreus* LovD polypeptide (SEQ ID NO: 1). It is known in the art that mutants can be created by standard molecular biology techniques to produce, for example, mutants of SEQ ID NO: 1 that improve catalytic efficiencies or the like. For example, we are currently using rational and directed evolution approaches to improve the catalytic turnover rates of *A. terreus* LovD. Typically such mutants will have a 50%-99% sequence similarity to SEQ ID NO: 1. In this context, the term "LovD homologous enzyme" includes a LovD polypeptide having at least 80%, 85%, 90%, 95%, 97%, 98% or 99% sequence identity with the amino acid sequence set out in SEQ ID NO: 1, wherein the polypeptide has the ability to utilize a acyl thioester to regiospecifically acylate the C8 hydroxyl group of monacolin J so as to produce simvastatin and/or utilize a acyl thioester to regiospecifically acylate the C8 hydroxyl group of hydrolyzed pravastatin tetra-ol so as to produce huvastatin. Such mutants are readily made and then identified in assays which observe the production of a desired compound such as simvastatin (typically using *A. terreus* LovD polypeptide (e.g. SEQ ID NO: 1) as a control). These mutants can be used by the methods of this invention to make simvastatin or huvastatin, for example.

"Heterologous" as it relates to nucleic acid sequences such as coding sequences and control sequences denotes sequences that are not normally associated with a region of a recombinant construct, and/or are not normally associated with a particular cell. Thus, a "heterologous" region of a nucleic acid construct can be an identifiable segment of nucleic acid within or attached to another nucleic acid molecule that is not found in association with the other molecule in nature. For example, a heterologous region of a construct can include a coding sequence flanked by sequences not found in association with the coding sequence in nature. Similarly, a host cell transformed with a construct, which is not normally present in the host cell, would be considered heterologous (see, e.g., U.S. Pat. Nos. 5,712,146 6,558,942, 6,627,427, 5,849,541 the contents of which are herein incorporated by reference). For instance, a construct with Lov genes can be isolated and expressed in non-lovastatin producing fungi or yeast host cells, and lovastatin can thereby be produced (see, e.g., U.S. Pat. Nos. 6,391,583 and 6,943,017, the contents of which are herein incorporated by reference). As another example, prokaryotes such as bacteria can be host cells also, as is known in the art. Fungal genes may also be cloned into an expression vector for expression in prokaryotes (see, e.g., U.S. Pat. No. 5,849,541, the contents of which are herein incorporated by reference).

A prokaryote such as *E. coli* can be used as a heterologous host. A plasmid can be constructed with a gene of interest and the plasmid can be transformed into *E. coli*. The gene of interest can be translated and the protein derived from the gene of interest can be purified thereafter. This method of expression and protein purification is known in the art. For example, LovD exons from *A. terreus* can be individually amplified from the genomic DNA of *A. terreus* and spliced to yield a continuous open reading frame using splice overlap extension PCR. Restriction sites can be introduced, and the gene cassette can be ligated to a vector to yield an expression construct that can be transformed into *E. coli*. Thereby, *E. coli* can be used as a heterologous host for expression of *A. terreus* genes. *E. coli* can be co-cultured with another strain that produces another substrate of interest. Additionally, substrates can be added to this culture or co-culture. Heterologous expression of the lovastatin biosynthesis genes is known in the art (see, e.g., U.S. Pat. Nos. 6,391,583 and 6,943,017, the contents of which are herein incorporated by reference).

As another example, certain polyketides, such as polyketides from fungi, or other organisms, can be heterologously expressed in *E. coli*, yeast, and other host organisms. These host organisms can be supplemented with other substrates, since they can require both the heterologous expression of a desired PKS and also the enzymes that produce at least some of the substrate molecules required by the PKS (see, e.g., U.S. Pat. No. 7,011,959, the contents of which are herein incorporated by reference). Similarly, fungal Lov genes can be expressed in *E. coli* or other bacterium, and these host bacteria can be supplemented with other substrates, such as acyl-SNAC or other acyl donor groups. These acyl donor groups can be cell permeable, and enter the bacterial cell.

"Expression vector" refers to a nucleic acid that can be introduced into a host cell. As is known in the art, an expression vector can be maintained permanently or transiently in a cell, whether as part of the chromosomal or other DNA in the cell or in any cellular compartment, such as a replicating vector in the cytoplasm. An expression vector also comprises a promoter that drives expression of an RNA, which typically is translated into a polypeptide in the cell or cell extract. For example, suitable promoters for inclusion in the expression vectors of the invention include those that function in eukaryotic or prokaryotic host cells. Promoters can comprise regulatory sequences that allow for regulation of expression relative to the growth of the host cell or that cause the expression of a gene to be turned on or off in response to a chemical or physical stimulus. For *E. coli* and certain other bacterial host cells, promoters derived from genes for biosynthetic enzymes, antibiotic-resistance conferring enzymes, and phage proteins can be used and include, for example, the galactose, lactose (lac), maltose, tryptophan (trp), beta-lactamase (b/a), bacteriophage lambda PL, and T5 promoters. In addition, synthetic promoters, such as the tac promoter (U.S. Pat. No. 4,551,433), can also be used. For *E. coli* expression vectors, it is useful to include an *E. coli* origin of replication, such as from pUC, p1P, p1I, and pBR. For efficient translation of RNA into protein, the expression vector also typically contains a ribosome-binding site sequence positioned upstream of the start codon of the coding sequence of the gene to be expressed. Other elements, such as enhancers, secretion signal sequences, transcription termination sequences, and one or more marker genes by which host cells containing the vector can be identified and/or selected, may also be present in an expression vector. Selectable markers, i.e., genes that confer antibiotic resistance or sensitivity, can be used and confer a selectable phenotype on transformed cells when the cells are grown in an appropriate selective medium. For example, an expression vector containing the Lov gene cluster or portions thereof can be introduced into a heterologous host, such as *E. coli*. Thus, recombinant expression vectors can contain at least one expression system, which, in turn, can be composed of at least a portion of Lov and/or other biosynthetic gene coding sequences operably linked to a promoter and optionally termination sequences that operate to effect expression of the coding sequence in compatible host cells.

A "coding sequence" can be a sequence which "encodes" a particular gene, such as a gene from the Lov gene cluster, for example. A coding sequence is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence will usually be located 3' to the coding sequence.

DNA "control sequences" refer collectively to promoter sequences, ribosome binding sites, polyadenylation signals, transcription termination sequences, upstream regulatory domains, enhancers, and the like, which collectively provide for the transcription and translation of a coding sequence in a host cell.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof.

"Lovastatin-producing organism" refers to the wide variety of different organisms known in the art to produce lovastatin. These organisms that produce lovastatin can modified to produce simvastatin by the methods of this invention. *A. terreus* is an example of a lovastatin producing organism. Microorganisms other than *A. terreus* reported to produce lovastatin (mevinolin) include *Monascus* species, for example *M. ruber, M. purpureus, M. pilosus, M. vitreus, M. pubigerus*, as well as *Penicillium, Hypomyces, Doratomyces, Phoma, Eupenicillium, Gymnoascus*, and *Trichoderma* species, *Pichia labacensis, Candida cariosilognicola, Aspergillus ogea, Doratomyces stemonitis, Paecilomyces virioti, Penicillum citrinum, Penicillin chysogenum, Scopulariopsis brevicaulis* and *Trichoderma viride* (see, e.g., U.S. Pat. No. 6,391,583; Juzlova et al., J. Ind. Microbiol. 16:163-170; Gunde-Cimerman et al., FEMS Microbiol. Lett. 132:39-43 (1995); and Shindia et al., Folio Microbiol. 42:477-480 (1997), the contents of which are herein incorporated by reference).

"Non-lovastatin-producing organisms" as used herein refers to a number organisms that do not produce lovastatin absent manipulation by man (e.g. *E. Coli*). These organisms can be induced to produce LovD, or cultured in the presence of LovD to produce lovastatin or simvastatin by the methods of this invention, for example.

"*A. terreus* having a disruption in the LDKS gene" comprises an *A. terreus* without the LDKS gene, having a LDKS gene that is mutated, having a LDKS gene that is knocked-out, having a LDKS gene that is deleted, having a LDKS gene whose expression is disrupted, or having a LDKS gene that is disrupted. "*A. terreus* having a disruption in the LDKS gene" comprises an *A. terreus* having a LDKS gene that is silenced by methods known in the art. "*A. terreus* having a disruption in the LDKS gene" refers to an *A. terreus* that cannot produce functional LDKS. "*A. terreus* having a disruption in the LDKS gene" can also refer to an *A. terreus* that produces functional LDKS. The LDKS can be inactivated or inhibited by methods known in the art such as gene knock out protocols. The amount of LDKS present can be reduced by methods known in the art. Other methods of inhibition, inactivation, or disruption of LDKS gene or protein include, but or not limited to, antisense, siRNA, RNAi, or RNA interference as is known in the art. "LDKS gene" as used herein can also refer to the LovF gene. Disruption of the LovF gene is known in the art (see, e.g., U.S. Pat. No. 6,391,583 the contents of which are herein incorporated by reference. "*A. terreus* having a disruption in the LDKS gene" is typically a genetically manipulated organism. Genetic manipulation of *A. terreus* is known in the art. Gene disruption of the Lov genes in *A. terreus* has been done previously (see, e.g., U.S. Pat. Nos. 6,391,583 and 6,943,017, the contents of which are herein incorporated by reference). Disruption of specifically the LovF gene (producing LDKS) in *A. terreus* has been done previously (see, e.g., U.S. Pat. No. 6,943,017, the contents of which are herein incorporated by reference). Disruption of the LovF gene can occur by other methods as is known in the art. *A. terreus* having a disruption in the LDKS gene can be in a fermentation mixture. Substrates can be added to the fermentation mixture of an *A. terreus* having a disruption in the LDKS gene to produce lovastatin analogs.

"A component or method to increase the production of simvastatin" as used herein refers to a compound or substrate, synthetic or natural, that increases the production of certain intermediaries to increase the amount of simvastatin produced for scale-up and large-scale synthesis of simvastatin. Components and methods for increasing the production of certain intermediaries are known in the art. For example, compounds that are added to the fermentation mixture to increase the amount of intermediaries, such as monacolin J, in the production of lovastatin are known in the art (see, e.g., U.S. Pat. No. 6,943,017, the contents of which are herein incorporated by reference). Some of these intermediaries, such as monacolin J, can also be used in the production of simvastatin. Compounds for increasing the production of monacolin J thereby can be added to increase the production of simvastatin. For example, compounds for increasing the production of monacolin J can be directly added to the fermentation mixture to increase the amount of simvastatin produced. An example of a component for increasing the production of simvastatin is a clone containing the D4B segment of the lovastatin producing gene cluster that is deposited in ATCC accession number 98876. This clone can be transformed into a non-lovastatin producing organism to produce monacolin J as is known in the art. This clone can also be transformed into a lovastatin-producing organism to increase the production of monacolin J and thereby increase the production of simvastatin. Moreover, another example of a component for increasing the production of simvastatin is the LovE/zinc finger gene, which can be transformed into a lovastatin-producing organism to increase the production of simvastatin. Preferably, this lovastatin-producing organism would have a disruption in the LDKS gene (see, e.g., U.S. Pat. No. 6,391,583, the contents of which are herein incorporated by reference). Components and methods to increase the production of simvastatin can refer to many others and are not limited to the examples listed above.

As disclosed herein, an ""Acyl donor" or "acyl carrier" is a compound having an acyl group that can be transferred to simvastatin and/or a simvastatin precursor or a related compound. Typically, ""Acyl donor" or "acyl carrier" is an acyl thioester that donates an acyl moiety to the C8 hydroxyl group of monacolin J. A wide variety of such agents are known in the art that are further shown herein to have this activity (see, e.g. the illustrative acyl-thioesters in Table 1). In addition to those known in the art and further shown by the instant disclosure to have this activity, any potential acyl donor/carrier known in the art (or synthesized de novo) having an ability to acylate C8 of monacolin J so as to produce simvastatin can be easily identified by comparative experiments with the acyl donors disclosed herein (e.g. acyl-SNAC). As is known in the art, an acyl group can have the formula RCON; wherein R can be an alkyl or aryl and N can be —Cl, —OOCR, —NH2, —OR, or the like. Compounds that have an acyl group includes, but is not limited to, acid chlorides, esters, amides, or anhydrides and the like. These compounds can be aliphatic or aromatic, substituted or unsubstituted. Examples include, but are not limited to, benzoyl chloride, benzoic anhydride, benzamide, or ethyl benzoate, and the like. Other examples of acyl donors include, but are not limited to, α-dimethylbutyrl-SNAC, acyl-thioesters, acyl-CoA, butyryl-CoA, benzoyl-CoA, acetoacetyl-CoA, β-hydroxylbutyryl-CoA, malonyl-CoA, palmitoyal-CoA, butyryl-thioesters, N-acetylcyteamine thioesters (SNAC), methyl-thioglycolate (SMTG), benzoyl-SNAC, benzoyl-SMTG, or α-S-methyl-butyryl-SNAC. These compounds can be produced naturally or synthetically, and, in some cases, can penetrate the cell membrane. A number of these compounds can be added to LovD in the presence of monacolin J to produce simvastatin for example.

"Acyl-SNAC" as used herein refers to α-dimethylbutyrl-SNAC. As is known in the art, acyl-SNAC can penetrate the cell membrane under in vivo conditions. LovD can use acyl-SNAC as a substrate to initiate the reaction from monacolin J to simvastatin by regiospecifically acylating the C8 hydroxyl group of monacolin J. Acyl-SNAC can donate its acyl group to LovD.

Typical Embodiments of the Invention

Those of skill in the art will understand that the disclosure provided herein allows artisans to produce a wide variety of embodiments of the invention. A typical embodiment of the invention is a method of making simvastatin by combining together monacolin J; an acyl thioester that donates an acyl moiety to the C8 hydroxyl group of monacolin J in the presence of LovD acyltransferase; and LovD acyltransferase; and then allowing the LovD acyltransferase use an acyl group from the acyl thioester to regioselectively acylate the C8 hydroxyl group of monacolin J; so that simvastatin is made. In illustrative embodiments of the invention, the LovD acyltransferase has the amino acid sequence of SEQ ID NO: 1 or SEQ ID NO: 2. A related embodiment of the invention is a method of making simvastatin comprising the steps of combining together lovastatin; an acyl thioester that donates an acyl moiety to the C8 hydroxyl group of monacolin J in the presence of LovD acyltransferase; and LovD acyltransferase. In this related method, the LovD acyltransferase is then allowed to hydrolyze lovastatin into monacolin J; and to then use an acyl group from the acyl thioester to regioselectively acylate the C8 hydroxyl group of monacolin J; so that simvastatin is made. In certain embodiments, the simvastatin is made in vitro in the absence of an isolated organism.

In some embodiments of the invention, the monacolin J; the acyl thioester and the LovD acyltransferase are combined in a fermentation media in the presence of an isolated organism that produces the LovD acyltransferase and further wherein the organism is Escherichia coli, Aspergillus terreus, Monascus ruber, Monascus purpureus, Monascus pilosus, Monascus vitreus, Monascus pubigerus, Candida cariosilognicola, Aspergillus ogea, Doratomyces stemonitis, Paecilomyces virioti, Penicillum citrinum, Penicillin chgsogenum, Scopulariopsis brevicaulis or Trichoderma viride. Optionally, the isolated organism is Aspergillus terreus that expresses LovD polypeptide of SEQ ID NO: 1. In certain embodiments, the Aspergillus terreus does not express LovF polypeptide of SEQ ID NO: 3. In certain embodiments of the invention, the expression polypeptides such as those in SEQ ID NOs: 3 and 4 is reduced to at least 90, 95, or 99% of is endogenous activity. Alternatively, the organism can be Escherichia coli that expresses LovD polypeptide of SEQ ID NO: 1. In certain embodiments, the Escherichia coli does not express bioH polypeptide of SEQ ID NO: 4. Consequently, the host can either be one that produces a LovD acyltransferase endogenously or alternatively a heterologous host where the LovD acyltransferase gene has been introduced into the organism, for example, by a cloning technology known in the art and further discussed herein. In a typical embodiment, the heterologous host that expresses LovD acyltransferase is a bacterium, yeast, or fungi that is known in the art to be useful for such purposes.

As discussed in detail below, the isolated organism can be grown under one of a variety of fermentation conditions known in the art and the exact conditions are selected, for example based upon fermentation parameters associated with optimized growth of a specific organism used in an embodiment of the invention (see, e.g. Miyake et al., Biosci. Biotechnol. Biochem., 70(5): 1154-1159 (2006) and Hajjaj et al., Applied and Environmental Microbiology, 67: 2596-2602 (2001), the contents of which are incorporated by reference). Typically, the organism is grown at a temperature between 30-40° C., for a time period between at least 4 to at least 48 hours. Typically, the organisms are grown at a pH between 6.5-8.5. In certain embodiments of the invention, the pH of the fermentation media can be 6.9, 7.0, 7.1, 7.2, 7.3, 7.4, 7.5, 7.6, 7.7, 7.8, 7.9, 8.0 or 8.1. In illustrative embodiments, the organism is grown in a fermentation media comprising LB, F1 or TB media.

Optionally, the monacolin J that is combined with the other constituents in the methods of the invention is produced by an isolated organism within the fermentation media, for example, one of the organisms listed above that also produces the LovD acyltransferase. Alternatively, the monacolin J that is combined with the other constituents in the methods of the invention is produced by a different organism that produces this compound that is added to the fermentation media and grows along with the organism that produces the LovD acyltransferase. In another embodiment of the invention, monacolin J is derived from an exogenous source and added to the fermentation mixture. Optionally, the method of the invention produces a composition of matter comprising 0%-1% of the monacolin J that was initially added to the combination. In certain embodiments of the invention, the method results in at least 95% of the monacolin J added to the combination being converted to simvastatin.

In typical embodiments of the invention, acyl thioester that can donate an acyl moiety to the C8 hydroxyl group of monacolin J in the presence of LovD acyltransferase is derived from an exogenous source (e.g. a chemical synthesis process) and added to the fermentation mixture. A variety of such acyl thioesters are disclosed herein. Typically, the acyl thioester is a butyrlyl-thioester, a N-acetylcysteamine thioester or a methyl-thioglycolate thioester. Optionally, the acyl thioester comprises medium chain length (C3-C6) acyl group moieties. In certain embodiments of the invention, the acyl thioester is able to cross the cellular membranes of Escherichia coli or Aspergillus terreus cells growing within a fermentation media. Typically, the acyl thioester is selected from the group consisting of α-dimethylbutyryl-S-methyl-mercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB). In an illustrative embodiment, the acyl thioester is α-dimethylbutyryl-S-methyl-mercaptopropionate that is combined in fermentation media in a concentration range of 1 mM-100 mM.

Certain embodiments of the methods for making simvastatin include further steps to purify simvastatin by the combination. For example, some embodiments of the invention include at least one purification step comprising lysis of cells of an isolated organism present in the combination. Embodiments can include at least one purification step comprising centrifugation of cells or cell lysates of an isolated organism present in the combination. Embodiments can include at least one purification step comprising precipitation of one or more compounds present in the combination. Embodiments can include at least one purification step comprising filtration of one or more compounds present in the combination. Embodiments can include at least one purification step comprising a high performance liquid chromatography (HPLC) analysis of one or more compounds present in the combination.

The disclosure provided herein shows that variety of permutations of these methods can be used to make simvastatin and huvastatin and the like. In certain embodiments of the invention for example, the host organism produces the acyl thioester and/or the monacolin J. Alternatively, the acyl thioester and/or the monacolin J are added to the organism as part of the process for producing simvastatin. The methods can further comprise adding an expression vector having one or more A. terreus genes that are known to facilitate the production of simvastatin and/or huvastatin or the like such as the genes that encode SEQ ID NO: 1 or SEQ ID NO: 2 and transforming it into the heterologous host, wherein the polypeptide having the acyltransferase activity is thereby expressed. In another embodiment, monacolin J can be produced from a heterologous host.

Another embodiment of the invention is a method of producing simvastatin from monacolin J in an organism which expresses a LovD acyltransferase gene comprising coculturing this first organism that expresses the LovD acyltransferase with a second organism (e.g. in a fermentation mixture) that produces the acyl thioester and/or the monacolin J, wherein the acyl thioester interacts with LovD acyltransferase gene product in the presence of monacolin J to produce simvastatin. Optionally, the first organism is an organism that does not produce lovastatin naturally (e.g. E. coli transduced with the LovD acyltransferase gene). Alternatively, the first organism is a lovastatin-producing organism such as A. terreus (e.g. A. terreus having an inactivated LovF/LDKS gene). The method can further comprise adding one or more exogenous components to the fermentation mixture to increase the production of simvastatin precursors such as monacolin J to thereby increase the production of simvastatin.

The methods of the invention can further comprise adding further components to the fermentation mixture to increase the production of monacolin J and to thereby increase the production of simvastatin and/or huvastatin. As one illustrative embodiment of this method, the component can be a clone with the LovE gene, wherein the organism is transformed with the clone and LovE is translated and thereby the production of simvastatin is increased. As another illustrative embodiment of this method, the component can be a clone containing the D4B segment of the A. terreus genome (ATCC accession 98876), wherein the organism is transformed with the clone so that the production of monacolin J is increased.

Yet another embodiment of the invention is a method of converting monacolin J to simvastatin in vitro or in vivo in the presence of an exogenous acyl thioester. Preferably, the acyl thioester is capable of penetrating the cell membrane. In yet another embodiment of the invention, is a method of converting monacolin J to simvastatin directly within the organism in the presence of the acyl thioester wherein the organism produces LovD. In an illustrative embodiment of the invention, the organism is an A. terreus having a disrupted LDKS gene.

Yet another embodiment of the invention is a simvastatin product made by a process comprising the steps of combining together monacolin J; an acyl thioester that donates an acyl moiety to the C8 hydroxyl group of monacolin J in the presence of LovD acyltransferase; and LovD acyltransferase; and allowing the LovD acyltransferase use an acyl group from the acyl thioester to regioselectively acylate the C8 hydroxyl group of monacolin J so that the simvastatin product is made. A related embodiment of the invention is a huvastatin product made by a process comprising the steps of combining together hydrolyzed pravastatin tetra-ol; an acyl thioester that donates an acyl moiety to the C8 hydroxyl group of hydrolyzed pravastatin tetra-ol in the presence of LovD acyltransferase; and LovD acyltransferase; and allowing the LovD acyltransferase use an acyl group from the acyl thioester to regioselectively acylate the C8 hydroxyl group of hydrolyzed pravastatin tetra-ol; so that the huvastatin product is made.

Another embodiment of the invention is a method of producing simvastatin comprising hydrolyzing lovastatin into monacolin J in the presence of LovD of SEQ ID NO: 1 or a LovD homologue and acylating monacolin J, wherein said hydrolyzation and acylation produce simvastatin. Another related embodiment of the invention is a method of producing huvastatin comprising pravastatin into hydrolyzed pravastatin in the presence of LovD of SEQ ID NO: 1 or a LovD homologue and acylating a monacolin J variant, wherein said hydrolyzation and acylation produce huvastatin.

Embodiments of the invention include composition of matter used to make and or made by the processes disclosed herein. For example, one embodiment of the invention is a composition of matter comprising monacolin J; an acyl thioester that donates an acyl moiety to the C8 hydroxyl group of monacolin J in the presence LovD acyltransferase. Certain embodiments of these compositions of matter further comprise LovD acyltransferase. Certain embodiments of these compositions of matter further comprise simvastatin. Optionally, the composition further comprises an isolated organism such as Escherichia Aspergillus terreus, Monascus ruber, Monascus purpureus, Monascus pilosus, Monascus vitreus, Monascus pubigerus, Candida cariosilognicola, Aspergillus ogea, Doratomyces stemonitis, Paecilomyces virioti, Penicillum citrinum, Penicillin chysogenum, Scopulariopsis brevicaulis or Trichoderma viride. In typical embodiments, the organism in the composition is Aspergillus terreus or Escherichia coli that expresses LovD polypeptide of SEQ ID NO:1. In one embodiment of the invention the organism is Aspergillus terreus that does not express LovF polypeptide of SEQ ID NO: 3. In another embodiment of the invention the organism is Escherichia coli that does not express bioH polypeptide of SEQ ID NO: 4. In certain embodiments of the invention, isolated organism within the composition has been transduced with an expression vector encoding Aspergillus terreus LovD polypeptide of SEQ ID NO: 1.

A variety of acyl thioesters that can be used in the compositions of the invention are disclosed herein. Typically, the acyl thioester is a butyrlyl-thioester, a N-acetylcysteamine thioester or a methyl-thioglycolate thioester. Optionally, the acyl thioester comprises medium chain length (C3-C6) acyl group moieties. In certain embodiments of the invention, the acyl thioester is able to cross the cellular membranes of Escherichia coli or Aspergillus terreus cells growing within a fermentation media. Typically, the acyl thioester is selected from the group consisting of α-dimethylbutyryl-S-methyl-mercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB). In an illustrative embodiment, the acyl thioester is α-dimethylbutyryl-S-methyl-mercaptopropionate that is combined in fermentation media in a concentration range of 1 mM-100 mM and can typically be about 10, 20, 30, 40, 50, 60, 70, 80 or 90 mM. In some embodiments of the invention, the composition further comprises lovastatin and the amount of simvastatin in the composition is greater than the amount of lovastatin in the composition.

As is discussed in detail below, the methods and materials of the invention that are used to make simvastatin can be adapted to produce compounds that are structurally similar to simvastatin, for example huvastatin. In this context, one embodiment of the invention is a method of making huvastatin comprising the steps of combining together hydrolyzed pravastatin tetra-ol; an acyl thioester that donates an acyl moiety to the C8 hydroxyl group of hydrolyzed pravastatin tetra-ol in the presence of LovD acyltransferase; and LovD acyltransferase; and then allowing the LovD acyltransferase use an acyl group from the acyl thioester to regioselectively acylate the C8 hydroxyl group of hydrolyzed pravastatin tetra-ol, so that huvastatin is made. A related embodiment of the invention is a composition of matter comprising: hydrolyzed pravastatin tetra-ol; an acyl thioester that donates an acyl moiety to the C8 hydroxyl group of hydrolyzed pravastatin tetra-ol in the presence LovD acyltransferase; LovD acyltransferase; and huvastatin.

Yet another embodiment of the invention is a composition of matter comprising one or more of the huvastatin precursors, for example, hydrolyzed pravastatin tetra-ol or 6-hydroxyl-6-desmethylmonacolin J in the presence of thioester selected for its ability to acylate the C8 hydroxyl group of monacolin J or a monacolin J variant such as hydrolyzed pravastatin tetra-ol. Typically, such compositions can further include an organism as discussed above. Consequently, embodiments of the invention include processes for making simvastatin or huvastatin composition of matter substantially as herein disclosed and exemplified.

In situations where a modified organism that produces simvastatin (e.g. A. terreus with a disruption in the LDKS gene) also produces lovastatin (e.g. some minimal residual amount), the methods and materials disclosed herein allow the manipulation of the biochemical pathways/processes in the organism so that simvastatin or a related compound such as huvastatin is the predominant product of these pathways. A related embodiment is a composition of matter comprising an organism and simvastatin and/or huvastatin produced by that organism, wherein the amount of simvastatin and/or huvastatin in the composition is greater than the amount of lovastatin in the composition.

A related embodiment of the invention is a composition of matter comprising LovD, hydrolyzed pravastatin, and an acyl thioester. In illustrative embodiments, the composition of matter comprises an E. coli that produces huvastatin. In related embodiments, the composition of matter is an A. terreus (e.g. A. terreus with a disruption in the LDKS gene) that produces huvastatin. In situations where a modified organism that produces huvastatin (e.g. A. terreus with a disruption in the LDKS gene) also produces lovastatin (e.g. some minimal residual amount), the methods and materials disclosed herein allow the manipulation of the biochemical pathways/processes in the organism so that huvastatin is the predominant product of these pathways. A related embodiment is a composition of matter comprising an organism and huvastatin produced by that organism, wherein the amount of huvastatin in the composition is greater than the amount of lovastatin in the composition.

In certain embodiments of the invention, further components and/or methodological steps can be combined with one or more of the methods and materials discussed above. For example, the methods can further comprise using high cell-density fermentation to increase the effective concentration of LovD acyltransferase and optimise fermentation conditions and/or increasing LovD acyltransferase catalytic efficiencies towards the one or more acyl thioesters via protein engineering. Many other components or methods can be used to increase the production of simvastatin or of an intermediary compound that facilitates the production of simvastatin.

As noted above, lovastatin production (which requires LovD acyltransferase activity) is observed in a number of organisms such as Aspergillus terreus, Monascus ruber, Monascus purpureus, Monascus pilosus, Monascus vitreus, Monascus pubigerus, Candida cariosilognicola, Aspergillus ogea, Doratomyces stemonitis, Paecilomyces virion, Penicillum citrinum, Penicillin chgsogenum, Scopulariopsis brevicaulis or Trichoderma viride. In view of the nature of the invention disclosed herein, using known methods and materials in combination with the disclosure provided herein, one of skill in the art can combine a culture of one or more of these organisms (or any other organism known to produce lovastatin) with monacolin J and acyl thioester that donates an acyl moiety to the C8 hydroxyl group of monacolin J in the presence LovD acyltransferase (e.g. α-dimethylbutyrl-SNAC) to use LovD acyltransferase to make simvastatin. As shown by the instant disclosure for example, the nature of the instant invention allows one to make simvastatin and related compounds in the wide variety of lovastatin producing organism known in the art, without any specific knowledge regarding the characteristics of the specific LovD acyltransferase expressed in these organisms.

In an illustrative procedure for making simvastatin in a new organism (e.g. a fungal species related to A. terreus)

and/or testing the organism for its ability to do so, a first step is to make a mixture of monacolin J and acyl thioester that donates an acyl moiety to the C8 hydroxyl group of monacolin J. In a second step, this mixture is then combined with the organism (e.g. a lovastatin producing organism) in a fermentation mixture and allowed to grow. In a third step, the mixture is then tested for the presence of simvastatin, for example, by using a HPLC analysis as are discussed in the examples below. In view of the high throughput screening methodologies known in this art (see, e.g. Kittel et al., Metab. Eng. 2005, 7(1): 53-58, which is incorporated herein by reference), such methods can be performed on a large number of test samples such as the huge number of fungal cultures that are known in the art and readily available to the artisan so as to easily determine where and which species of organisms express polypeptides that possess a LovD acyltransferase activity that allows them to be used in the embodiments of the invention disclosed herein.

The methods disclosed herein also allow artisans to isolate and clone further LovD acyltransferase embodiments, for example, those embodiments which may have additional desirable qualities such as enhanced stability under various reaction conditions and/or favorable enzymatic kinetics under various reaction conditions. In this context, another embodiment of the invention is a method for identifying further LovD acyltransferase embodiments of the invention, the method comprising the simple steps of combining an organism likely to express LovD acyltransferase (e.g. a lovastatin producing organism) or a cell extract from that organism with an acyl thioester that donates an acyl moiety to the C8 hydroxyl group of monacolin J in the presence LovD acyltransferase (e.g. α-dimethylbutyrl-SNAC) and then testing this combination for the presence of simvastatin. The presence of simvastatin is indicative of the presence of the desired LovD acyltransferase activity. In view of the methods disclosed herein as well as high throughput screening methodologies known in this art (see, e.g. Kittel et al., Metab. Eng. 2005, 7(1): 53-58, which is incorporated herein by reference), such methods can be performed on a large number of test samples such as the huge number of fungal cultures that are known in the art and readily available to the artisan (e.g. lovastatin producing cultures) with only a minimal amount of experimentation. Consequently, the large number of lovastatin producing organisms known in the art, the high throughput screening methodologies known in this art and the instant disclosure guide a worker to easily determine where and which species of polypeptides possess a LovD acyltransferase activity that allows them to be used in the embodiments of the invention disclosed herein.

Once LovD acyltransferase activity is observed using these methods, it can then be used in art accepted methods to clone the gene encoding the protein having this activity. Alternatively, a library of an organism's genes can then be screened using a LovD acyltransferase polynucleotide sequence (e.g. from A. terreus) either alone or in combination with functional studies as discussed above in order to identify a new a LovD acyltransferase polynucleotide sequence having homology to SEQ ID NO: 1 or SEQ ID NO: 2). In this context, homologous enzymes to LovD that can be found in, for example, but not limited to, fungal polyketide gene clusters. For example, Mlc in the compactin biosynthetic pathway is implicated to catalyze the identical transacylation reaction (see, e.g., Y. Abe, T. et. al., Mol Genet Genomics. 2002, 267, 636-646), whereas an acyl-transferase in the squalestatin pathway can catalyze a similar reaction between an ACP-bound tetraketide thioester and an aglycon (see, e.g., R. J. Cox, F. et. al., Chem Commun (Camb) 2004, 20, 2260-2261). The amino acid sequence of LovD resembles type C β-lactamase enzymes, which catalyze the hydrolytic inactivation of the β-lactam class of antibiotics (see, e.g., E. Lobkovsky, E. M. et. al., Biochemistry, 1994, 33, 6762-6772 and A. Dubus, D. et. al., Biochem. J. 1993, 292, 537-543). Alignment of LovD with the Enterobacter cloacae P99 lactamse (see, e.g., S. D. Goldberg, et. al., Protein Sci. 2003, 12, 1633-1645) shows moderate sequence homology, including potentially conserved active site residues, such as the catalytic Ser76, Lys79, Tyr188, and Lys315 (see. e.g. S. D. Goldberg, et. al., Protein Sci. 2003, 12, 1633-1645). In view of these methods, yet another embodiment of the invention is an isolated LovD acyltransferase polypeptide having at least 80%, 85%, 90%, 95%, 96%, 97%, 98%, or 99% sequence identity with the amino acid sequence set out in SEQ ID NO:1, wherein the polypeptide has the ability to acylate the C8 hydroxyl group of monacolin J in the presence of an appropriate acyl thioester donor (e.g. α-dimethylbutyrl-SNAC).

As disclosed herein, an "acyl thioester to regioselectively acylate the C8 hydroxyl group of monacolin J" is a compound having an acyl group that can be transferred to monacolin J or a related compound so as to make simvastatin or a related compound as disclosed herein. A wide variety of such agents are known in the art that are further shown herein to have this activity (see, e.g. the illustrative acyl-thioesters in Table 1). In addition to those known in the art and further shown by the instant disclosure to have this activity, any potential acyl donor/carrier known in the art (or synthesized de novo) that further has an ability to acylate C8 of monacolin J so as to produce simvastatin can be easily identified by comparative experiments with the acyl donors disclosed herein (e.g. acyl-SNAC). Typically in such experiments, the acyl thioester is a butyrlyl-thioester, a N-acetylcysteamine thioester or a methyl-thioglycolate thioester. Optionally, the acyl thioester comprises medium chain length (C3-C6) acyl group moieties. In certain embodiments of the invention, the acyl thioester is able to cross the cellular membranes of Escherichia coli or Aspergillus terreus cells growing within a fermentation media. Typically, the acyl thioester is selected from the group consisting of α-dimethylbutyryl-S-methyl-mercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB).

As shown by the instant disclosure, the nature of the instant invention allows one to readily identify a compound as a "acyl thioester to regioselectively acylate the C8 hydroxyl group of monacolin J" with minimal experimentation. In one illustrative procedure for identifying a compound as a "acyl thioester to regioselectively acylate the C8 hydroxyl group of monacolin J", a first step is to make a mixture of monacolin J and A. terreus. In a second step, this mixture is then combined with a test compound in a fermentation mixture and allowed to grow. In a third step, the mixture is then tested for the presence of simvastatin, for example by using a HPLC analysis as are discussed in the examples below, wherein the presence of simvastatin identifies the compound as having this activity. In view of the high throughput screening methodologies known in this art (see, e.g. Kittel et al., Metab. Eng. 2005, 7(1): 53-58, which is incorporated herein by reference), such methods can be performed on a large number of test samples so as to easily determine where and which species of acyl donor compounds possess a utility that allows them to be used in the embodiments of the invention disclosed herein.

Embodiments of the invention also include articles of manufacture and/or kits designed to facilitate the methods of the invention. Typically such kits include instructions for using the elements therein according to the methods of the present invention. Such kits can comprise a carrier means being compartmentalized to receive in close confinement one or more container means such as vials, tubes, and the like, each of the container means comprising one of the separate elements to be used in the method. For example, one of the containers can comprise a vial, for example, containing A. terreus having a disruption in the LDKS gene and another vial containing an acyl-SNAC compound or the like, both of which can be added to a fermentation mixture to produce simvastatin.

In a typical embodiment of the invention, an article of manufacture containing materials useful for production of simvastatin is provided. The article of manufacture comprises a container and a label. Suitable containers include, for example, bottles, vials, syringes, and test tubes. The containers may be formed from a variety of materials such as glass or plastic. The container can hold a composition of matter (e.g. an acyl carrier and an organism) which can produce simvastatin, for example. The label on, or associated with, the container indicates that the composition is used for examining cellular polypeptides. The article of manufacture may further comprise a second container comprising another compound or substrate for addition to the fermentation mixture for example. This compound or substrate, for example, might be used to increase the production of certain intermediaries in the production of simvastatin, such as monacolin J. It may further include other materials desirable from a commercial and user standpoint, including other buffers, diluents, filters, needles, syringes, and package inserts with instructions for use.

Further biological aspects of the invention are discussed in the following sections.

Biochemical Aspects of Embodiments of the Invention

An appreciation of certain aspects of the invention is facilitated by discussions of biochemical aspects of the invention. In the following sections and examples of the specification, the LovD acyltransferase is the A. terreus LovD polypeptide shown in SEQ ID NO: 1, and is typically referred to as "LovD" or the "LovD enzyme".

Figure 7:
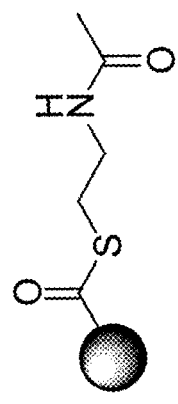
FIG. 7. Acyl-SNAC. The shaded circle denotes any functional group.
Figure 10:
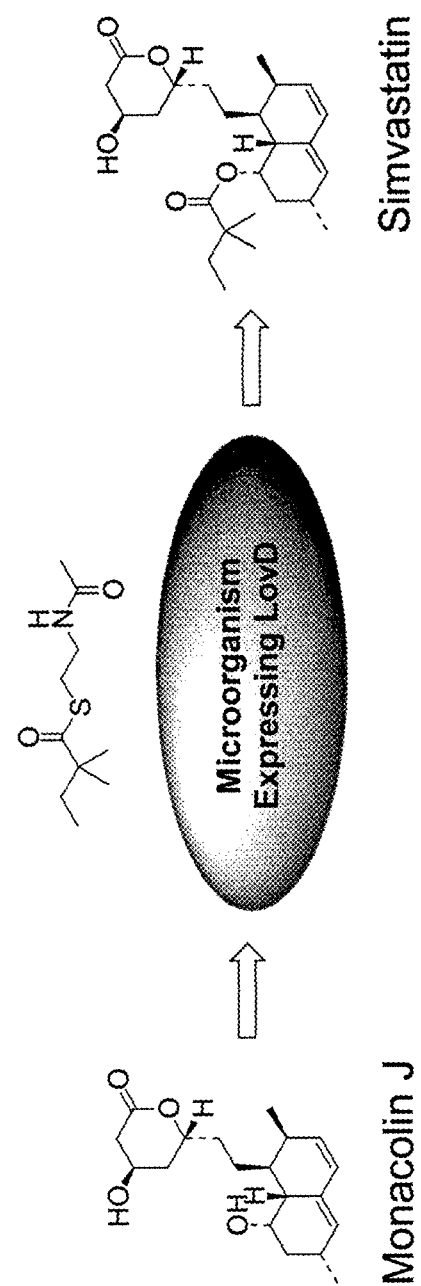
FIG. 10. Microbial conversion of monacolin J into simvastatin.
Figure 11:
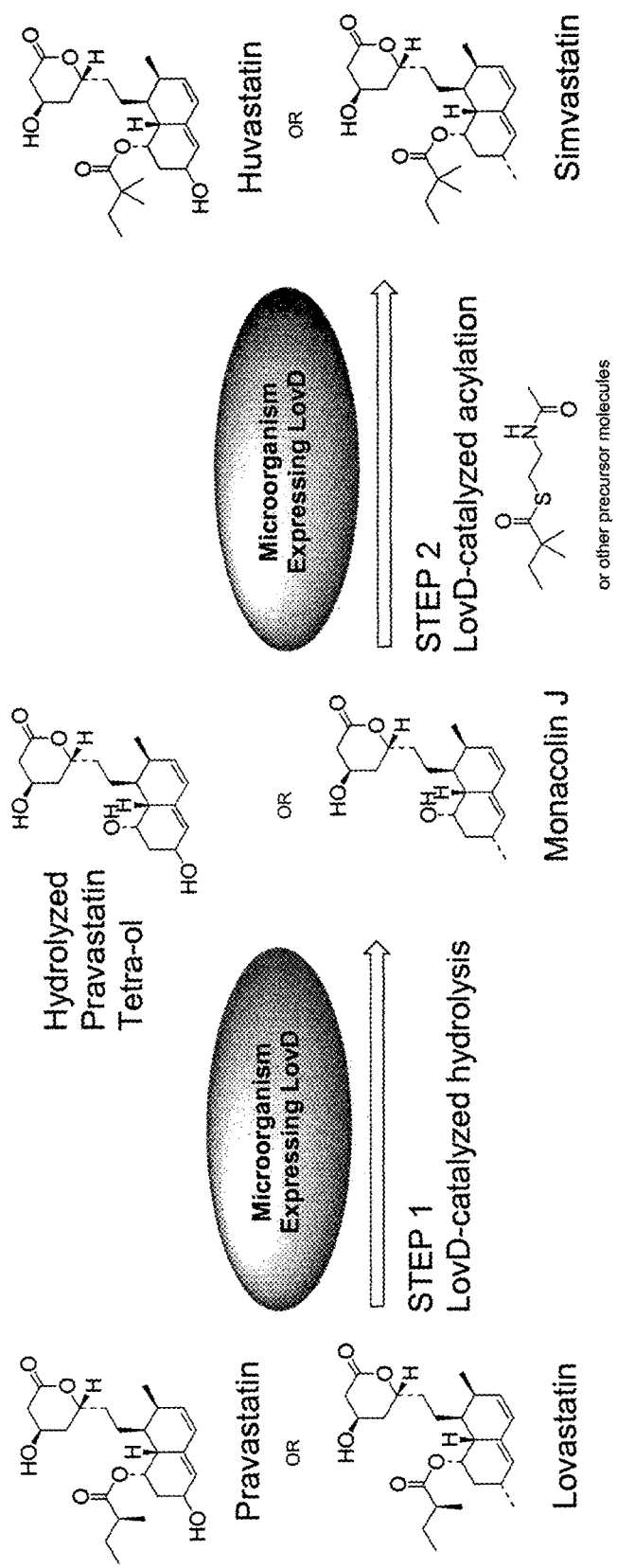
FIG. 11. LovD catalyzed hydrolysis and LovD catalyzed acylation.
Figure 12:
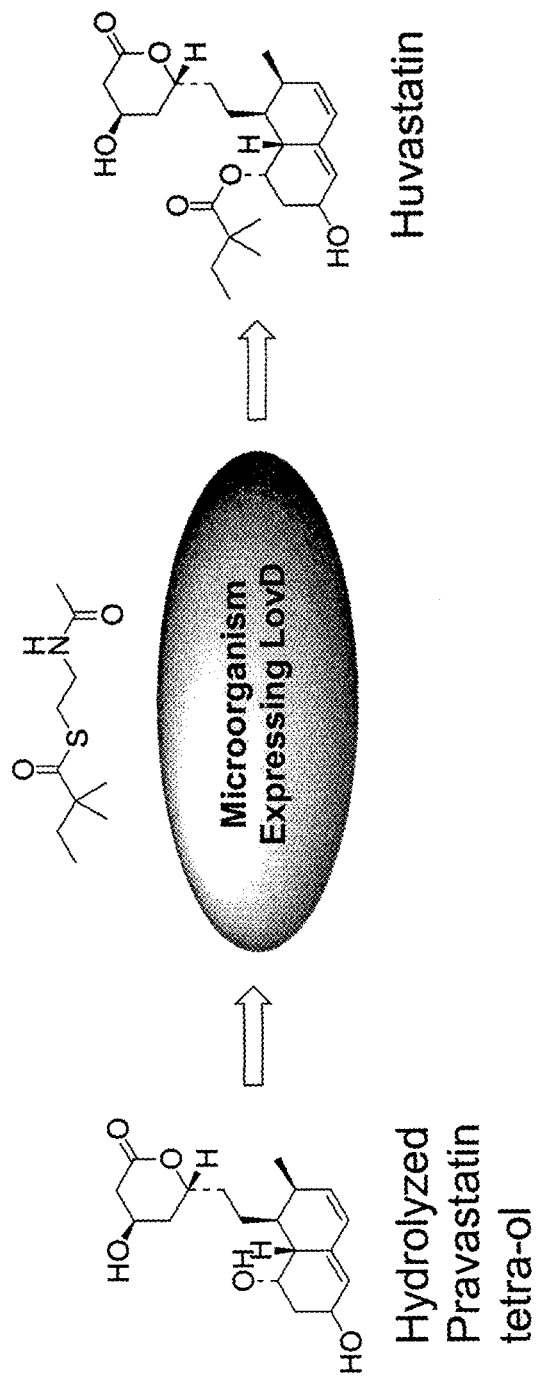
FIG. 12. Production of huvastatin in a microorganism expressing LovD.

The promiscuity of the LovD enzyme towards alternative acyl donors was examined. We found that the acyl carrier/donor does not need to be attached to the LDKS. Alternative thiol containing carriers are suitable, including acyl-CoA (coenzyme A) and more importantly, the membrane permeable acyl-SNAC (FIG. 7). We found that LovD does not need to interact with LovF and can accept an acyl group from a variety of different donors. We also found that LovD can transfer a variety of acyl substrates to the C8-hydroxyl group of monacolin J to yield an assortment of lovastatin analogs. We found that LovD can regioselectively acylate the C8 hydroxyl position in monacolin J with a variety of acyl substrates. Amongst the successful acyl groups is α-dimethylbutyryl-SNAC, which yields simvastatin in the presence of LovD and monacolin J. We also found that the transacylation activity of LovD be confirmed in vitro and be reconstituted in a heterologous host. We found that LovD directly acylates monacolin J with α-dimethybutyrate to yield the pharmaceutically important simvastatin. α-Dimethylbutyryl-SNAC is cell-permeable. The cell permeable properties of α-dimethylbutyryl-SNAC has an important implication: the compound can be supplied as a precursor in vivo to an organism, such as a prokaryote or an eukaryote, expressing LovD. The prokaryote or eukaryote, when fermented in the presence of monacolin J (either made endogenously, or supplied exogenously to the fermentation media) can directly afford simvastatin. E. coli, for example, was examined as a microbial host for the bioconversion of monacolin J into simvastatin. Both monacolin J and dimethylbutyryl-SNAC were added to a growing culture of an E. coli strain overexpressing the LovD enzyme (FIG. 10). Simvastatin was isolated from the fermentation broth of the culture in good yield. This technique can be used in the native lovastatin producer Aspergillus terreus. A strain that is deficient in LDKS can be constructed so that it will not be able to synthesize the 2-methylbutyrate side chain. α-Dimethylbutyryl-SNAC can be added to the fermentation medium. Simvastatin can be synthesized during this single step fermentation.

As noted above, LovD can catalyze the final acyl transfer step during lovastatin biosynthesis and can regiospecifically acylate the C8 hydroxyl group in monacolin J. LovD can display broad substrate specificity towards the decalin aglycon, the acyl carrier, and the acyl group. When supplemented with the unnatural substrate α-dimethylbutyryl-SNAC, LovD can produce the pharmaceutically important simvastatin both in vitro and in vivo. When an α-dimethylbutyryl-thioester precursor is supplied to a LovF-deficient strain of A. terreus, the lovastatin biosynthetic pathway can be redirected to afford simvastatin directly. This invention allows for: 1) Microbial conversion of monacolin J to simvastatin (FIG. 10); 2) Coculturing of the LovD overexpression strain with a strain that produces monacolin J; and 3) Single step fermentation of Aspergillus terreus (ΔLDKS) to yield simvastatin. In each case, the acyl substrate α-dimethylbutyryl-SNAC can be synthesized chemically and be added to the fermentation broth.

Figure 5:
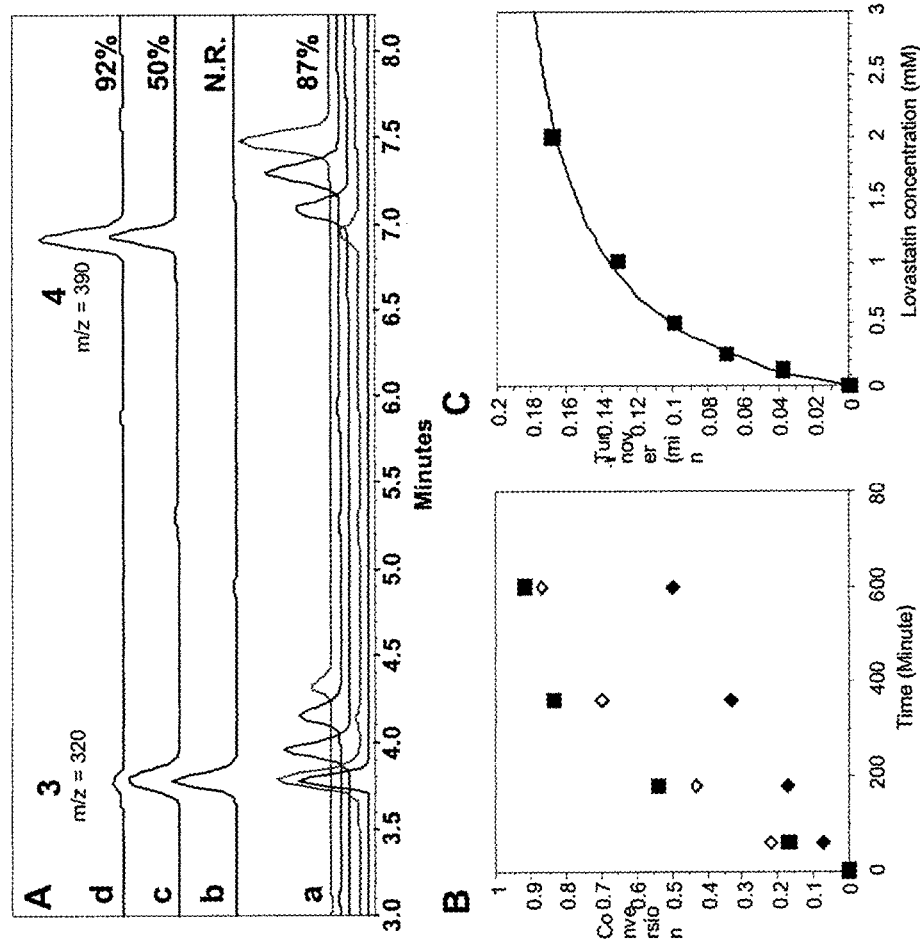
FIG. 5. A) HPLC (238 nm) trace showing formation of 4 by LovD mediated acyl transfer. Gradient: 60% B-95% B, 5 min; 95% B, 15 min; A: $H_2O$+0.1% TFA; B: acetonitrile+0.1% TFA; a) LovD+monacolin J+butyryl-CoA time course (0, 1, 3, 6 and 10 hours); b) LovD S76A+monacolin J+butyryl-CoA, 10 hrs; c) LovD+butyryl-SNAC, 10 hrs; d) LovD+butyryl-SMTG, 10 hrs. Assay conditions: 1 mM monacolin J, 4 mM butyryl-CoA, 10 μLovD, 50 mM HEPES, pH 7.9, 25 degrees C. (B) Conversion as a function of time for (◇) butyryl-CoA (◆) butyryl-SNAC, (■) butyryl-SMTG. The apparent $k_{cat}$ values reported throughout the text are initial turnover rates in the linear range. (C) Michaelis-Menten plot of LovD catalyzed hydrolysis of lovastatin to monacolin J. The reaction progress is monitored by HPLC. $k_{cat}$: 0.21±0.01 $min^{-1}$; Kin: 0.56±0.05 mM.
Figure 6:
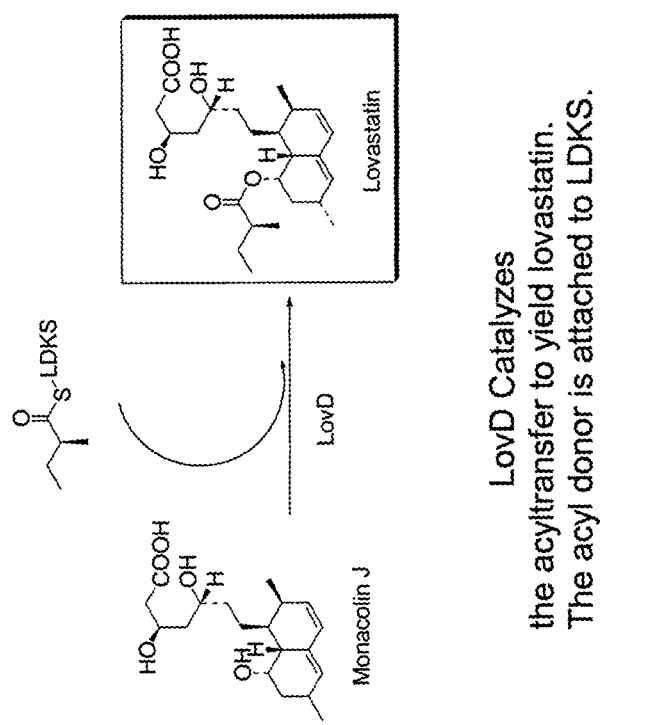
FIG. 6. LovD catalyzes the acyltransfer to yield lovastatin. The acyl donor is attached to LDKS.

LovD does not Need to Interact with LovF, and LovD can Catalyze the Transacylation Reaction of Acyl-CoA and Other Alternate Thiol-Containing Carriers (FIG. 5)

We first examined if an acyl-CoA can be used as substrate for the transacylation reaction. The uninterrupted gene of LovD was amplified from A. terreus genomic DNA using splice by overlap extension PCR and was inserted into the pET28a expression vector. Overexpression of soluble, N-terminal 6×His fusion LovD was performed in E. coli strain BL21 (DE3)/pAW31. LovD was purified using Nickel-NTA affinity column to homogeneity (final yield ~40 mg/L). The substrate monacolin J (1 mM) was prepared through the LiOH hydrolysis of lovastatin and was added to a reaction mixture containing pure LovD (10 µM) and butyryl-CoA (4 mM), which is a commercially available acyl-CoA that best mimics the natural α-methylbutyrate side chain. The reaction mixture was incubated at room temperature, extracted with ethyl acetate and analyzed by HPLC and LC-MS (FIG. 5).

A single, more hydrophobic compound with an identical UV absorbance as lovastatin was formed in the reaction mixture, in conjunction with the disappearance of monacolin J (FIG. 5, trace a). The mass of the new compound was found to be 391 (M+H), in accordance with addition of a butyryl group to monacolin J. The selective esterification of C8 hydroxyl group of monacolin J to yield 4 is confirmed by proton NMR spectroscopy (CDCl$_3$, 500 MHz). The proton NMR of 4 (lactonized form) is nearly identical to that of lovastatin except the aliphatic signals of the linear acyl side chain. The diagnostic H8 multiplet (assigned using $^1$H-$^1$H COSY, $^1$H-$^{13}$C HMQC and $^1$H-$^{13}$C HMBC) in 4 is shifted downfield to δ 5.38, compared to δ 4.23 observed for the same proton in monacolin J. This is consistent with the deshielding effect of the acyloxy substitution at C8. Protons H11 and H13 of carbons bearing other hydroxyl groups were shifted from δ 4.71 and δ 4.38 in monacolin J to δ 4.51 and δ 4.36 in 4, respectively.

As shown in FIG. 5A (trace a), 87% conversion of monacolin J to 4 was observed after 10 hours using butyryl-CoA as an acyl donor. A time-course study revealed an apparent turnover rate of 0.18 min$^{-1}$ (FIG. 5B). The observed 87% conversion is likely approaching equilibrium as evident in FIG. 5B. To examine the biochemical nature of the equilibrium conversion, we assayed whether LovD also catalyzes the reverse, hydrolysis reaction. Indeed, when lovastatin was used as the only substrate, formation of monacolin J was readily detected with $k_{cat}$ and $K_m$ values of 0.21±0.01 mind and 0.56±0.05 mM, respectively (FIG. 5C). When the putative active site serine in LovD (Ser76) was mutated to an alanine, formation of 4 or the hydrolysis of lovastatin cannot be detected (FIG. 5A, trace b).

Figure 4:
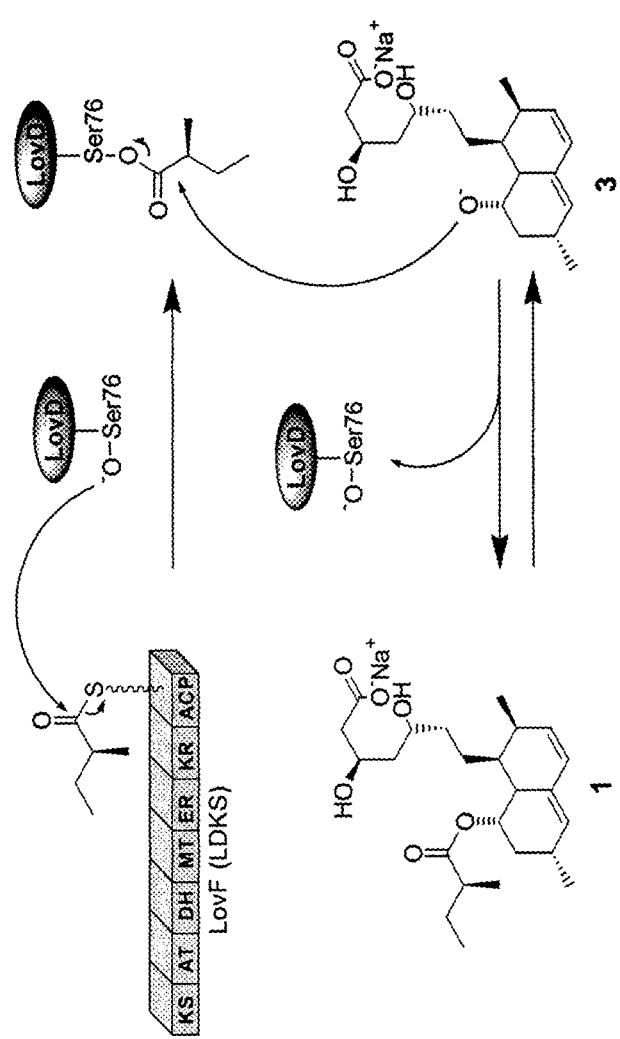
FIG. 4. Acyl transfer reaction of the invention in *A. terreus*. Serine 76 can be the active site nucleophile.

The enzymatic synthesis of 4 confirms that LovD indeed catalyzes the acyl transfer reaction shown in FIG. 4. Furthermore, this result show that direct association between domains of LovF and LovD is not required for catalytic turnover, in contrast to the previously hypothesized mode of LovD catalysis (see, e.g., J. Kennedy, K. et. al., *Science*, 1999, 284, 1368-1372 and C. R. Hutchinson, J. et. al., *Antonie Van Leeuwenhoek* 2000, 78, 287-295). Acyl-S-CoA can substitute for acyl-S-LovF, albeit likely with a significantly higher $K_m$ due to the loss of potential protein-protein interactions.

Transacylation Assays with Several Different Commercially Available Acyl Substituents Revealed LovD's Preference Towards Medium Chain Length (C3-C6) Acyl Groups We assayed the tolerance of LovD towards different acyl substituents by performing the transacylation assay with various commercially available acyl-CoAs (Table 1A). All assays were perform with 1 mM monacolin J, 4 mM acyl-CoA and 10 uM LovD for 10 hours. Our results clearly indicate LovD displays preference towards medium chain length (C3-C6) acyl groups with butyryl-CoA being the optimal alkylacyl-CoA substrate. Surprisingly, the bulkier benzoyl-CoA was one of the best acyl substrate examined, with nearly 70% conversion of simvastatin to the corresponding 8-benzoxy-lovastatin analog (apparent $k_{cat}$=0.16 mind). Introducing α-β unsaturation significantly decreased the reaction rate, as seen in the 6% acylation of monacolin J in the presence of crotonyl-CoA. Acetoacetyl-CoA and β-hydroxylbutyryl-CoA were both excellent substrates of LovD, in good agreement with the isolation of monacolin X (see, e.g., A. Endo, K. et. al., *J. Antibiot,* 1986, 38, 321-327) and monacolin M (see, e.g., A. Endo, D. et. al., *J. Antibiot.* 1986, 39, 1670-1673) from the natural host, respectively. Among the CoA substrates assayed, LovD was inactive towards malonyl- and palmitoyl-CoA.

Further Transacylation Assays with an Alternative Acyl Carrier, Acyl-SNAC, which is Simpler to Prepare Synthetically and can Penetrate Cell Membrane Under In Vivo Conditions, Revealed that Acyl-SNAC is a Competent Substrate for LovD To further examine the substrate specificities of LovD towards alternative acyl carriers, especially those that are simpler to prepare synthetically, and can penetrate cell membrane under in vivo conditions, we assayed two variants of butyryl-thioesters as substrates of LovD (FIG. 5). N-acetylcysteamine thioesters (SNAC) have been used extensively as probes and precursors in studying natural product biochemistry (see, e.g. Auclair et al., *Science,* 1997, 277, 367-369). Methyl-thioglycolate (SMTG) was recently shown to be a cost-effective substitute for SNAC in the precursor-directed biosynthesis of erythromycin (see, e.g., S. Murli, K. S. et. al., *Appl. Environ. Microbiol.* 2005, 71, 4503-4509). FIG. 5 (traces c and d) shows the conversion of monacolin J to 4 when these butyryl-thioesters were used as acyl donors. Both SNAC and SMTG thioesters substituted for butyryl-CoA efficiently, with apparent $k_{cat}$ values of 0.09 min$^{-1}$ and 0.23 min$^{-1}$ (FIG. 5B), respectively, further highlighting that protein-protein interactions between LovD and LovF, as well as the interaction between LovD and the phosphopantetheine arm are not required for acyl transfer. Butyryl-thioethane, however, was not a competent substrate of LovD and supported only 4% conversion of monacolin J to 4. Similarly, benzoyl-SNAC and benzoyl-SMTG substituted for benzyl-CoA efficiently, with apparent $k_{cat}$ values of 0.12 min$^{-1}$ and 0.15 min$^{-1}$, respectively (Table 1A).

Figure 8:
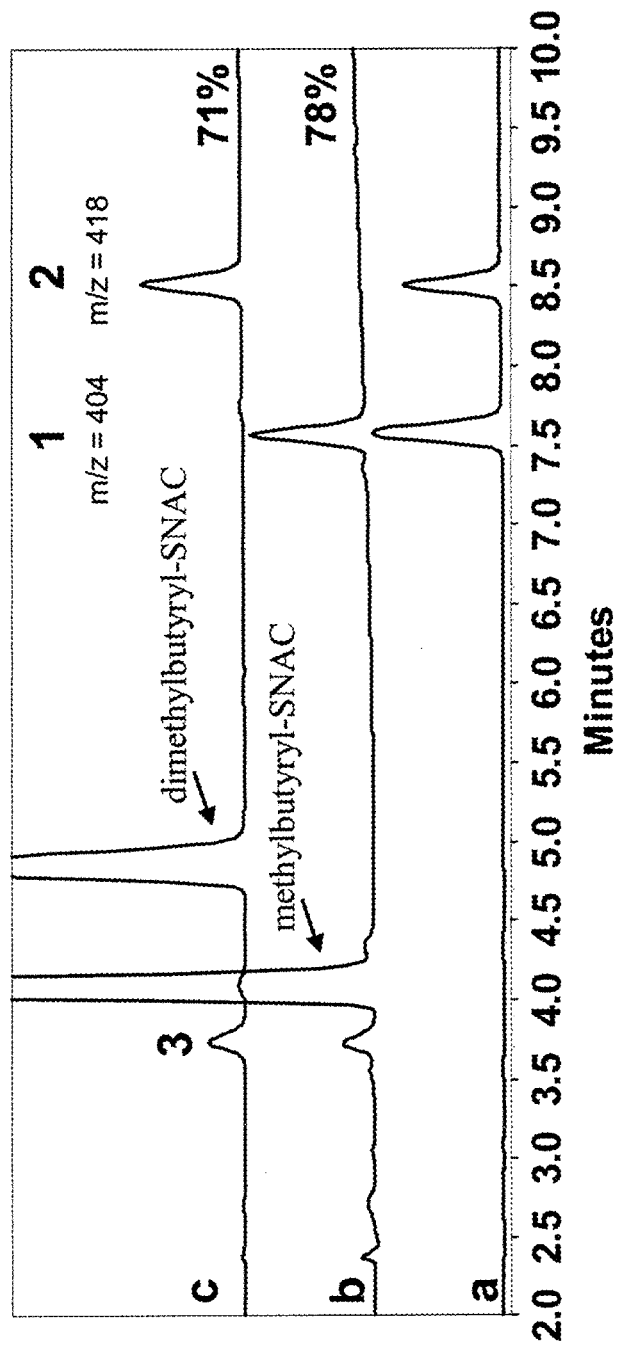
FIG. 8. HPLC (238 nm) trace showing formation of simvastatin and lovastatin by LovD mediated acyl transfer. Gradient is the same as that described in FIG. 1; a) authentic standards of lovastatin and simvastatin; b) monacolin J+α-S-methylbutyryl-SNAC; c) monacolin J+α-dimethylbutyryl-SNAC. Assay conditions: 1 mM monacolin J, 10 mM acyl-SNAC, 100 μM LovD, 50 mM HEPES, pH 7.9, 25° C., 6 hrs.

Assay for the In Vitro Chemoenzymatic Synthesis of Lovastatin and Simvastatin Using A-S-Methylbutyryl-SNAC and A-Dimethylbutyryl-SNAC Revealed that Monacolin J is Converted to Simvastatin in the Presence of Acyl-SNAC We then synthesized α-S-methylbutyryl-SNAC and α-dimethylbutyryl-SNAC and assayed for the in vitro chemoenzymatic synthesis of lovastatin and simvastatin, respectively. The results are shown in FIG. 8 and Table 1A. Authentic samples of lovastatin and simvastatin were used as references for HPLC detection (FIG. 8, trace a). The natural, α-S-methylbutyrate side chain was surprisingly a poorer substrate compared to butyryl-, pentanoyl- and hexanoyl-SNAC. The apparent $k_{cat}$ (~0.04 min$^{-1}$) of lovastatin synthesis is more than 50% slower than that of LovD towards butyryl-SNAC. This suggested that the wild type LovD has not been optimized towards transferring the branched substrate. Addition of a second methyl substituent at the α-position further attenuated the rate of acylation, likely attributed to the increased steric hindrance of the dimethyl moiety. Under standard assay conditions, approximately 10% of monacolin J was converted to simvastatin when α-dimethylbutyryl-SNAC is used as a substrate (apparent $k_{cat}$=0.02 min$^{-1}$). We were able to reach equilibrium conversions >70% when 100 uM LovD and a 10 fold excess of α-dimethyl-SNAC or α-dimethyl-SMTG were added to the in vitro reaction mixture (FIG. 8, traces b and c).

Figure 9:
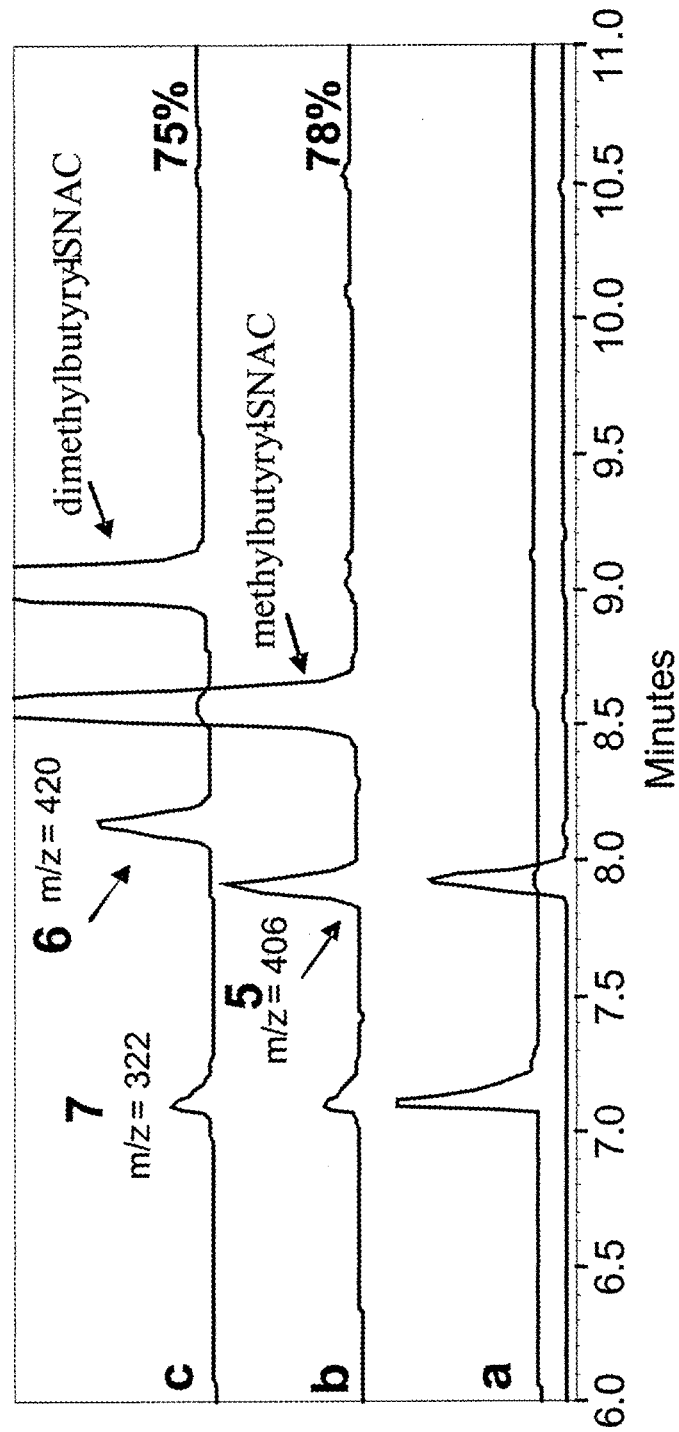
FIG. 9. HPLC (238 nm) traces showing formation of pravastatin and huvastatin by LovD mediated acylation of the tetra-ol 7. Gradient: 5% B-95% B, 5 min; 95% B, 15 min; A: $H_2O$+0.1% TFA; B: acetonitrile+0.1% TFA; a) authentic standards of pravastatin and 7; b) 7+α-S-methylbutyryl-SNAC; c) 7+α-dimethylbutyryl-SNAC. Assay conditions: 1 mM monacolin J, 10 mM acyl-SNAC, 100 uM LovD, 50 mM HEPES, pH 7.9, 25 degrees C., 6 hrs.

LovD, In Vitro, can Transfer a Variety of Acyl Substrates (not Just LDKS) to the C-8-Hydroxyl Group of Monacolin J to Yield an Assortment of Lovastatin Analogs To test the substrate specificity of LovD towards monacolin J variants, we assayed the conversion of tetra-ol 7 to 8, pravastatin (5) and huvastatin (6) (FIG. 9). It has been shown previously shown that when 8-desmethyl-monacolin J is fed to *A. terreus* mutant blocked in monacolin J biosynthesis, compactin can be readily isolated (see, e.g., J. L. Sorensen, K. et. al., *Org. Biomol. Chem.* 2003, 1, 50-59). This hints that LovD may be tolerant of substitutions at the C6 position of the decalin core. Indeed, LovD displays relaxed specificity towards the hydroxyl substitution at C6 and catalyzed the acylation of 7 with higher efficiencies. The apparent turnover rates for the synthesis of 8, pravastatin, or huvastatin using the corresponding acyl-thioesters were 0.18, 0.11, 0.03 min$^{-1}$, respectively. The retention time of authentic pravastatin was identical to the enzymatically synthesized compound. The mass of the newly formed compounds was verified by LC-MS. We did not detect any di-acylated products in reaction mixture.

In Vivo Data Show that LovD can be Used for Preparative Biosynthesis of Lovastatin Analogs To demonstrate LovD can be used for preparative biosynthesis of lovastatin analogs, we first attempted to perform the benzylation reaction in vivo using *E. coli* as a heterologous host. The BL21(DE3)/pAW31 overexpression strain was grown in a shake flask (200 mL) to an $OD_{600}$ of 1.0, at which time 1 mM IPTG, 0.8 mM monacolin J and 4 mM of either benzoyl-SNAC or benzoyl-SMTG were added to the culture. Expression of LovD and bioconversion was performed at 18° C. The culture was extracted and analyzed for the formation of 8-benzoyl-monacolin J. When supplemented with benzoyl-SNAC, 84% conversion of monacolin J was detected within 20 hours post-induction. The product was lactonized and purified by a single silica-gel chromatography step. The NMR spectra confirmed the regioselective benzoylation of the C8 hydroxyl group as the diagnostic H8 multiplet is shifted downfield to δ 5.61. In contrast, only 40% benzoylation was observed for the culture that was supplemented with benzoyl-SMTG. Benzoyl-SMTG was rapidly degraded by *E. coli* and no trace can be detected in the culture medium after 24 hours.

An Acyl Substrate, A-Dimethylbutyryl-SNAC Yielded Simvastatin in the Presence of Purified LovD and Monacolin J We performed low cell-density fermentation with α-dimethylbutyryl-SNAC as a precursor to yield simvastatin from monacolin J in a single biosynthetic step. After two days of culturing, we observed ~90% conversion of monacolin J to simvastatin (see, e.g., "fermentation conditions" listed below). The product was purified and the proton and carbon NMR spectra were identical to those of the commercially purchased compound. The lower yield of simvastatin is consistent with the slower turnover rate observed in vitro, which may be further decreased at lower intracellular concentration of the SNAC precursor. Other factors, such as the reversible hydrolysis of simvastatin (we observed simvastatin hydrolysis in the presence of LovD—the $k_{cat}$ (0.02 $min^{-1}$) of hydrolysis is ~10-fold slower than that of lovastatin hydrolysis shown in FIG. 5C) and inactivation of LovD after prolonged fermentation may lead to the observed conversion. We anticipate the yield can be significantly improved by several means, such as 1) use high cell-density fermentation to increase the effective concentration of LovD and optimize fermentation conditions; 2) increase LovD catalytic efficiencies towards the unnatural precursor by protein engineering.

Throughout this application, various publications are referenced. The disclosures of these publications are hereby incorporated by reference herein in their entireties.

EXAMPLES

The Examples below provide illustrative methods and materials that can be used in the practice the various embodiments of the invention disclosed herein.

Example 1: Cloning, Expression and Purification of Illustrative LovD Acyltransferase The three exons of *A. terreus* LovD were individually amplified from the genomic DNA of *A. terreus* and spliced to yield a continuous open reading frame using splice by overlap extension PCR. The restriction sites NdeI and HindIII were introduced on the 5' and 3' outside primers, respectively. The gene cassette was ligated into pET28 (Novagen) to yield the expression construct pAW31. The *E. coli* BL21(DE3) strain transformed with pAW31 was grown in LB medium at 37° C. to a $OD_{600}$ of 0.5, at which time 1 mM IPTG was added to the culture and expression was performed at 18° C. for 24 hours. Cells were collected by centrifugation, resuspended in Buffer A (50 mM Tris, pH. 8.0, 2 mM DTT, 2 mM EDTA) and were lysed by sonication. Cell debris and insoluble proteins were removed by centrifugation (17,000 g, 4° C., 1 hour). To the cleared lysate, 2 mL of Ni-NTA resin (Qiagen) was added. LovD was purified using a step gradient of buffer A with increasing concentration of imidazole. Pure (>95%) LovD proteins were eluted at buffer A containing 250 mM imidazole, buffer exchanged into Buffer A without imidazole, concentrated, aliquoted and flash frozen. The frozen LovD aliquots were of single use only. We observed significant decrease in enzyme activity after repeated freeze-thaw cycles.

Example 2: Illustrative Fermentation Conditions

Fermentation conditions: 500 mL culture with LB media with 30 mg/L kanamycin. At $OD_{600}$ of 1.0, cells were concentrated to a final $OD_{600}$ of 5.0 and induced with 1 mM IPTG. Substrates monacolin J and α-dimethylbutyryl-SNAC were added to a final concentration of 1 mM and 4 mM. At different time points, culture samples were collected, centrifuged, filtered and injected on to HPLC (20 μL). Extraction conditions: When maximum conversion was reached, the broth was acidified to pH of 2.0, extracted with ethyl acetate, dried and redissolved in toluene. The lactone form of monacolin J was obtained by refluxing using a soxhlet apparatus as discussed before (see, e.g., J. L. Sorensen, K. et. al., *Org. Biomol. Chem.* 2003, 1, 50-59).

A variety of fermentation media such as LB, F1 or TB fermentation media are well known in the art which can be used or adapted for use with embodiments of the invention disclosed herein including LB, TB and F1 media. Further media tailored to growing organisms such as A. *Terreus* and *M. pilosus* are also well known in the art (see, e.g. Miyake et al., Biosci. Biotechnol. Biochem., 70(5): 1154-1159 (2006) and Hajjaj et al., Applied and Environmental Microbiology, 67: 2596-2602 (2001), the contents of which are incorporated by reference).

A typical Luria Bertani Broth (LB) Recipe is as follows:
10 g Tryptone
5 g Yeast Extract
10 g NaCl
1 L distilled water
pH to ~7.3-7.5.
A typical TB Recipe is as follows:
3 g Pipes (10 mM)
2.2 g CaCl2 H₂O (15 mM)
18.6 KCl (250 mM)
10.9 g MnCl2 (55 mM)
1 L distilled water
pH to 6.7-6.8 with KOH
A typical F1 media can be found in U.S. Pat. No. 5,064,856, the contents of which are incorporated herein by reference.

Typically such media is sterilized after preparation by procedures such as filtration or autoclaving.

Example 3: Improving Simvastatin Bioconversion in *Escherichia Coli* by Deletion of BioH This example further characterizes the LovD polypeptide encoded in the lovastatin gene cluster (see also Xie et al., (2006) Chem Biol 13: 1161-1169). LovD catalyzes the last step of lovastatin biosynthesis and is responsible for transferring the 2-methylbutyrate side chain from the megasynthase LovF to the immediate biosynthetic precursor, monacolin J (MJ) acid (see, e.g., Kennedy et al., (1999) Science 284: 1368-1372). We demonstrated that LovD displays broad substrate specificity towards the decalin core, the thioester acyl unit and the thioester acyl carrier. Using an *Escherichia coli* strain overexpressing LovD and a cell-membrane permeable thioester dimethylbutyryl-S-methyl mercaptopropionate (DMB-S-MMP) (FIG. 13A), we developed a whole cell biocatalytic process that can convert MJ acid to simvastatin acid in one step with high yields (see, e.g., Xie et al., (2007) Appl Environ Microbiol 73: 2054-2060). The fermentation process can be an economically competitive alternative to the current synthetic routes.

Figure 13:
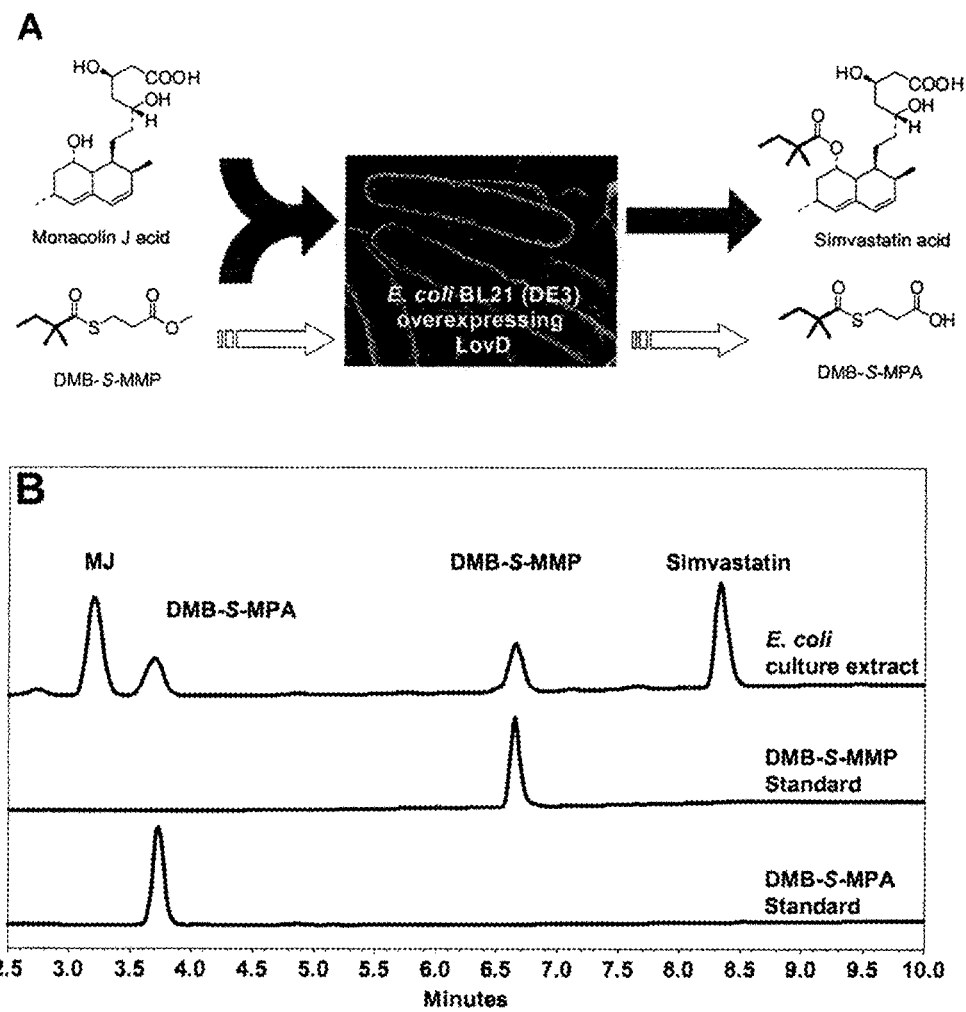
FIG. 13. (A) Whole cell biocatalytic conversion of simvastatin acid from monacolin J acid and DMB-S-MMP. The *E. coli* strain overexpresses the acyltransferase LovD. Hydrolysis of DMB-S-MMP to yield DMB-S-MPA is a competing reaction. (B) top trace: typical profile of reactants and products from the whole cell conversion experiment. Bottom traces: standards for DMB-S-MMP and DMB-S-MPA. The spectra were collected at 238 nm.

The thioester DMB-S-MMP is an integral component of simvastatin bioconversion. It is among the most catalytically efficient acyl donors examined for the acyltransfer reaction, while being the least expensive to synthesize. One significant drawback associated with this compound is hydrolysis of the methyl ester bond in DMB-S-MMP that yields dimethylbutyryl mercaptopropionic acid (DMB-S-MPA) (FIG. 13). The hydrolysis reaction is enzymatic because no degradation was observed in the absence of *E. coli*, and is dramatically elevated during high cell-density fermentation. The side reaction is undesirable for three reasons: 1) Hydrolysis of the substrate depletes DMB-S-MMP available for LovD-catalyzed transacylation, requiring the thioester to be added in high molar excess and to be replenished frequently during fermentation; 2) Since DMB-S-MPA is less efficient compared to DMB-S-MMP as a dimethylbutyrate donor (~10 fold slower) (see, e.g., Xie et al., (2007) Appl Environ Microbiol 73: 2054-2060), accumulation of the more soluble DMB-S-MPA can serve as a competing acyl substrate for LovD. This effectively decreases the reaction velocity and has been demonstrated in vitro using purified LovD. Therefore, the overall duration of the bioconversion is unnecessarily prolonged; and 3) The carboxylic acid moiety of DMB-S-MPA interferes with purification of simvastatin acid from the culture medium at completion of the bioconversion. Both compounds precipitate from the culture broth upon acidification of the medium and additional separation steps are required before crystallization of simvastatin. While DMB-S-MPA can be removed by washing the filtrate with excessive amount of water, an appreciable amount of simvastatin acid were lost during the washing steps, resulting in decrease in overall recovery.

Eliminating the undesirable hydrolysis side reaction can therefore improve the economics of the whole cell biocatalytic process and the downstream purification steps. The most immediate goal is therefore to pinpoint the enzyme(s) responsible for the undesirable side reaction. Here, we teach the identification of BioH as the *E. coli* carboxylesterase that hydrolyzes DMB-S-MMP into DMB-S-MPA. By constructing a ΔbioH derivative of the LovD overexpression strain, we completely eliminated the competing reaction and further improved the robustness of the whole-cell biocatalytic synthesis of simvastatin acid.

Materials, Strains and Plasmids

Monacolin J and DMB-S-MMP were prepared as described previously (see, e.g., Xie et al., (2007) Appl Environ Microbiol 73: 2054-2060). All reagents were purchased from standard sources. The BL21(DE3) strain [F– omp hsdSB (rB– mB–) gal dcm λ(DE3)] was obtained from Novagen. The Keio collection was obtained from the National Institute of Genetics, Japan (see, e.g., Baba et al., (2006) Mol Syst Biol 2: 2006 0008). The single-gene knockout mutants were derived from the BW25113 strain [rrnB3 DElacZ4787 hsdR514 DE(araBAD)567 DE(rha-BAD)568rph-1]. WA837 (rB–, mB+, gal met), an *E. coli* B strain that is restriction-minus and modification-plus was obtained from The Coli Genetic Stock Center (CGSC) (see e.g., Wood, W. B. (1966). J Mol Biol 16: 118-133). The plasmids pAW31(kanr) and pXK8 (kanr) were derived from pET28a and contain the lovD gene from *A. terreus* and the bioH gene from *E. coli*, respectively.

Whole-Cell Based Hydrolysis Assay

The selected 57 mutants from the Keio collection together with BW25113, BL21(DE3) and BL21(DE3)/pAW31 were grown to saturation in a 96-well deep well plate in 1 mL LB media at 37° C. Neat DMB-S-MMP (5 µL) was added to each culture with a final concentration of 20 mM. After shaking (20° C., 300 rpm) for 10 hours, each culture was extracted with an equal volume of ethyl acetate (EA)/1% acetic acid (AcOH). The organic phase was dried, redissolved in 20 µL acetonitrile (CH3CN), and 1 µL was spotted on a TLC plate (silica gel 60 F254). The TLC plates were developed with 20% EA in hexane and visualized with iodine.

Analysis of the compounds were also performed with HPLC using an analytical C18 column (Alltech Apollo 5u, 150 mm×4.6 mm); linear gradient: 60% CH3CN in water (0.1% trifluoroacetic acid [TFA]) to 95% CH3CN in water (0.1% TFA) over 5 min, 95% CH3CN in water (0.1% TFA) for 10 minutes, with a flow rate of 1 mL/min. HPLC retention times (tR) were as follows: MJ lactone form: 3.40 min; DMB-S-MPA: 3.82 min; DMB-S-MMP: 6.80 min; simvastatin lactone form: 8.45 min. Both MJ and simvastatin acids were lactonized before HPLC analysis.

Purification of BioH and Enzymatic Assay

The bioH gene was amplified from *E. coli* genomic DNA by PCR with flanking restriction sites NdeI and EcoRI using the primers 5'-AACATATGAATAACATCTGGTGGCA-3' (SEQ ID NO: 5) and 5'-AAGAATTCTACACCCTCTGC-TICAACG-3' (SEQ ID NO: 6). The gene cassette was digested and ligated into pET28a to yield the expression construct pXK8. The *E. coli* BL21(DE3) strain transformed with pXK8 was grown in LB medium at 37° C. to an OD600 of 0.5, at which time 0.1 mM IPTG was added to the culture and expression was performed at 20° C. for 16 hours. Cells were resuspended in Buffer A (50 mM Tris-HCl, pH 8.0, 2 mM DTI, 2 mM EDTA) and lysed with sonication. Purification of BioH was facilitated by the N-terminal 6×His tag and Ni-NTA resin (Qiagen). Nearly pure (>95%) BioH was eluted in Buffer A containing 250 mM imidazole, which was buffer exchanged into Buffer A, concentrated, aliquoted and flash frozen.

The hydrolysis assays were performed at room temperature in 50 mM HEPES, pH 7.9. The thioester substrate DMB-S-MMP was added to final concentration between 0.1 mM and 1.0 mM. To facilitate solubilization of DMB-S-MMP, DMSO was added to a final concentration of 10% for all the samples. The reaction was initiated with the addition of BioH (0.01 µM) and quenched at desired time points (10, 20, 30 minutes) by adding equal volume of EA/1% AcOH. The organic phase was separated, dried and redissolved in 20 µL of ACN and analyzed with HPLC. The conversions of DMB-S-MMP to DMB-S-MPA were quantified by integration of the peaks at 234 nm. Comparison of the BioH catalytic efficiency towards the three dimethylbutyryl thioesters were performed at 1 mM substrate concentration and 10 nM BioH concentration.

P1 Transduction

Following standard protocols (see e.g., Miller, J. H. (1992) A short course in bacterial genetics: A laboratory manual and handbook for *Escherichia coli* and related bacteria. Cold Spring Harbor, N.Y.: Cold Spring Harbor Press), P1 transduction was used to construct the ΔbioH deletion mutant of BL21(DE3). Because of the different restriction system between *E. coli* K strain (BW25113) and B strain (BL21), the B strain WA837 (rB−, mB+) was used as an intermediate host for transduction. The ΔbioH::FRT-kan-FRT marker was first transduced from JW3375 to WA837 to yield YT0 (WA837 ΔbioH::FRT-kan-FR1). Using BL21(DE3) as a recipient and YT0 as a donor, strain YT1 (BL21 ΔbioH::FRT-kan-FRT λ(DE3)) was constructed. The YT1 strain was transformed with the helper plasmid pCP20 which contains a temperature sensitive replication and thermally inducible FLP gene (see e.g., Datsenko et al., (2000) Proc Natl Acad Sci USA 97: 6640-6645; and Wanner, 2000). Removal of the kan marker to yield YT2 ((BL21 ΔbioH:: FRT λ(DE3)) followed published procedures (see e.g., Datsenko et al., (2000) Proc Natl Acad Sci USA 97: 6640-6645; and Wanner, 2000).

PCR was used to verify the genetic changes of YT2. Three primers were designed. The primers B1: 5'-TGACGGCT-TCGCTATCCCAT-3' (SEQ ID NO: 7); B2: 5'-TACAC-CCTCTGCTTCAACG-3' (SEQ ID NO: 8); and B3: 5'-GCTGGATTGTTfCGCCGATC-3' (SEQ ID NO: 9) anneal to the upstream gene yhgA, the 3' end of bioH that was left intact, and the downstream gene gntX, respectively. The expected products for PCR reaction using YT2 genomic DNA as template are: B1/B2: 602 bp; B1/B3: 1002 bp. The expected products for PCR reaction using BL21(DE3) genomic DNA as template are: B1/B2: 1271 bp; B1/B3: 1771 bp. The expected PCR products were observed for each strain.

Whole Cell Biocatalysis

Whole-cell catalytic synthesis of simvastatin acid from MJ acid and DMB-S-MMP were performed as described (see, e.g., Xie et al., (2007) Appl Environ Microbiol 73: 2054-2060). The *E. coli* BL21(DE3)/pAW31 and YT2/pAW31 strains were cultured side-by-side for comparison. A single colony of the freshly transformed strains was used to inoculate a 5 mL LB culture supplemented with 35 mg/L kanamycin and grown overnight at 37° C. The next morning, 100 μL of the overnight culture was inoculated into 50 mL cultures containing LB broth, F1 minimal medium and F1 medium supplemented with 0.15 mg/L biotin. Growth rates were monitored by periodically measuring the OD600 reading. When OD600 reached ~0.5, 100 μM IPTG was added to the culture and expression of LovD was performed at 20° C. for 16 hours. To mimic high density fermentation conditions, the cells were concentrated 10-fold before addition of substrates. Typically, a 14 mL aliquot of the culture was transferred to a 15 mL centrifuge tube and the cells were collected by centrifugation (4° C., 4000 g, 10 minutes). The cell pellet was gently resuspended in 1316 μl of the supernatant, followed by addition of 84 μl of a MJ acid stock solution (250 mM in $H_2O$) (final concentration 15 mM). The concentrated culture was then separated into seven 200 μL samples and 1.2 μL of pure DMB-S-MMP was added to each sample (final concentration 25 mM). The culture was then shaken at 300 rpm at room temperature. At each time point, a total extraction was performed by adding 10 μL, 20% SDS to lyse the cells, followed by liquid-liquid extraction with 500 μL EA/1% AcOH. The organic phase was removed, evaporated, and redissolved in 50 μL ACN for HPLC analysis. For the BL21(DE3) sample, an additional 1.2 μL aliquot of DMB-S-MMP was added after 12 hours to replenish the hydrolyzed substrates.

Identification of BioH as the DMB-S-MMP Esterase

We first aimed to identify the *E. coli* enzyme that is responsible for the observed hydrolysis of DMB-S-MMP into DMB-S-MPA during fermentation. When different acyl carriers such as dimethylbutyryl-S-ethyl mercaptopropionate (DMB-S-EMP) and dimethylbutyryl-S-methyl thioglycolate (DMB-S-MTG) were used as the thioester substrate, we observed the corresponding hydrolyzed carboxylic acids in the fermentation broth. This suggests the responsible enzyme is an esterase or hydrolase with relaxed substrate specificity towards ester functionalities.

We used a high-throughput approach to identify the responsible enzyme, utilizing the *E. coli* K-12 in-frame single gene knockout mutant library (Keio Collection) (see e.g., Baba et al., (2006) Mol Syst Biol 2: 2006 0008). We reasoned that any mutant strain that is unable to hydrolyze DMB-S-MMP is directly due to the specific gene deletion. Examination of *E. coli* genome annotations (see e.g., Blattner et al., (1997) Science 277: 1453-1474) reveals 23 esterases/esterase-like enzymes, 94 hydrolases/hydrolase-like enzymes, and 16 acyltransferases (133 total candidate genes). Enzymes with confirmed activities and substrates that are unlikely to be involved in DMB-S-MMP hydrolysis were not examined in the first round of assays. The list of 57 BW25113 mutant strains examined are shown in Table 2.

Figure 14:
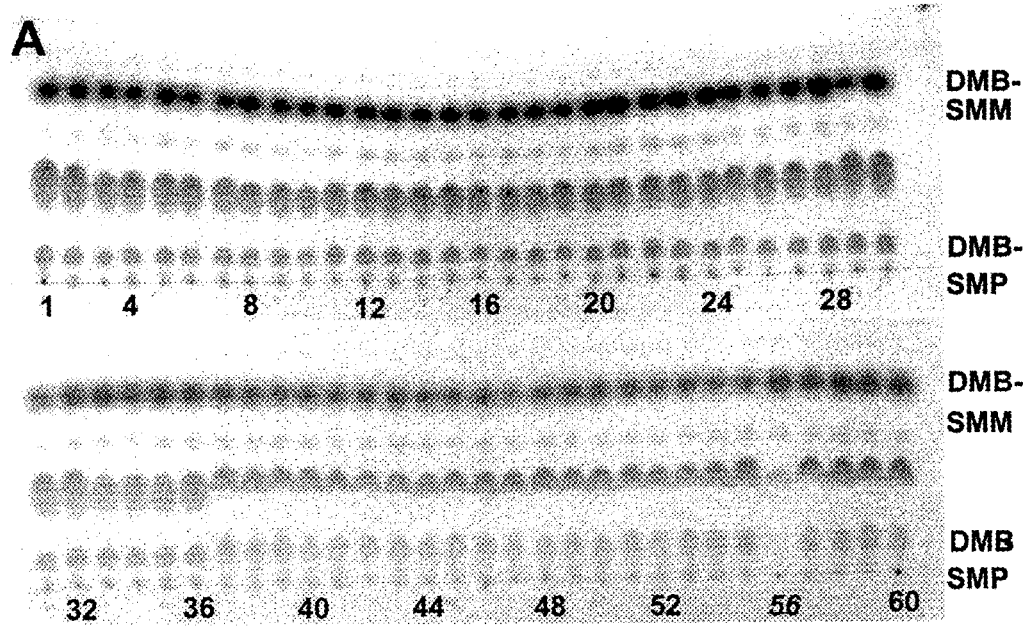
FIG. 14. (A) Thin layer chromatography showing the organic extracts of sixty *E. coli* strains supplemented with DMB-S-MMP. The strains identifications can be found in Table 2. The TLC plate was developed with 20% EA in hexane to separate DMB-S-MMP (top) and DMB-S-MPA (bottom). The middle spot is an unknown compound. In all strains except #56, DMB-S-MMP was hydrolyzed to DMB-S-MPA after 10 hours of incubation. The ΔbioH strain did not hydrolyze DMB-S-MMP. (B) Confirmation of TLC results using HPLC. No DMB-S-MPA can be detected in the extract of ΔbioH strain. The spectra were collected at 234 nm.
Figure 14:
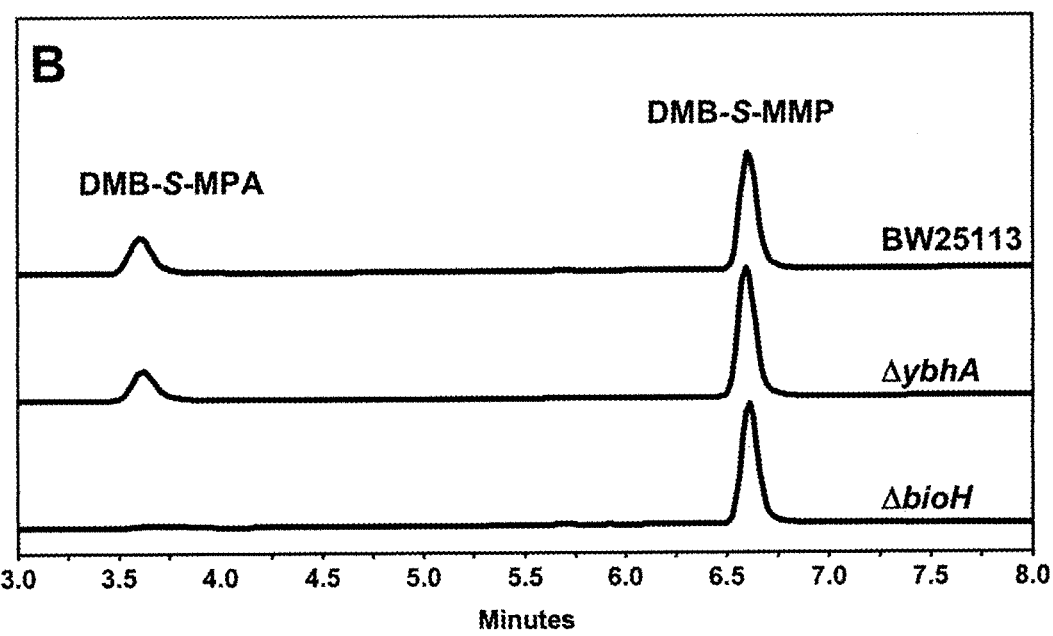

The mutants, wild type BW21113 and BL21(DE3) were grown to saturation in LB broth in a 96-well plate. We added 5 μL of neat DMB-S-MMP to each culture (1 mL) and the plate was shaken vigorously for 10 additional hours at room temperature. The cultures were acidified, extracted with ethyl acetate, and the organic phases were analyzed by thin layer chromatography (TLC) using a mobile phase (20% ethyl acetate in hexane) that enabled separation of DMB-S-MMP and DMB-S-MPA (FIG. 14A). The wild type BW25113 (lane 58) and BL21(DE3) (lane 59) each showed a comparable level of substrate hydrolysis and accumulation of DMB-S-MPA. All of the mutants examined displayed hydrolytic activity towards DMB-S-MMP, except ΔbioH (lane 56, strain JW3357). This surprising finding suggests that BioH (see e.g., O'Regan et al., (1989) Nucleic Acids Res 17: 8004), which is involved in the biosynthesis of biotin (vitamin H), may be the sole enzyme responsible for the observed hydrolysis in vivo. Additional examination using HPLC further confirmed that DMB-S-MPA cannot be detected in the organic extract of the ΔbioH mutant, while nearly 30% were hydrolyzed in bioH+ strains (FIG. 14B).

Verification of BioH Properties In Vitro

To prove that BioH is directly involved in hydrolyzing DMB-S-MMP during fermentation, we cloned the bioH gene and expressed it as an N-his-tagged protein from BL21(DE3) (see e.g., Tomczyk et al., (2002) FEBS Lett 513: 299-304). The protein was purified to homogeneity using Ni-NTA affinity chromatography with a final yield of 9 mg/L. The catalytic properties of BioH towards DMB-S-MMP were assayed and the extent of hydrolysis was measured by HPLC (234 nm). BioH exhibited Michaelis-Menten kinetics towards DMB-S-MMP and the kcat and Km values were determined to be 260±45 sec-1 and 229±26 μM, respectively (FIG. 15A).

Figure 15:
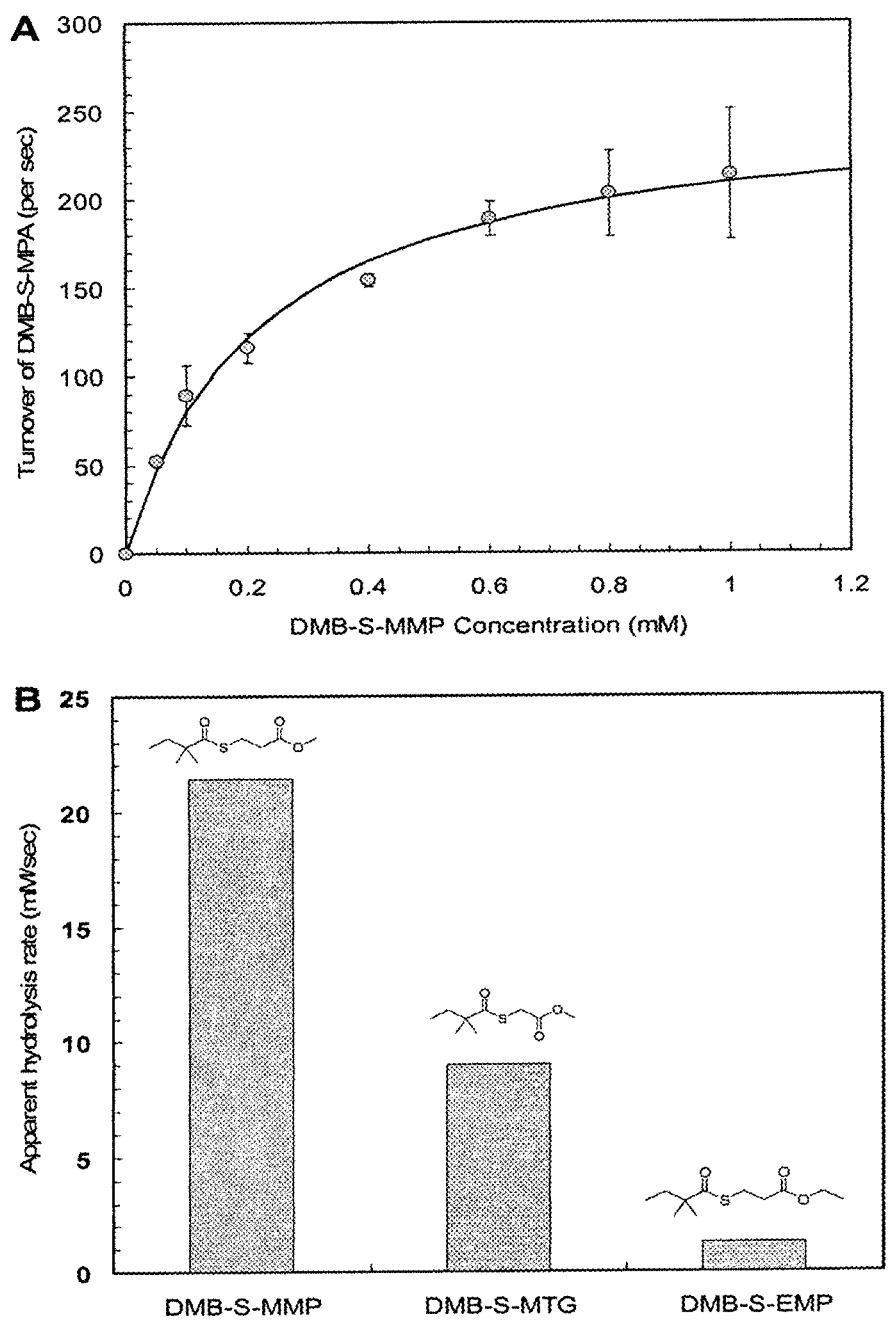
FIG. 15. (A) Michaelis-Menten kinetics of BioH towards DMB-S-MMP. The results are averaged for three runs. The kcat and Km values are 260±45 sec-1 and 229±26 μM, respectively. The high standard deviation observed at high DMB-S-MMP concentration may be due to the poor solubility of the substrate in buffer (50 mM HEPES, pH 7.9, 10% DMSO). (B) Comparison of hydrolysis rates for three different dimethylbutyryl thioesters. The reactions were performed with 1 mM thioester and 10 nM BioH.

The activities of BioH towards other dimethylbutyryl thioesters were also examined using the HPLC assay and are shown in FIG. 15B. Under identical reaction conditions (1 mM substrate, 10 nM BioH), we observed that BioH displayed most the potent esterase activity towards DMB-S-MMP. Decreasing the carboxylic acid backbone length by one carbon led to a 2.5-fold decrease in the rate of hydrolysis (DMB-S-MTG), while increasing the size of the ester moiety to an ethyl ester significantly attenuated the rate of substrate hydrolysis (DMB-S-EMP). These observations are consistent with the in vivo result, where both substrates were hydrolyzed in the presence of cells, albeit to lesser extents than DMB-S-MMP.

BioH is an essential enzyme in the biosynthesis of biotin in *E. coli* (see e.g., Lemoine et al., (1996) Mol Microbiol 19: 645-647). It has been proposed that BioH is responsible for synthesizing pimeloyl-CoA (see e.g., Guillen-Navarro et al., (2005) FEMS Microbiol Lett 246: 159-165), but its exact biochemical function has not been confirmed. Interestingly, the crystal structure of *E. coli* BioH has been determined to 1.7 Å resolution in an effort to predict protein function from structural features (see e.g., Sanishvili et al., (2003) *J Biol Chem* 278: 26039-26045). High throughput structural analysis unveiled a catalytic triad in BioH that is also found in known hydrolases, which hinted BioH may possess hydrolytic activity. Assays using p-nitrophenol esters showed that BioH displays carboxylesterase activities with preference towards short chain fatty acid esters (see e.g., Sanishvili et al., (2003) J Biol Chem 278: 26039-26045). Our work, both in vivo and in vitro, further elaborates the biochemical properties of BioH and shows that the enzyme has very broad substrate specificity towards esters moieties. In contrast, BioH displayed no thioesterase activities towards the thioester bond present in the substrates analyzed in this work. No further degradation of the hydrolyzed thioester acids were observed.

Construction of BL21(DE3) ΔBioH Mutant YT2

After identification and verification of BioH as the enzyme responsible for hydrolyzing DMB-S-MMP during fermentation, it was evident that a BioH deficient *E. coli* strain should be used as the host for whole cell biosynthesis of simvastatin acid. We constructed various expression vectors of LovD that does not require the T7 polymerase and transformed them into JW3357. Evaluation of simvastatin acid bioconversion rates in these strains showed the LovD activity is significantly lower than that of BL21(DE3)/pAW31. The slower reaction velocities are largely attributed to the lowered expression levels of LovD in these host/vector combinations, as determined by SDS-PAGE. As a result, we concluded that a ΔbioH derivative of BL21(DE3) is needed for achieving maximum conversion rates, while eliminating substrate hydrolysis.

Each of the Keio Collection single-gene knockout mutants contained a kanamycin resistance gene in place of the target gene (see e.g., Baba et al., (2006) Mol Syst Biol 2: 2006 0008). The marker is flanked by FRT sites which facilitates facile removal of the marker by the FLP enzyme. We used P1 transduction to move the ΔbioH::FRT-kan-FRT marker from JW3357 to BL21(DE3). Due to the restriction differences between the donor K strain and the recipient B strain, we used *E. coli* WA837 (restriction-minus, modification-plus) as an intermediate host for P1 transduction (see e.g., Dien et al., (2001) J Ind Microbiol Biotechnol 27: 259-264). After transplanting the marker into BL21(DE3) to yield YT1, the helper plasmid pCP20 which contains a temperature sensitive replicon and a thermally inducible FLP gene (see e.g., Datsenko et al., (2000) Proc Natl Acad Sci USA 97: 6640-6645; and Wanner, 2000), was used to remove of the kan gene to yield YT2 (BL21(DE3) ΔbioH:: FRT). PCR analysis using primers annealing to the upstream and downstream regions confirmed deletion of bioH, as well as removal of the kan marker (data not shown).

YT2 was then cultured in LB medium and the DMB-S-MMP hydrolysis assay was performed. As expected, the new strain catalyzed no detectable hydrolysis of the thioester and no trace of DMB-S-MPA can be found in the culture broth. DMB-S-MMP can be nearly quantitatively recovered from the saturated culture that had been grown for >24 hours, reassuring that the substrate can remain intact through prolonged fermentation using this strain.

Whole-Cell Biocatalysis Using YT2

Figure 16:
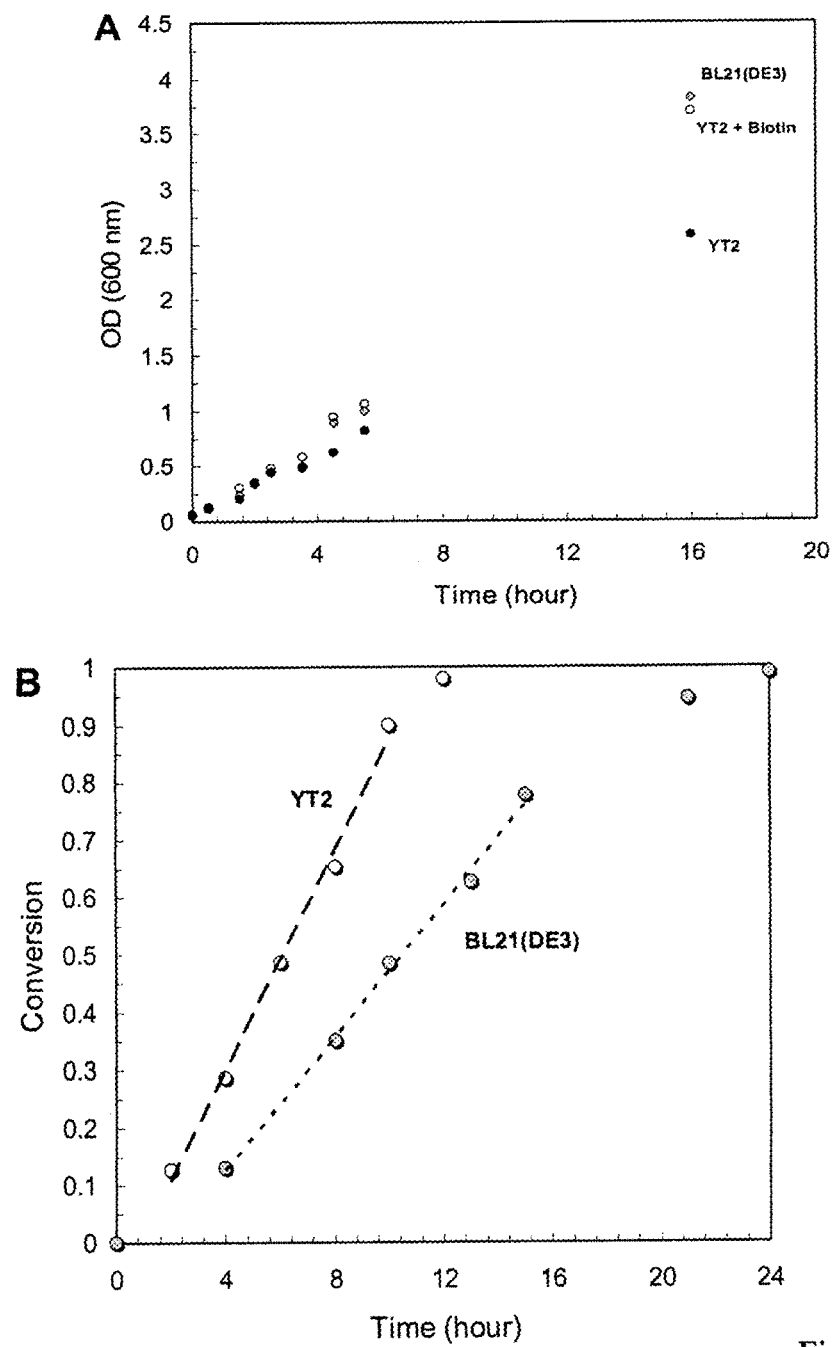
FIG. 16. (A) Comparison of growth rates and final cell density for BL21(DE3)/pAW31 (grey 0) and YT2/pAW31 (without biotin: 0; with 0.15 mg/L biotin: ●) in F1 minimal media. Cells were grown to OD600 ~0.5, induced with 100 μM IPTG and shifted to a 20° C. shaker for 12 hours. The ΔbioH strain YT2 requires addition of exogenous biotin to maintain robust cell growth in synthetic medium. (B) Comparison of simvastatin conversion as a function of time (15 mM MJ, 25 mM DMB-S-MMP). YT2/pAW31 (○) is significantly faster than BL21(DE3)/pAW31 (●) (data taken from Xie et al., (2007) Appl Environ Microbiol 73: 2054-2060) in reaching 99% conversion. Both strains displayed a lag phase immediately following substrate addition (0 hour) and a lag phase near reaction completion. The reaction velocities between the lag phases are linear. The conversion rate for YT2/pAW31 (1.5 mM/hr) is twice as fast as that for BL21(DE3) (0.75 mM/hr)

We first examined the viability of YT2 as a host for the whole cell biocatalytic synthesis of simvastatin acid. The expression plasmid pAW31 was transformed into YT2 via electroporation to yield YT2/pAW31. BL21(DE3)/pAW31 and YT2/pAW31 were each grown to OD600 of 0.5, followed by induction of protein synthesis with 100 μM IPTG at 20° C. for up to 16 hours. The two strains exhibited identical growth kinetics when LB media was used, reaching the same OD600 (3.9-4.0) at the end of protein expression period. When F1 minimal medium was used, the two strains grew comparably before induction (FIG. 16A). In contrast, YT2/pAW31 grew considerably slower than BL21(DE3)/pAW31 in medium without biotin supplementation after induction. The post-induction cell density for the mutant strain was ~60% of the parent strain. We attributed the retarded growth rate to the inability of YT2/pAW31 to synthesize biotin and support robust cell growth in the minimal medium. When YT2/pAW31 strain was grown in F1 medium supplemented with 0.15 mg/L biotin, the growth kinetics of the mutant strain were indistinguishable from that of BL21(DE3)/pAW31.

We then compared the efficiency of YT2/pAW31 to BL21(DE3)/pAW31 in the whole cell assay. Both strains were grown in LB medium and were concentrated ten-fold to mimic a high cell density environment after 12 hours of LovD expression. MJ acid and DMB-S-MMP were added to final concentrations of 15 mM and 25 mM, respectively, to initiate the bioconversion. FIG. 16B shows that YT2/pAW31 was significantly more efficient in the assay as a result of bioH deletion. Complete conversion (>99%) was observed for the mutant strain in less than 12 hours of incubation with no trace of DMB-S-MMP hydrolysis. In contrast, BL21 (DE3)/pAW31 achieved the same conversion in 24 hours, while requiring addition of another 25 mM of DMB-S-MMP during the fermentation as a result of substrate hydrolysis. During the linear range of the reaction, YT2/pAW31 synthesized simvastatin acid at a rate of 1.5 mM/hour, significantly higher than the 0.75 mM/hour measured for BL21 (DE3)/pAW31 (see, e.g., Xie et al., (2007) Appl Environ Microbiol 73: 2054-2060). Using YT2/pAW31, we were also able to decrease the minimal concentration of DMB-S-MMP required to drive the reaction to completion. Complete conversion to simvastatin acid can be achieved with identical rates when the initial DMB-S-MMP (18 mM) to MJ acid (15 mM) molar ratio was as low as 1.2.

The enhancement in rate is largely due to the increased intracellular concentration of DMB-S-MMP in the absence of BioH. From the in vitro studies, we showed that BioH is extremely rapid in hydrolyzing DMB-S-MMP. Therefore, even at low intracellular concentrations of BioH, the substrate hydrolysis reaction can compete for the pool of substrates that are present in the cytoplasm. Maintaining elevated intracellular concentration of DMB-S-MMP is critical, especially considering LovD can catalyze the reversible reaction in which simvastatin acid can be hydrolyzed to MJ acid in the absence of acyl thioester donors (see e.g., Xie et al., (2006) Chem Biol 13: 1161-1169).

Figure 17:
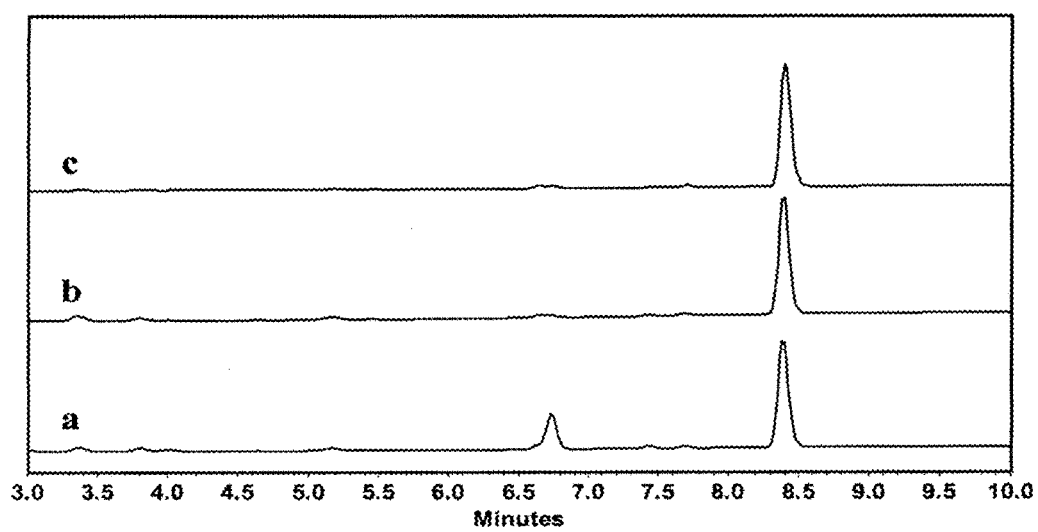
FIG. 17. HPLC analysis (238 nm) of simvastatin purification steps. Simvastatin acid is lactonized to simvastatin prior to injection. Trace a: crude extract (combined culture broth and cell extract) of YT2/pAW31 after completion of reaction (99% MJ acid conversion to simvastatin acid). The peak at 6.80 is the DMB-S-MMP; Trace b: Crude sample after washing with equal volume of hexane to remove unreacted DMB-S-MMP and precipitation; Trace c: Purified simvastatin after washing with dH2O and solubilization in ACN. The small peak seen at 6.7 minutes is simvastatin acid that is not completely lactonized (~1%).

Purification of simvastatin acid after bioconversion was also improved as demonstrated by working up a scaled-up fermentation of YT2/pAW31 (200 mL, 15 mM MJ, 18 mM DMB-S-MMP). After verification of complete conversion of MJ acid into simvastatin acid by HPLC (FIG. 17, trace a), the combined fermentation broth and cell extract was washed with hexane, acidified with 6 M HCl and filtered to collect the precipitated simvastatin acid (trace b). After washing the filter cake with 1 volume of dH2O, simvastatin acid was solublized in ACN, filtered and analyzed by HPLC (trace c). No additional washing steps were required to remove DMB-S-MPA that was present in BL21(DE3)/pAW31. The final recovery of simvastatin acid using this approach was 94%.

Conclusion

As illustrated above, we have used Keio single-gene knockout library to identify BioH as the carboxylesterase that hydrolyzes DMB-S-MMP during whole cell biocatalytic conversion of simvastatin acid from MJ acid. BioH exhibits very rapid hydrolysis rates, which depletes the intracellular concentration of DMB-S-MMP available as an acyl donor in the LovD-catalyzed transesterification. Using the bioH expression strain YT2, we were able to completely eliminate degradation of DMB-S-MMP and significantly increase the robustness of the whole cell biocatalyst. This strain may be a useful host in other precursor directed biosynthesis and biocatalysis applications where one or more substrates used contains a labile ester linkage (see e.g., Murli et al., (2005) *Appl Environ Microbiol* 71: 4503-4509).

Example 4: Efficient Synthesis of Simvastatin Using Whole-Cell Biocatalysis

This example describes a one-step, whole cell biocatalytic process for the synthesis of simvastatin from monacolin J. As discussed in detail below, using an *Escherichia coli* strain overexpressing *A. terreus* LovD, we were able to achieve >99% conversion of monacolin J to simvastatin without the use of any chemical protection steps. A key finding was a membrane permeable substrate, α-dimethylbutyryl-S-methyl-mercaptopropionate (DMB-S-MMP), that was efficiently utilized by LovD as the acyl donor. The process was scaled up for gram-scale synthesis of simvastatin. We also demonstrate that simvastatin synthesized via this method can be readily purified from the fermentation broth with >90% recovery and >98% purity as determined by HPLC. Bioconversion using high cell density, fed-batch fermentation was also examined. The whole cell biocatalysis can therefore be an attractive alternative to the current, multistep semisynthetic transformations.

Figure 18:
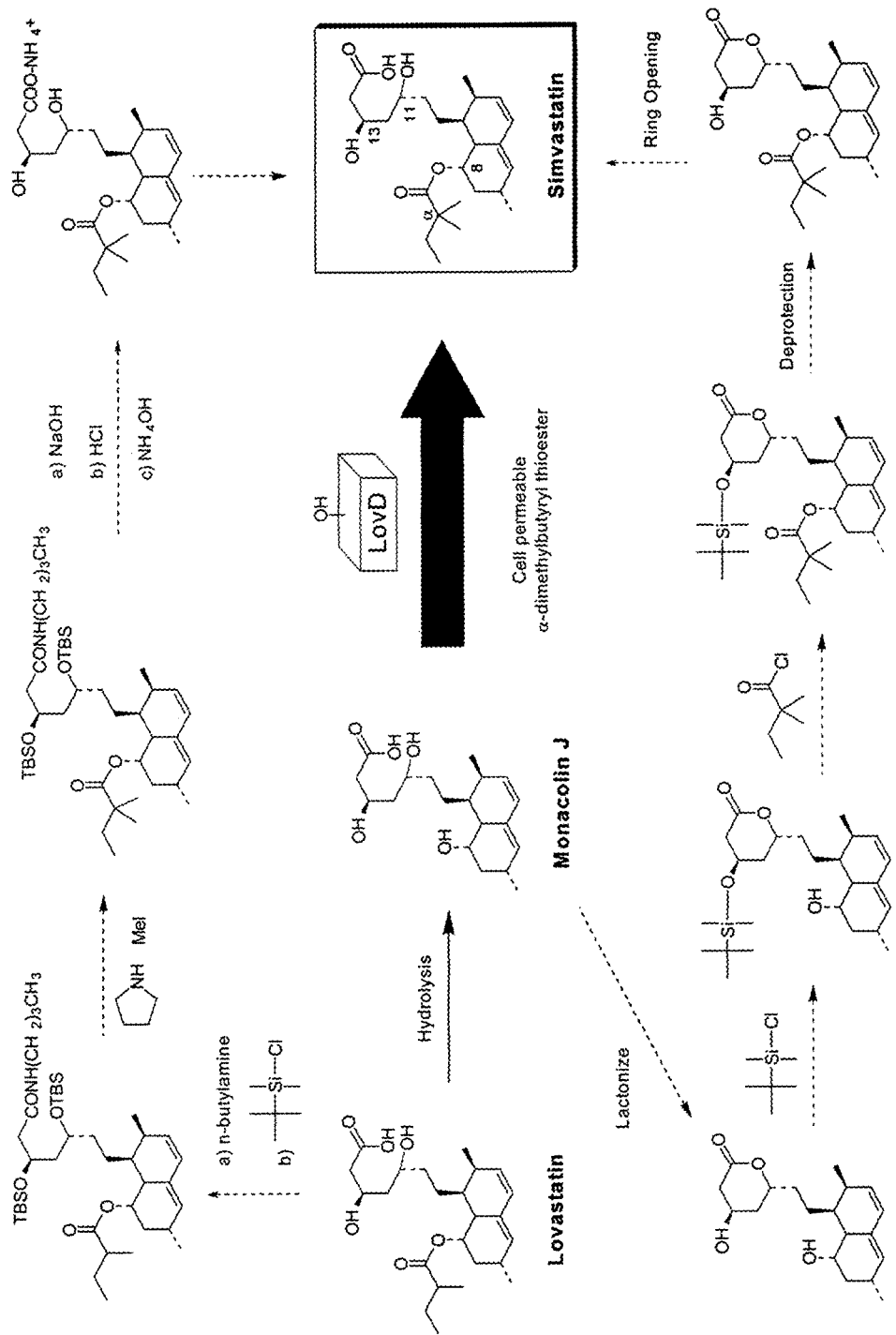
FIG. 18. The chemical structures of lovastatin acid, monacolin J acid and simvastatin acid. The biocatalytic reaction studied is the enzymatic conversion of monacolin J to simvastatin (block arrow). LovD is able to regioselectively acylate the C8 hydroxyl group. Two commonly used semi-synthetic processes are shown in dashed arrows.

Currently, two semisynthetic processes (see, e.g., Askin et al., 1991, J. Org. Chem. 56; and Hoffman et al., 1986 J Med Chem 29:849-52) are widely used to synthesize simvastatin starting from lovastatin (FIG. 18). One commonly adapted process (see e.g., Hoffman et al., 1986 J Med Chem 29:849-52) starts with the hydrolysis of lovastatin to yield the key intermediate monacolin J, followed by lactonization of the acid to protect the C11 hydroxyl group, and trimethylsilylation protection of the C13 hydroxyl. The protected monacolin J is then subjected to acylation by α-dimethylbutyryl chloride to yield the protected form of simvastatin, which is subsequently deprotected to yield simvastatin. Both multistep processes shown in FIG. 18 are laborious, thus contributing to simvastatin being nearly five times more expensive than lovastatin. Therefore, a new semisynthetic scheme that can decrease the number of chemical transformations and increase the overall efficiency of the conversion can be of significant utility.

We have previously described cloning and characterization of a dedicated acyltransferase from the lovastatin biosynthetic gene cluster that regioselectively transfers the α-methylbutyryl group from the lovastatin diketide synthase (LDKS) to the C8 hydroxyl group of monacolin J to yield lovastatin (see, e.g., Xie et al., 2006, Chem Biol 13: 1161-1169). We demonstrated that LovD has broad substrate specificity towards the acyl carrier, the acyl group and the decalin core. Most notably, LovD was able to catalyze the direct acylation of monacolin J by α-dimethylbutyryl-S—N-acetylcysteamine (DMB-S-NAC) to afford simvastatin. The reaction is highly regiospecific towards the C8 alcohol only, and is therefore a potential one-step process to produce simvastatin from monacolin J without employing protective chemistry.

In this Example, we describe the development of a whole-cell biocatalytic process that is able to convert monacolin J to simvastatin in a highly efficient manner. Using a novel thioester as the acyl donor, we were able to achieve >99% conversion of simvastatin from monacolin J in a single step. The fermentation process can be easily scaled up to produce industrial-scale yield of simvastatin.

Synthesis of α-dimethylbutyryl-S-methyl 3-mercaptopropionate (DMB-S-MMP)

Dimethylbutyryl chloride (1.76 mL, 12 mmol) was added slowly to a 50 mL solution of methyl-3-mercaptopropionate (1.30 mL, 12 mmol) and triethylamine (3.340 mL, 24 mmol) in diethyl ether at 0° C. and the solution was stirred for 2 hours. The reaction was quenched with aqueous NH4Cl and extracted with 100 mL ethyl acetate twice. The organic layer is combined, dried, and evaporated to give a colorless liquid (2.6 g). The residue was purified with silica-gel chromatography (EA/hexane, 20/80) to yield pure DMB-S-MMP (2.35 g, 90% yield). 1H NMR: δ 3.87 (s, 3H), 3.09 (t, 2H, 7.1 Hz), 2.58 (t, 2H, 7.0 Hz), 1.59 (q, 2H, 7.5 Hz), 1.18 (s, 6H), 0.83 (t, 3H, 7.4 Hz); 13C NMR: δ 206.16, 172.26, 51.81, 50.04, 34.38, 33.73, 24.71, 23.60, 8.92.

Kinetic Assay of lovD Assay:

Expression and purification of LovD has been previously described in detail (see, e.g., Xie et al., 2006, Chem Biol 13: 1161-1169). The assays were performed at room temperature in 50 mM HEPES, pH 7.9. The initial velocities (ki) of the acyl substrates were determined with 10 μM LovD, 1 mM monacolin J and 4 mM of the thioester. The reaction mixture at different time points was quenched by trifluoroacetic acid (TFA), extracted with ethyl acetate, evaporated to dryness and redissolved in acetonitrile. The percent conversion of monacolin J to simvastatin was determined by HPLC analysis (C18). The linear range of the turnover rate is reported as ki in Table 1B. To determine the Km of DMB-S-MMP, the concentration of monacolin J is fixed at 2 mM, while the concentration of DMB-S-MMP was varied from 0.2 mM to 10 mM. DMSO is added to a final concentration of 5% to facilitate solubilization of DMB-S-MMP. To obtain Km of monacolin J, DMB-S-MMP concentration is fixed at 2 mM, while the concentration of monacolin J is varied from 0.2 mM to 5 mM.

Whole Cell Lysate Activity Assay

A whole cell lysate assay was used to determine the level of LovD activity under different fermentation conditions. For example, the *E. coli* BL21(DE3) strain transformed with pAW31 was grown in LB medium at 37° C. to an OD600 of 0.5, at which time 100 μM IPTG was added to the culture and expression was performed at room temperature (RT) for 16 hours. A 70 ml aliquot of the culture was then harvested by centrifugation (4000 g, 20 minutes). The supernatant was removed, and the cell pellet was resuspended in 7 ml lysis buffer (20 mM Tris-HCl, pH 7.9, 500 mM NaCl). Cells were lysed by sonication on ice and cell debris was removed by centrifugation (13,000 rpm, 10 minutes, 4° C.). The lysate is then directed added to the in vitro assay. Final assay condition: 50 mM HEPES, pH 7.9, 1 mM monacolin J, 4 mM DMB-S-MMP, 5 µl cell lysate, 25 µl final volume. The effective concentration of LovD in the fermentation broth was then calculated from the initial velocity using 0.6 min-1 as the turnover rate.

Low-Density Fermentation

The E. coli BL21(DE3)/pAW31 strain was grown in LB medium at 37° C. to an OD600 of 0.5, at which time 100 µM IPTG was added to the culture and expression was performed at RT for 16 hours. A 10 ml culture was transferred to a 15 mL centrifuge tube. The cells were collected by centrifugation (4000 g, 10 minutes). The cell pellet was resuspended in 957 µl of the supernatant. The pH was adjusted to pH 7.9 with 1.0 N NaOH, followed by addition of 33 µl 450 mM MJ (final concentration 15 mM) and 6 µl pure DMB-S-MMP (final concentration ~25 mM). The culture was then shaken at 300 rpm at room temperature. At each time point, a 4 µL aliquot was removed from the reaction mixture, quenched in 300 µL ethyl acetate containing 1% TFA. The organic phase was removed, evaporated, and redissolved in acetonitrile for HPLC analysis.

For larger scale synthesis of simvastatin, the above procedure was scaled up starting from 2×1 L shake flask culture of E. coli BL21(DE3)/pAW31 strain. After 16 hours of expression at RT, the culture volume was concentrated to 200 mL to a final OD600 of 22. Monacolin J (sodium salt form) and DMB-S-MMP were added to a final concentration of 15 mM and 25 mM, respectively. The cells were shaken at room temperature and HPLC was used to monitor the reaction progress. To purify the simvastatin from fermentation after the reaction has completed (>99% conversion as judged by HPLC), the following procedure was used. Cells were removed by centrifugation. The intracellular simvastatin was extracted by stirring the cell pellet in acetone. The acetone was then removed under reduced pressure and the residue was dissolved in dH2O and filtered. The filtrate and the clear fermentation broth were combined, washed with equal volume of n-hexane twice, and acidified to pH 2.0 with 6N HCl. The white precipitate was recovered by filtration and was washed excessively with ice-cold dH2O to remove the coprecipitated DMB-S-MPA. After drying of the filter cake under vacuum, the solids were stirred in 200 mL of acetonitrile for 1 hour, followed by filtration to remove insolubles. The filtrate was evaporated to dryness under reduced pressure to yield the acid form of simvastatin.

High Density F1 Fed-Batch Fermentation

The F1 fed-batch fermentation and media composition were adopted from Pfeifer et al (see e.g., Pfeifer et al., 2002, Appl Environ Microbiol 68:3287-92). We excluded the vitamin solution from both the fermentation medium and the feed medium. A starter culture was grown overnight in 5 ml of LB media (with 35 mg/L kanamycin) at 37° C. and 250 rpm and 1 mL was used to inoculate a 100 ml shake flask seed with F1 medium (with 35 mg/L kanamycin). 10 mL of the seed F1 culture was used to inoculate a 2-liter Applikon Biobundle vessel containing 1 L of F1 medium. Fermentation was conducted at 37° C. and the pH was maintained at 7.1 throughout the experiment with 1 M H2SO4 and half-concentrated NH4OH. Aeration was controlled at 0.2 to 0.4 L/min and agitation was maintained at 900 rpm. When the OD600 reading reaches between 5 and 10, the temperature of the fermentation was reduced to RT, followed by additional of 200 µM IPTG to induce protein expression. At the same time, a peristaltic pump delivered 0.08 mL/min of the feed solution to the fermentor.

Effective LovD activity and concentration at different stages of the fermentation were measured as described above. To prepare resting cells for bioconversion studies, the cells were centrifuged at 5000 g for 10 minutes, followed by gentle resuspension in the same volume of PBS buffer, pH 7.4. Monacolin J and DMB-S-MMP were then added to the cell aliquots to initiate the synthesis of simvastatin.

Results

Identification of a Kinetically Superior Acyl Donor

We previously showed that LovD can utilize membrane permeable thioesters as acyl donors in the transesterification reaction (see e.g., Xie et al., 2006, Chem Biol 13: 1161-1169). Both DMB-S-NAC and DMB-S-MTG (Table 1B) were shown to be substrates of LovD. The two substrates, however, both supported poor turnover in the synthesis of simvastatin, with apparent ki values ~0.02 per minute. In addition, when either substrate is utilized, the reaction suffered severe substrate inhibition at increasing concentrations of monacolin J. Therefore, the first priority in developing LovD into an industrially useful catalyst for the chembiosynthesis of simvastatin is to identify better substrates that can overcome these two limitations.

We synthesized several additional variants of DMB-S-MTG and assayed for the catalytic properties in vitro. DMB-S-methyl mercaptopropionate (DMB-S-MMP), DMB-S-ethyl mercaptopropionate (DMB-S-EMP) and DMB-S-methyl mercaptobutyrate (DMB-S-MMB) were each synthesized by reacting α-dimethylbutyryl chloride with the corresponding free thiols. The initial turnover rates are compared in Table 1B. Surprisingly, increasing the length of the thioester carrier by one carbon (from C2 in S-MTG to C3 in S-MMP and 5-EMP) significantly increased the turnover rate of the reaction. Inserting an additional carbon in S-MMB (C4) resulted in additional increase in the rate of transesterification. Under the standard reaction condition (1 mM MJ, 4 mM acyl substrate, 10 µM LovD, 50 mM HEPES, pH 7.9), the initial turnover rates of esterification are 0.6, 0.7, 0.78 min-1 for DMB-S-MMP, DMB-S-EMP and DMB-S-MMB respectively. The >30 fold increases in rates reflect the relative position of the carbonyl groups to the thioester linkage is critical for binding to LovD. In contrast, when DMB-S-MPA was used as the acyl donor, the initial turnover rate decreased significantly to 0.08 per min, indicating the free acid (likely a sodium salt of) binds poorly to LovD active site.

Figure 19A:
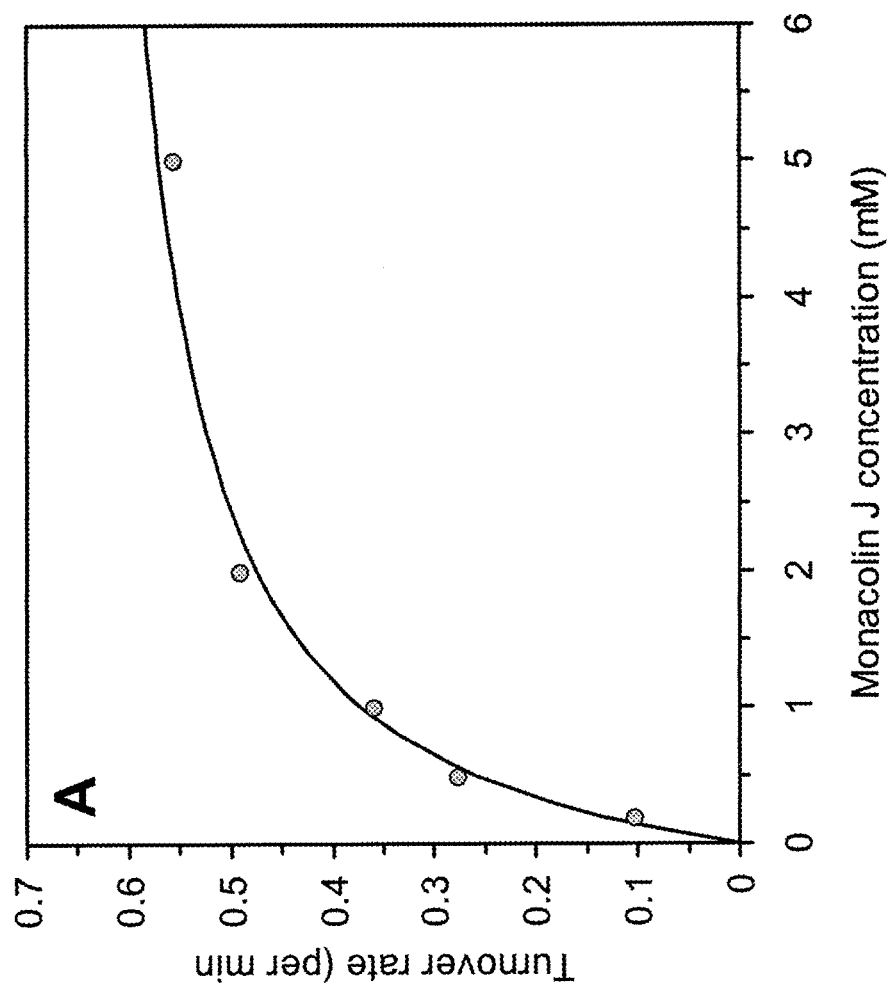
FIGS. 19A and 19B. Kinetic analysis of LovD catalyzed acylation of monacolin J to yield simvastatin using DMB-S-MMP as the acyl thioester. The y-axis is expressed as catalytic turnover (V/Eo) (FIG. 19A) Michaelis-menten kinetics of LovD as a function of monacolin J concentration, at a fixed DMB-SMMP concentration of 2 mM. No substrate inhibition is observed. Km (monacolin J)=0.78±0.12 mM.
Figure 19B:
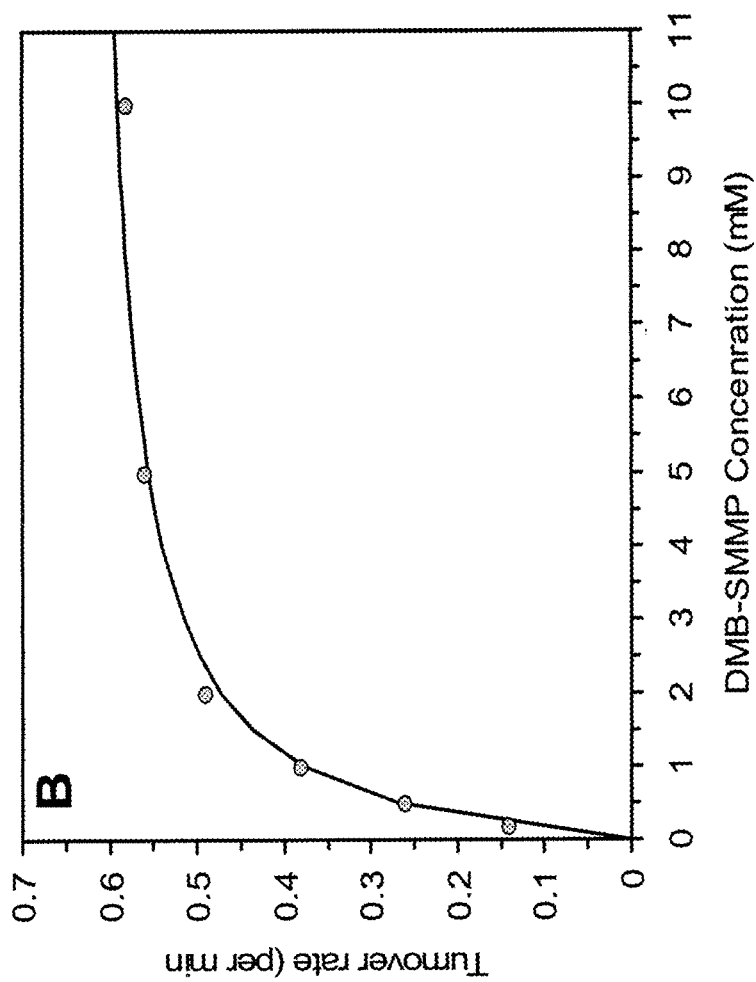

We chose DMB-S-MMP as the most suitable acyl thioester for biocatalysis because the precursor thiol (methyl mercaptopropionate) is significantly cheaper than the other starting materials. The kinetic parameters of the acylation reaction when DMB-S-MMP is used as the acyl donor were determined and are shown in FIG. 19. To obtain the Km values of either substrate in the transacylation reaction, we fixed the concentration of one substrate, while varying the concentration of the other substrate to obtain a Michaelis-Menten kinetics curve. FIG. 19A shows the reaction turnover rate (V/Eo) as a function of monacolin J concentration. In contrast to previously assayed substrates, no substrate inhibition by monacolin J is observed and the Km is determined to be 0.78±0.12 mM. The turnover rate of LovD at varying amounts of DMB-S-MMP is similarly determined by fixing the monacolin J concentration at 2 mM (FIG. 19B). The Km of DMB-S-MMP is shown to be 0.67±0.04 mM. In both titrations the kcat of the reaction is determined to be 0.66±0.03 min-1. Our kinetics analysis clearly demonstrates that DMB-S-MMP is a kinetically superior substrate compared to previously reported thioesters. The level of substrate inhibition in a Ping Pong Bi Bi reaction depends upon the relative Km of the two substrates. When DMB-S-MMP is used as an the acyl substrate, its relatively lower Km allows it to bind to LovD readily and is therefore not inhibited by increasing monacolin J concentrations. This important property therefore allows the development of a batch biocatalytic process in contrast to a fed-batch process in which the monacolin J has to be continuously supplied to keep its concentration low and minimize substrate inhibition.

We previously observed that acyl-S-MTG was rapidly hydrolyzed when added to an *E. coli* fermentation broth reaction (see e.g., Xie et al., 2006, Chem Biol 13: 1161-1169). To test the stability of the newly identified acyl donor under in vivo conditions, neat DMB-S-MMP was added to LB medium inoculated with *E. coli* BL21(DE3) cells and the culture was grown at 37° C. overnight (16 hours). We observed ~20% degradation of the substrate to a predominantly more polar compound. Compare to known compounds using HPLC, we identified the major degradation product to be DMB-S-MPA, which may arise through the action of endogenous *E. coli* lipases. We concluded that when DMB-S-MMP is supplied in excess in the batch reaction, the low extent of degradation will not limit the bioconversion of monacolin J to simvastatin.

Whole Cell Biocatalysis

Equipped with the significantly more efficient DMB-S-MMP thioester, we studied the conversion of monacolin J to simvastatin using *E. coli* as a whole-cell biocatalyst. A BL21(DE3) strain transformed with the pET28a derived expression plasmid pAW31 was used as the microbial host. Expression of LovD was performed for 16 hours at room temperature and the level of expression was visualized with SDS-PAGE. To quantify the active amount of LovD expressed under different growth conditions and media, we employed an activity assay in which the whole cell lysate was directly added to a reaction assay containing 1 mM monacolin J, 4 mM DMB-S-MMP in 50 mM HEPES, pH 7.9. The conversion of monacolin J to simvastatin was quantified by HPLC and the apparent concentration of LovD was estimated using the ki value of 0.6 min-1 (Table 1B). Under low cell density conditions, LovD is expressed almost three times higher from LB medium than F1 minimal medium (Table 3).

Figure 20A:
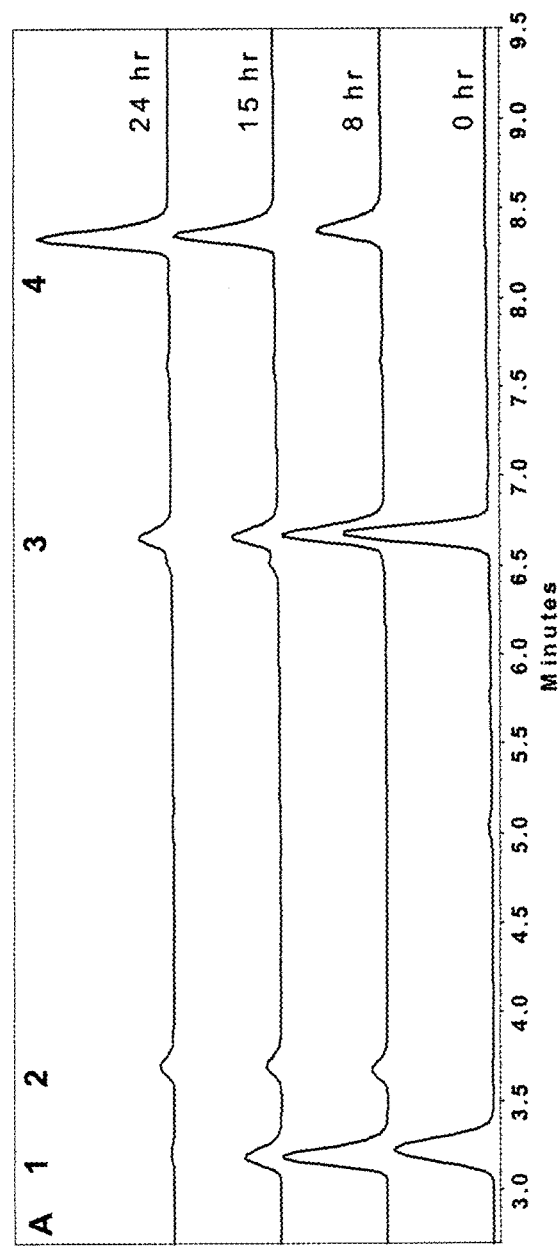
FIGS. 20A and 20B. Low density fermentation and biocatalysis. The *E. coli* strain BL21(DE3)/pAW31 expressing LovD overnight was concentrated 10× to a final OD600 of 22. The substrates monacolin J and DMB-S-MMP were added to a final concentrate of 15 and 40 mM, respectively. The conversion was followed as function of time by HPLC analysis.

We then tested the chembiosynthesis of simvastatin in LB medium. After overnight expression of LovD, a 10 mL aliquot of the cells was concentrated ten-fold to 1 mL in LB. The concentration step was performed to achieve a high cell density environment mimicking fermentation conditions and to obtain a higher effective concentration of LovD (final concentration approximately 20 µM). The sodium salt form of monacolin J was added to a final concentration of 15 mM (from a stock of 450 mM in water) and neat DMB-S-MMP was added to a final concentrate of 25 mM. The reaction mixture was then shaken rigorously at room temperature. Time points were taken periodically to check the conversion of monacolin J to simvastatin (FIG. 20A).

Figure 20B:
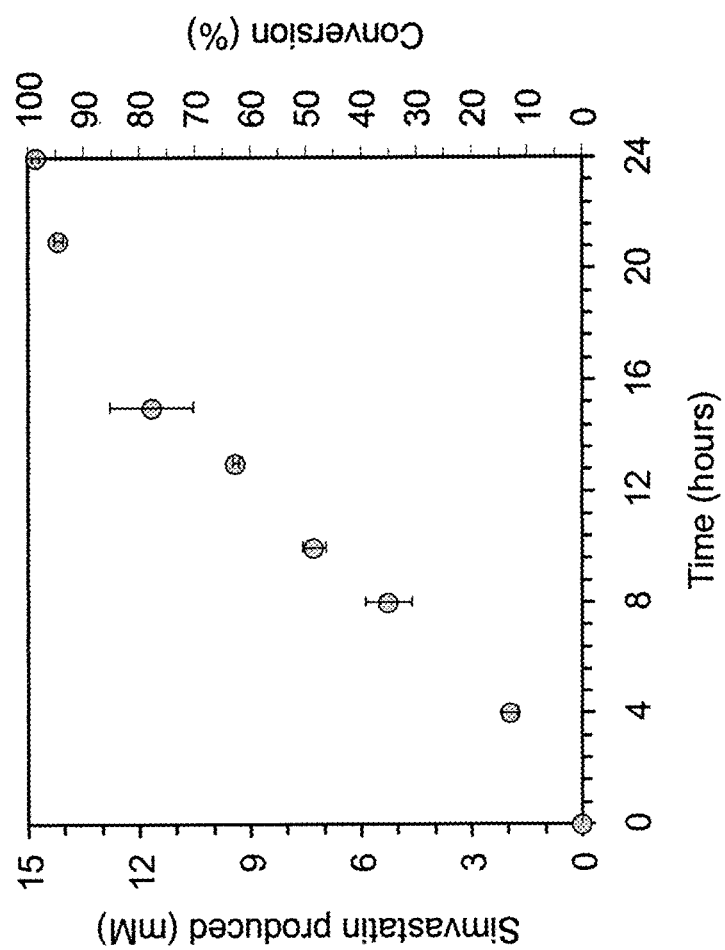

As shown in FIG. 20B, the simple, low density culture of BL21(DE3)/pAW31 was a robust whole cell biocatalyst for the synthesis of simvastatin. An initial lag phase of 2 hours was observed at the onset of adding the two substrates, followed by rapid conversion with a linear reaction velocity of ~0.73 mM per hour. The reaction rate slows at higher conversions (>95%) as the result of monacolin J depletion. Within 24 hours, 99% of monacolin J was converted to simvastatin. Based on HPLC analysis, no degradation of either monacolin J or simvastatin by cellular metabolism was observed. We observed ~20% decrease in the OD600 readings of the culture after 24 hours, suggesting the whole cell process may be maintained for prolonged catalysis.

We reported that LovD is able to hydrolyze lovastatin into monacolin J in vitro with a kcat of 0.21 min-1 reaction (see e.g., Xie et al., 2006, *Chem Biol* 13: 1161-1169). To examine whether we can couple the hydrolytic step together with the acylation step in a single fermentation run, we assayed the rate of lovastatin hydrolysis by BL21(DE3)/pAW31. Under the same in vivo conditions as above, we observed a slow rate of monacolin J formation. Starting with 0.5 mM lovastatin (sodium salt form), we achieved 91% hydrolysis in 48 hours, with a conversion rate of ~0.01 mM per hour, nearly 75-fold slower than the rate of the acylation reaction. This is in sharp contrast to the in vitro kinetic results, in which the hydrolysis rate is only three-fold slower than the acylation reaction. The significant attenuation of lovastatin hydrolysis rate in vivo is likely due to the permeation barrier of the cell membranes towards the more hydrophobic lovastatin. We attempted to alleviate the membrane permeability barrier by using an alternative strain BL21(DE3)/pXXK2, in which LovD is cloned with an N-terminal pelB signal sequence for localization into the periplasm space. No improvement in the hydrolytic activity is observed for this strain, indicating the impermeability of the outer plasma membrane is the main transport obstacle.

Recovery and Purification of Simvastatin

To access the recovery yield of simvastatin from the whole-cell biocatalytic process, we increased the scale of the bioconversion to a final volume of 200 mL. This was achieved by concentrating 2×1 L of the expression strain in LB medium after overnight expression of LovD. The sodium salt form of monacolin J and DMB-S-MMP were added to a final concentration of 15 mM and 25 mM respectively and the reaction progress was monitored by HPLC. We observed an identical conversion kinetics in the larger scale process and >99% conversion was obtained 24 hours after addition of substrates. Simvastatin obtained from the chemobiosynthetic route can be readily purified from the fermentation broth without using chromatography steps. A centrifugation step was used to separate the cells and the fermentation broth. Intracellular simvastatin was recovered by stirring the cell pellet in acetone, followed by evaporation, and redissolving in dH2O. The aqueous solution containing the intracellular simvastatin was combined with the fermentation broth and was washed with n-hexane to remove DMB-S-MMP. The aqueous solution was then acidified with 6N HCl to pH 2.0, which resulted in precipitation of the free acid forms of simvastatin and DMB-S-MPA. As is known in the art, free acid forms of simvastatin can be converted to sodium, potassium, ammonium, or any other salt derived from alkaline earth elements or other metallic salts. These salts can then be converted to pure simvastatin, for example using common methodologies known in the art. The DMB-S-MPA contaminant can be removed by filtration and washing the filter cake with excessive dH2O. The acidified filtrate contained <1% of total amounts of simvastatin recovered. Nearly pure simvastatin can be recovered by washing the filter cake with acetonitrile, followed by evaporation of the filtrate (Final recovery: 1.13 g, 90%; final purity as determined by HPLC: 98%).

High Cell Density Fermentation

Figure 21A:
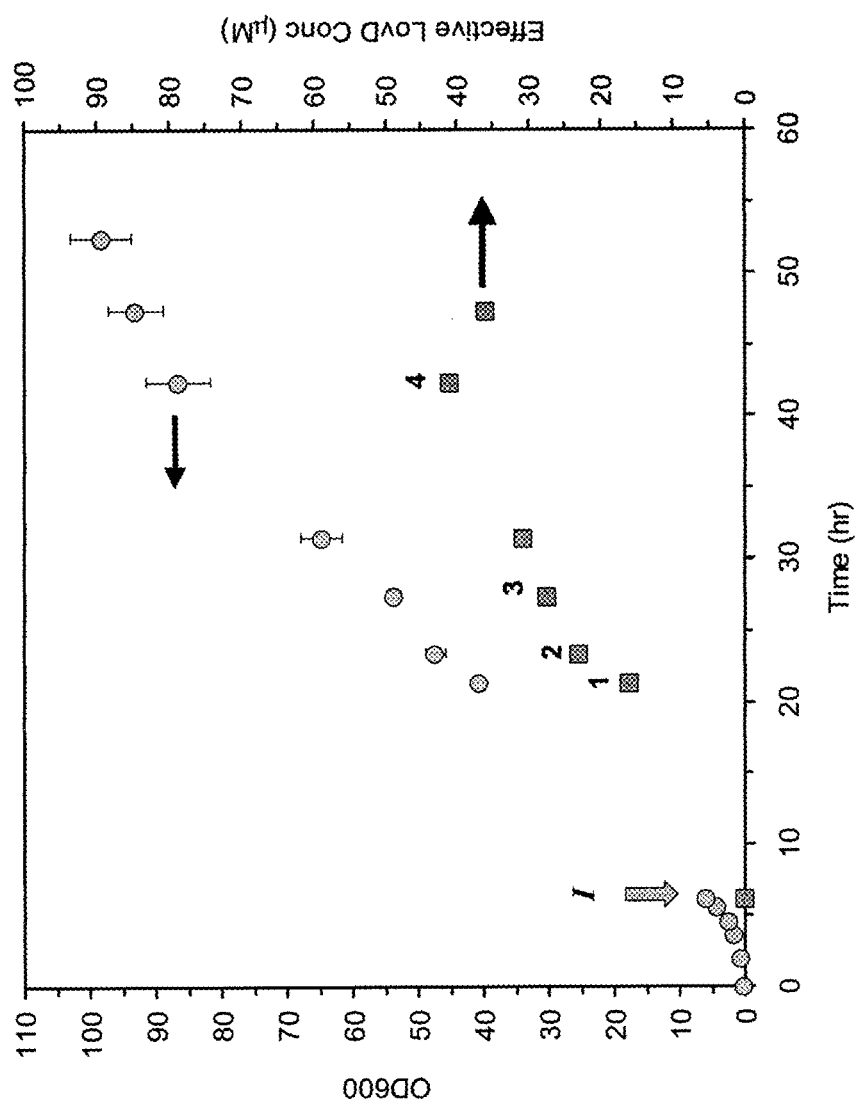
FIGS. 21A and 21B. High density fermentation and biocatalysis.

We explored activity of the whole cell biocatalyst using a high cell density fermentor. The effective LovD concentration measured from a batch fermentor using TB as the medium and that from a fed-batch run using F1 minimal medium are shown in Table 3. Using the fed batch process adopted from that reported by Pfeifer et al (see e.g., Pfeifer et al., 2002, Appl Environ Microbiol 68:3287-92), we were able to obtain cultures with very high cell densities and LovD activities (FIG. 21A). We were able to achieve ~1.5 g/L of active LovD expression at an OD600 of 75 40 hours after inoculation (FIG. 21A).

Figure 21B:
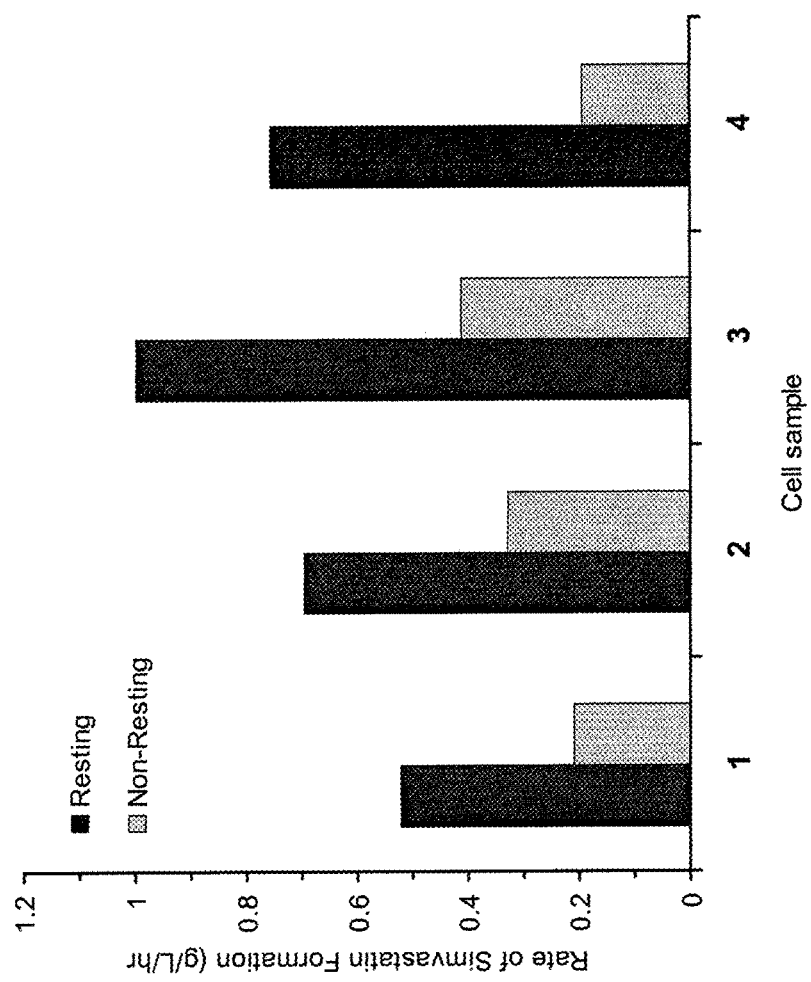

Due to the high cost of the starting materials, we were not able to perform a bioconversion using the entire fermentation broth. Instead, we sampled aliquots of the culture at various points during the fermentation run (FIG. 21A). The activities LovD in each of the time point were determined using the whole cell lysate assay described in Material and Methods. We then performed bioconversion using 1 mL of the culture directly and measured the rate of simvastatin formation (Non-resting cells, FIG. 21B). Alternatively we also examined the properties of the whole cell biocatalyst after resuspension of the cell pellets in PBS, pH 7.4 (Resting cells). As can be seen from FIG. 21B, at each time point, high conversion rates can be obtained when the cells are placed in a resting environment. In addition, the total activity of LovD in the culture is not linearly correlated to rate of conversion. For example, resting cells from time point 3 exhibited the highest rate of simvastatin conversion at nearly 1 g/L/hour, despite having less total LovD activity compared to cells obtained from time point 4. The exceptional robustness of these cells were able to complete conversion of 15 mM monacolin J to simvastatin in less than 8 hours.

A key finding in this example is the identification of yet another acyl thioester that donates an acyl moiety to the C8 hydroxyl group of monacolin J in the presence of LovD acyltransferase, one that is significantly more efficient in this acylation reaction. We previously identified DMB-S-NAC as a substrate of LovD (see e.g., Xie et al., 2006, Chem Biol 13: 1161-1169). However, the acylation reaction proceeded with a less than ideal turnover, and as a result of weak substrate binding to LovD, the second substrate monacolin J became a competitive inhibitor of DMB-S-NAC. The latter property is especially detrimental since it forces the concentration of monacolin J to be kept at a minimum during the bioconversion. Both DMB-S-MMP and DMB-S-MMB are superior to DMB-S-NAC as acyl donors. The kcat value of DMB-S-MMP is approximately 30 fold higher through a subtle structural alteration of the acyl carrier, while the Km value is now comparable to that of monacolin J, hence eliminating substrate inhibition of monacolin J. Furthermore, the 5-MMP thiol precursor is significantly less expensive compared to S-NAC. Considering acyl S-NAC thioester are used prevalently in the precursor directed biosynthesis of natural products (see e.g., Jacobsen et al., 1997, Science 277:367-9), the thioester acyl carriers described in this work may also find important utility in other engineered biosynthesis applications.

We attempted to develop an in vitro biocatalytic process for converting monacolin J to simvastatin. We reasoned that a crudely purified LovD may be useful to overcome any transport and purification difficulties associated with whole cell fermentation. LovD can be readily fractioned from a majority of other cellular proteins by a single 30% ammonium sulfate precipitation step. More than 98% of the LovD activity measured from whole cell lysate can be reconstituted by resolubilizing the precipitated pellet in 50 mM HEPES, pH 7.9. However, LovD precipitates readily (hours) at high protein concentrations (~100 μM) and slowly (days) at lower concentrations (~10 μM) under assay conditions at room temperature. Interestingly, the precipitated LovD protein can be resolublized upon dilution into the same buffer and regains nearly all activity.

When moderate amounts of monacolin J (>5 mM) was used in a batch, in vitro process, we were not able to achieve >60% equilibrium conversion of monacolin J into simvastatin, even after prolonged incubation. This is likely due to a competing reaction in which simvastatin is hydrolyzed back to monacolin J by LovD. When the simvastatin concentration reaches the millimolar range, the velocity of the hydrolysis reaction reaches the maximum value (kcat=0.3 min-1) and therefore significantly impedes the overall net rate of acylation.

Interestingly, the reverse reaction was not a limiting factor under in vivo conditions when the statin concentration was between 10 and 15 mM (4 g/L-6 g/L), as evident in the high conversion (>99%) of monacolin J into simvastatin achieved in this study. We reason that after monacolin J has been converted into simvastatin, multidrug exporters such as the AcrAB-TolC tripartite complex are able to extrude simvastatin from the inner membrane or the periplasm to the medium (see e.g., Murakami et al., 2006, Nature 443:173-9). The impermeability of the E. coli outer membrane prevents reentry of the hydrophobic simvastatin. The more polar, monacolin J is able to continuously diffuse through the membrane and serve as a substrate of LovD. Together, the E. coli outer membrane and its efflux pumps effectively decreases the intracellular concentration of simvastatin available for hydrolysis, hence attenuating the rate of the undesirable reverse reaction, and maximizing the conversion of the desired reaction. However, the efflux pumps normally expressed by E. coli may be overloaded when the substrate concentration are increased to >20 mM. Under elevated concentrations of monacolin J (and hence simvastatin) and DMB-S-MMP, we were able to achieve a maximum conversion of 85~90%. Examination of the distribution of simvastatin in the culture revealed a significant amount (>20%) are localized inside the cells, hence likely leading to increased levels of product hydrolysis. It is unknown whether the simvastatin were partitioned in the inner membrane, the cytoplasm or the periplasm. We are currently examining methods to increase the rate of simvastatin export through overexpression of selected multidrug efflux pumps (see e.g., Masi et al., 2003, J Chromatogr B Analyt Technol Biomed Life Sci 786:197-205).

In this example, we have developed a highly robust whole-cell biocatalytic process for the synthesis of simvastatin from monacolin J. Using E. coli as the host, a laboratory scale process capable of gram-scale synthesis has been implemented. Additionally, a straightforward downstream purification scheme has been devised for facile recovery and purification of the product. We are currently using rational and directed evolution approaches to improve the catalytic turnover rates of LovD. With optimization of the LovD properties, as well as metabolic engineering of the host to improve throughput of the conversion, the chemobiosynthetic route of affording simvastatin can be a competitive and attractive alternative to the synthetic routes shown in FIG. 18.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

TABLES

TABLE 1A

| \ | Acyl-thioesters as substrates of LovD[a] | | |
|---|---|---|---|
| Acyl Thioester Substrate | Conversion[b], RT (min)[c] | Acyl Thioester Substrate | Conversion, RT (min) |
| Acetyl-CoA | 7%, 5.1 | Acetoacetyl-CoA | 89%, 4.6 |
| Propionyl-CoA | 35%, 6.0 | 3-hydroxybutyryl-CoA | 35%, 4.2 |
| Isobutyryl-CoA | 52%, 6.8 | Crotonyl-CoA | 6%, 6.5 |
| Butyryl-CoA | 87%, 6.8 | Malonyl-CoA | N.R.[d] |
| Hexanoyl-CoA | 32%, 8.7 | Decanoyl-CoA | N.R. |
| Longer chain acyl-CoA | 7%, 10.6 | Benzoyl-CoA | 69%, 7.6 |
| Butyryl-SNAC | 50%, 6.8 | Benzoyl-SNAC | 58%, 7.6 |
| (S)-2-methylbutyryl-SNAC | 22%, 7.6 | 2,2-dimethylbutyryl-SNAC | 10%, 8.5 |
| Pentanoyl-SNAC | 52%, 7.8 | Butyryl-S-CH2-CO2Me | 92%, 6.8 |
| Hexanoyl-SNAC | 33%, 8.7 | Benzoyl-S-CH2-CO2Me | 70%, 7.6 |
| Pentenoyl-SNAC | 2%, 7.5 | 2,2-dimethylbutyryl-S-CH2-CO2Me | 17%, 8.5 |

TABLE 1B

Comparison of initial velocities of thioester substrates.

| Thioester Substrate | Abbreviation | Initial Velocity ($k_i$, min$^{-1}$)[a] |
|---|---|---|
| | DMB-S-NAC | 0.02 |
| | DMB-S-MTG | 0.03 |
| | DMB-S-MMP | 0.60 |
| | DMB-S-EMP | 0.70 |
| | DMB-S-MMB | 0.78 |
| | DMB-S-MPA | 0.08 |

[a]Reaction conditions: 1 mM MJ, 4 mM thioester substrate, 10 uM pure LovD, 50 mM HEPES, pH 7.9; initial velocity is defined as the rate of initial turnover in the linear range.

TABLE 2

List of *E. coli* BW25113 mutants screened in this work. The numbers correspond to the TLC lanes shown in FIG. 14A. BioH was shown to be the sole enzyme responsible for DMB-S-MMP hydrolysis.

| No | Gene Deletion |
|---|---|
| 1 | ΔgloB |
| 2 | ΔmhpC |
| 3 | ΔybhA |
| 4 | ΔybiV |
| 5 | ΔycaC |
| 6 | ΔrarA |
| 7 | ΔymdC |
| 8 | ΔycfH |
| 9 | ΔycgM |
| 10 | ΔyciA |
| 11 | ΔycjT |
| 12 | ΔycjY |
| 13 | ΔynbC |
| 14 | ΔyniC |
| 15 | ΔyecD |
| 16 | ΔyegU |
| 17 | ΔlpxL |
| 18 | ΔlpxM |
| 19 | ΔyedL |
| 20 | Δddg |
| 21 | ΔcaiE |
| 22 | ΔwbbJ |
| 23 | ΔycaF |
| 24 | ΔwcaB |
| 25 | ΔfmB |
| 26 | ΔtesB |
| 27 | Δaes |
| 28 | ΔtesA |
| 29 | ΔybgC |
| 30 | ΔybhC |
| 31 | ΔpaaI |
| 32 | ΔyegX |
| 33 | ΔyfbT |
| 34 | ΔypfH |
| 35 | ΔypfI |

TABLE 2-continued

| | |
|---|---|
| 36 | ΔygaP |
| 37 | ΔyqaB |
| 38 | ΔyghX |
| 39 | ΔyghY |
| 40 | ΔygjP |
| 41 | ΔuxaA |
| 42 | ΔyheT |
| 43 | Δphp |
| 44 | ΔyrfG |
| 45 | ΔeptB |
| 46 | ΔyidA |
| 47 | ΔyieH |
| 48 | ΔyigB |
| 49 | ΔyigL |
| 50 | ΔysgA |
| 51 | ΔeptA |
| 52 | ΔyjfP |
| 53 | ΔcheB |
| 54 | ΔyeiG |
| 55 | ΔyqiA |
| 56 | ΔbioH |
| 57 | ΔyjjU |
| 58 | BW25113 |
| 59 | BL21 (DE3) |
| 60 | BL21/pAW31 |

TABLE 3

Comparison of protein yield from different expression conditions[a]

| Fermentation Condition | LovD Concentration (mg/L)[b] |
|---|---|
| LB low density | 96 |
| F1 low density | 34 |
| TB high density | 980 |
| F1 fed-batch high density | 1500 |

[a]The reported yields represent the highest observed yield under respective conditions.
[b]The protein yield is estimated from in vitro assay using whole cell lysate as described in Materials and Methods. The conversion observed is used to estimate the LovD concentration using a turnover rate of 0.6 min$^{-1}$.

TABLE 4

Polypeptide Sequence Information

*Aspergillus terreus* LOVD transesterase. Accession AAD34555
Kennedy et al. Science. 1999 May 21; 284(5418): 1368-72
MGSIIDAAAAADPVVLMETAFRKAVKSRQIPGAVIMARDCSGNLNYTRCF
GARTVRRDECNQLPPLQVDTPCRLASATKLLTTIMALQCMERGLVDLDET
VDRLLPDLSAMPVLEGFDDAGNARLRERRGKITLRHLLTHTSGLSYVFLH
PLLREYMAQGHLQSAEKFGIQSRLAPPAVNDPGAEWIYGANLDWAGKLVE
RATGLDLEQYLQENICAPLGITDMTFKLQQRPDMLARRADQTHRNSADGR
LRYDDSVYFRADGEECFGGQGVFSGPGSYMKVLHSLLKRDGLLLQPQTVD
LMFQPALEPRLEEQMNQHMDASPHINYGGPMPMVLRRSFGLGGIIALEDL
DGENWRRKGSLTFGGGPNIVWQIDPKAGLCTLAFFQLEPWNDPVCRDLTR
TFEHAIYAQYQQG (SEQ ID NO: 1).

*Penicillium citrinum* MlcH transesterase ACCESSION BAC20561
Abe et al., Mol. Genet. Genomics 267 (5), 636-646 (2002)
MAPSIDVIPTAASTAAGMISDMEAAFKSAVKLKQIPGAVVMARSMNGDID
YTRCFGARTVERDECQRLPPMEIDTPLRLASATKLLTTIMALQCMEQGLV
DLDENVNRLLPDLSDMQVLTGFDAAGNAIMRDREGIIKLRHLLTHTSGLS
YAFLHPLLQEYMAKGYLKTAEKFGIQSRLAPPAINDPGVEWIYGANLDWA
GKLIERATGVDLEEFMQKNICEPLGITDMTFKLQQRPDMLARRSDQTRRN
ENGSLRYDDSVYFRHDGEECFGGQGVFCGPESYMKVLNSLMKHDGLLLKK
DTIELMFQPALDAELEKKMNDHMDTTPHINYGAALPPVMRRNFGLGGIIA MGDLDGHNWRREGSLTFGGGPNIVWQIDPTVGLCTLVVFQLEPWNDPICK
DLTRKFEKAMYSQVKCRN (SEQ ID NO: 2).

*Aspergillus terreus* LOVF Polyketide Synthase. AAD34559
Kennedy et al. Science. 1999 May 21; 284(5418): 1368-72
MTPLDAPGAPAPIAMVGMGCRFGGGATDPQKLWKLLEEGGSAWSKIPPSR
FNVGGVYHPNGQRVGSMHVRGGHFLDEDPALFDASFFNMSTEVASCMDPQ
YRLILEVVYEALEAAGIPLEQVSGSKTGVFAGTMYHDYQGSFQRQPEALP
RYFITGNAGTMLANRVSHFYDLRGPSVSIDTACSTTLTALHLAIQSLRAG
ESDMAIVAGANLLLNPDVFTTMSNLGFLSSDGISYSFDSRADGYGRGEGV
AAIVLKTLPDAVRDGDPIRLIVRETAINQDGRTPAISTPSGEAQECLIQD
CYQKAQLDPKQTSYVEAHGTGTRAGDPLELAVISAAFPGQQIQVGSVKAN
IGHTEAVSGLASLIKVALAVEKGVIPPNARFLQPSKKLLKDTHIQIPLCS
QSWIPTDGVRRASINNFGFGGANAHAIVEQYGPFAETSICPPNGYSGNYD
GNLGTDQAHIYVLSAKDENSCMRMVSRLCDYATHARPADDLQLLANIAYT
LGSRRSNFRWKAVCTAHSLTGLAQNLAGEGMRPSKSADQVRLGWVFTGQG
AQWFAMGRELIEMYPVFKEALLECDGYIKEMGSTWSIIEELSRPETESRV
DQAEFSLPLSTALQIALVRLLWSWNIQPVAVTSHSSGEAAAAYAIGALTA
RSAIGISYIRGALTARDRLASVHKGGMLAVGLSRSEVGIYIRQVPLQSGE
CLVVGCVNSPSSVTVSGDLSAIAKLEELLHADRIFARRLKVTQAFHSSHM
NSMTDAFRAGLTELFGADPSDAANASKDVIYASPRTGARLHDMNRLRDPI
HWVECMLHPVEFESAFRRMCLDENDHMPKVDRVIEIGPHGALGGPIKQIM
QLPELATCDIPYLSCLSRGKSSLSTLRLLASELIRAGFPVDLNAINFPRG
CEAARVQVLSDLPPYPWNHETRYWKEPRISQSARQRKGPVHDLIGLQEPL
NLPLARSWHNVLRVSDLPWLRDHVVGSHIVFPGAGFVCMAVMGISTLCSS
DHESDDISYILRDVNFAQALILPADGEEGIDLRLTICAPDQSLGSQDWQR
FLVHSITADKNDWTEHCTGLVRAEMDQPPSSLSNQQRIDPRPWSRKTAPQ
ELWDSLHRVGIRHGPFFRNITCIESDGRGSWCTFAIADTASAMPHAYESQ
HIVHPTTLDSAVQAAYTTLPFAGSRIKSAMVPARVGCMKISSRLADLEAR
DMLRAQAKMHSQSPSALVTDVAVFDEADPVGGPVMELEGLVFQSLGASLG
TSDRDSTDPGNTCSSWHWAPDISLVNPGWLEKTLGTGIQEHEISLILELR
RCSVHFIQEAMESLSVGDVERLSGHLAKFYAWMQKQLACAQNGELGPESS
SWTRDSEQARCSLRSRVVAGSTNGEMICRLGSVLPAILRREVDPLEVMMD
GHLLSRYYVDALKWSRSNAQASELVRLCCHKNPRARILEIGGGTGGCTQL
VVDSLGPNPPVGRYDFTDVSAGFFEAARKRFAGWQNVMDFRKLDIEDDPE
AQGFVCGSYDVVLACQVLHATSNMQRTLTNVRKLLKPGGKLILVETTRDE
LDLFFTFGLLPGWWLSEEPERQSTPSLSPTMWRSMLHTTGFNGVEVEARD
CDSHEFYMISTMMSTAVQATPMSCSVKLPEVLLVYVDSSTPMSWISDLQG
EIRGRNCSVTSLQALRQVPPTEGQICVFLGEVEHSMLGSVTNDDFTLLTS
MLQLAGGTLWVTQGATMKSDDPLKALHLGLLRTMRNESHGKRFVSLDLDP
SRNPWTGDSRDAIVSVLDLISMSDEKEFDYAERDGVIHVPRAFSDSINGG
EEDGYALEPFQDSQHLLRLDIQTPGLLDSLHFTKRNVDTYEPDKLPDDWV
EIEPRAFGLNFRDIMVAMGQLESNVMGFECAGVVTSLSETARTIAPGLAV
GDRVCALMNGHWASRVTTSRTNVVRIPETLSFPHAASIPLAFFTAYISLY
TVARILPGETVLIHAGAGGVGQAAIILAQLTGAEVFTTAGSETKRNLLID
KFHLDPDHVFSSRDSSFVDGIKTRTRGKGVDVVLNSLAGPLLQKSFDCLA
RFGRFVEIGKKDLEQNSRLDMSTFVRNVFSSVDILYWQQAKPAEIFQAM
SEVILLWERTAIGLIHPISEYPMSALEKAFRTMQSGQHVGKIVVTVAPDD
AVLVRQERMPLFLKPNVSYLVAGGLGGIGRRICEWLVDRGARYLIILSRT
ARVDPVVTSLQERGCTVSVQACDVADESQLEAALQQCRAEEMPPIRGVIQ
GAMVLKDALVSQMTADGFHAALRPKVQGSWNLHRIASDVDFFVMLSSLVG
VMGGAGQANYAAAGAFQDALAEHRMAHNQPAVTIDLGMVQSIGYVAETDS
AVAERLQRIGYQPLHEEEVLDVLEQAISPVCSPAAPTRPAVIVTGINTRP
GPHWAHADWMQEARFAGIKYRDPLRDNHGALSLTPAEDDNLHARLNRAIS
QQESIAVIMEAMSCKLISMFGLTDSEMSATQTLAGIGVDSLVAIELRNWI
TAKFNVDISVFELMEGRTIAKVAEVVLQRYKA (SEQ ID NO: 3).

*Escherichia coli* Carboxylesterase bioH ACCESSION Q8FCT4
Welsch et al., Proc. Natl. Acad. Sci. U.S.A. 99(26), 17020-17024(2002)
MNNIWWQTKGQGNVHLVLLHGWGLNAEVWRCIDEELSSHFTLHLVDLPGF
GRSRGFGALSLADMAEAVLQQAPDKAIWLGWSLGGLVASQIALTHPERVQ
ALVTVASSPCFSARDEWPGIKPDVLAGFQQQLSDDFQRTVERFLALQTMG
TETARQDARALKKTVLALPMPEVDVLNGGLEILKTVDLRQPLQNVSMPFL
RLYGYLDGLVPRKVVPMLDKLWPHSESYIFAKAAHAPFISHPAEFCHLLV
ALKQRV (SEQ ID NO: 4).

The invention claimed is:

1. A method of making simvastatin comprising the steps of:

(1) combining together monacolin J; an acyl thioester that donates an acyl moiety to the C8 hydroxyl group of monacolin J in the presence of LovD acyltransferase; and a functional LovD acyltransferase that comprises an amino acid sequence having from 3 to 29 amino acid substitution mutations in SEQ ID NO:1; and (2) allowing the functional LovD acyltransferase to transfer the acyl group from the acyl thioester to regioselectively acylate the C8 hydroxyl group of monacolin J; so that simvastatin is made;

wherein the acyl thioester is selected to possess at least one of the following properties:

(a) is a butyrlyl-thioester, a N-acetylcysteamine thioester or a methyl-thioglycolate thioester;

(b) comprises medium chain length (C3-C6) acyl group moieties;

(c) is able to cross the cellular membranes of *Escherichia coli* or *Aspergillus terreus* cells growing within a fermentation media; or (d) is selected from the group consisting of α-dimethyl-butyryl-S-methyl-mercaptopropionate (DMB-S-MMP), dimethylbutyryl-S-ethyl mercaptopropionate (DMB-S-EMP) and dimethylbutyryl-S-methyl thioglycolate (DMB-S-MTG) and dimethylbutyryl-S-methyl mercaptobutyrate (DMB-S-MMB).

2. The method of claim 1, wherein the monacolin J, the acyl thioester, and the functional LovD acyltransferase are combined in a fermentation media in the presence of an isolated organism, wherein the isolated organism is at least one of:

(a) *Aspergillus terreus* that expresses LovD polypeptide of SEQ ID NO: 1;

(b) *Aspergillus terreus* that does not express LovF polypeptide of SEQ ID NO: 3;

(c) *Escherichia coli* that expresses LovD polypeptide of SEQ ID NO:1; or (d) *Escherichia coli* that does not express bioH polypeptide of SEQ ID NO: 4.

3. The method of claim 1, wherein the acyl thioester is α-dimethylbutyryl-S-methyl-mercaptopropionate, and wherein the α-dimethylbutyryl-S-methyl-mercaptopropionate is present in the fermentation media in a concentration range of 1 mM-100 mM.

4. The method of claim 2, wherein the monacolin J is produced by the isolated organism within the fermentation media.

5. The method of claim 2, wherein the isolated organism is grown under at least one of the following conditions:

(a) at a temperature between 25-40° C.;

(b) for a time period between at least 4 to at least 48 hours;

(c) at a pH between 7-8; or (d) in a fermentation media comprising LB, F1 or TB media.

6. The method of claim 1, wherein the method:

(a) produces a composition of matter comprising 1% or less of the monacolin J that was initially combined with the acyl thioester that donates a dimethylbutyryl moiety to the C8 hydroxyl group of monacolin J in the presence of LovD acyltransferase; or (b) results in at least 95% of the monacolin J added to the combination being converted to simvastatin.

7. The method of claim 1, wherein the acyl thioester is α-dimethylbutyryl-S-methyl-mercaptopropionate, and wherein the α-dimethylbutyryl-S-methyl-mercaptopropionate is present at a concentration range of 1 mM-100 mM.

8. The method of claim 1, wherein:

a) simvastatin is made in vitro in the absence of an isolated organism, or b) simvastatin is made in vivo in a fermentation media in the presence of an isolated organism, and the acyl thioester is derived from an exogenous source.

9. The method of claim 1, wherein the functional LovD acyltransferase exhibits:

a decreased aggregation;
an improved thermal stability;
an improved catalytic activity;
an improved $k_{cat}/K_m$ value;
an improved soluble expression level; or
an improved whole cell activity at 25° C.
as compared to the LovD polypeptide shown in SEQ ID NO:1.

10. The method of claim 1, wherein the functional LovD acyltransferase comprises an amino acid sequence having from 4 to 29 amino acid substitution mutations in SEQ ID NO:1.

11. The method of claim 1, wherein the functional LovD acyltransferase comprises an amino acid sequence having from 5 to 29 amino acid substitution mutations in SEQ ID NO:1.

12. The method of claim 1, wherein the functional LovD acyltransferase comprises an amino acid sequence having from 6 to 29 amino acid substitution mutations in SEQ ID NO:1.

13. The method of claim 1, wherein the functional LovD acyltransferase comprises an amino acid sequence having from 7 to 29 amino acid substitution mutations in SEQ ID NO:1.

14. The method of claim 10, wherein simvastatin is made in vitro in the absence of an isolated organism.

15. The method of claim 11, wherein simvastatin is made in vitro in the absence of an isolated organism.

16. The method of claim 12, wherein simvastatin is made in vitro in the absence of an isolated organism.

17. The method of claim 13, wherein simvastatin is made in vitro in the absence of an isolated organism.

18. The method of claim 1, wherein the acyl thioester is a butyrlyl-thioester, a N-acetylcysteamine thioester or a methyl-thioglycolate thioester.

19. The method of claim 1, wherein the acyl thioester comprises medium chain length (C3-C6) acyl group moieties.

20. A method of making simvastatin comprising the steps of:

(1) combining together monacolin J; an acyl thioester that donates an acyl moiety to the C8 hydroxyl group of monacolin J in the presence of LovD acyltransferase; and a functional LovD acyltransferase that comprises an amino acid sequence having from 3 to 29 amino acid substitution mutations in SEQ ID NO:1; and (2) allowing the functional LovD acyltransferase to transfer the acyl group from the acyl thioester to regioselectively acylate the C8 hydroxyl group of monacolin J;

so that simvastatin is made; wherein the method:

(a) produces a composition of matter comprising 1% or less of the monacolin J that was initially combined with the acyl thioester that donates a dimethylbutyryl moiety to the C8 hydroxyl group of monacolin J in the presence of LovD acyltransferase; and/or (b) results in at least 95% of the monacolin J added to the combination being converted to simvastatin.

\* \* \* \* \*